United States Patent
Reinhardt et al.

(10) Patent No.: US 10,138,232 B2
(45) Date of Patent: Nov. 27, 2018

(54) NAPHTHYRIDINEDIONE DERIVATIVES

(71) Applicant: NOVARTIS AG, Basel OT (CH)

(72) Inventors: Juergen Reinhardt, Basel (CH); Niko Schmiedeberg, Riehen (CH); Carsten Spanka, Lorrach (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/728,613

(22) Filed: Jun. 2, 2015

(65) Prior Publication Data

US 2015/0344476 A1 Dec. 3, 2015

(30) Foreign Application Priority Data

Jun. 3, 2014 (EP) .................... 14170976

(51) Int. Cl.
| | | |
|---|---|---|
| C07D 471/04 | (2006.01) | |
| A61K 31/4375 | (2006.01) | |
| C07D 471/16 | (2006.01) | |
| A61K 31/444 | (2006.01) | |
| A61K 31/4745 | (2006.01) | |
| C07D 471/14 | (2006.01) | |
| C07D 495/14 | (2006.01) | |
| A61K 45/06 | (2006.01) | |

(52) U.S. Cl.
CPC ........ *C07D 471/04* (2013.01); *A61K 31/4375* (2013.01); *A61K 31/444* (2013.01); *A61K 31/4745* (2013.01); *A61K 45/06* (2013.01); *C07D 471/14* (2013.01); *C07D 471/16* (2013.01); *C07D 495/14* (2013.01)

(58) Field of Classification Search
CPC . C07D 471/04; A61K 31/4375; A61K 31/444
USPC .................................... 546/79, 81
See application file for complete search history.

(56) References Cited

U.S. PATENT DOCUMENTS

| | | |
|---|---|---|
| 2009/0163545 A1 | 6/2009 | Goldfarb |
| 2015/0335646 A1 | 11/2015 | Jacoby |
| 2017/0183341 A1 | 6/2017 | Reinhardt et al. |
| 2017/0197959 A1 | 7/2017 | Reinhardt et al. |

FOREIGN PATENT DOCUMENTS

| | | | |
|---|---|---|---|
| EP | 2422817 A1 | 2/2012 | |
| JP | A-H03-81276 | 4/1991 | |
| JP | 3-223283 | * 10/1991 | |
| JP | 2008-504291 A | 2/2008 | |
| JP | 2010-528050 A | 8/2010 | |
| JP | 2013-535479 A | 9/2013 | |
| WO | 96/28444 A1 | 9/1996 | |
| WO | 00/69829 A1 | 11/2000 | |
| WO | 2004/006906 A2 | 1/2004 | |
| WO | 2008/024433 A2 | 2/2008 | |
| WO | 2008/147952 A1 | 12/2008 | |
| WO | 2009/086303 A2 | 7/2009 | |
| WO | 2011/072241 A1 | 6/2011 | |
| WO | 2012/016930 A1 | 2/2012 | |
| WO | 2014/091446 A1 | 6/2014 | |
| WO | 2015/186063 A1 | 12/2015 | |

OTHER PUBLICATIONS

Wermuth Camille , Molecular variations Based on Isosteric Replacements 1996.*
Assessing the Disease-Liability of Mutations in CFTR, Claude Ferec et al 2012.*
CAS Registry No. 898912-80-6, Chemical or Trade Name: Pyrimido[4,5-b]quinoline-4,5(3H,10H)-dione, 3-cyclohexyl-10-methyl-2-propyl—(CA Index Name), Entry Date: Aug. 6, 2006.
CAS Registry No. 896856-26-1, Chemical or Trade Name: Pyrimido[4,5-b]quinoline-4,5(3H,10H)-dione, 3-cycloheptyl-10-methyl-2-(2-thienyl)—(CA Index Name), Entry Date: Jul. 28, 2006.
CAS Registry No. 896853-78-4, Chemical or Trade Name: Pyrimido[4,5-b]quinoline-4,5(3H,10H)-dione, 10-methyl-2,3-diphenyl—(CA Index Name), Entry Date: Jul. 28, 2006.
CAS Registry No. 896846-15-4, Chemical or Trade Name: Pyrimido[4,5-b]quinoline-4,5(3H,10H)-dione, 10-methyl-3-(4-methylphenyl)-2-(3,4,5-trimethoxyphenyl)—(CA Index Name), Entry Date: Jul. 28, 2006.
CAS Registry No. 896835-to-4, Chemical or Trade Name: Pyrimido[4,5-b]quinoline-4,5(3H,10H)-dione, 3-cycloheptyl-2-ethyl-10-methyl—(CA Index Name), Entry Date: Jul. 28, 2006.
CAS Registry No. 896831-02-0, Chemical or Trade Name: Pyrimido[4,5-b]quinoline-4,5(3H,10H)-dione, 3-(3-chlorophenyl)-2,10-dimethyl—(CA Index Name), Entry Date: Jul. 28, 2006.
CAS Registry No. 896826-45-2, Chemical or Trade Name: Pyrimido[4,5-b]quinoline-4,5(3H,10H)-dione, 3-(3,5-dimethylphenyl)-10-methyl-2-(3,4,5-trimethoxyphenyl)—(CA Index Name), Entry Date: Jul. 28, 2006.
CAS Registry No. 896824-67-2, Chemical or Trade Name: Pyrimido[4,5-b]quinoline-4,5(3H,10H)-dione, 3-cyclohexyl-10-methyl-2-(3,4,5-trimethoxyphenyl)—(CA Index Name), Entry Date: Jul. 28, 2006.
CAS Registry No. 896822-97-2, Chemical or Trade Name: Pyrimido[4,5-b]quinoline-4,5(3H,10H)-dione, 2,10-dimethyl-3-phenyl—(CA Index Name), Entry Date: Jul. 28, 2006.

(Continued)

*Primary Examiner* — Rita J Desai
(74) *Attorney, Agent, or Firm* — Asimina T. Georges Evangelinos

(57) ABSTRACT

The invention relates to compound of the formula (I')

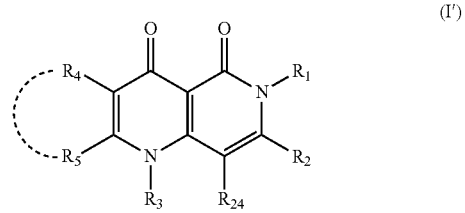

or a salt thereof, wherein the substituents are as defined in the specification; to its preparation, to its use as medicament and to medicaments comprising it.

14 Claims, No Drawings

(56) References Cited

OTHER PUBLICATIONS

CAS Registry No. 896819-48-0, Chemical or Trade Name: Pyrimido[4,5-b]quinoline-4,5(3H,10H)-dione, 3-cyclopentyl-2-(2-furanyl)-10-methyl—(CA Index Name), Entry Date: Jul. 28, 2006.
CAS Registry No. 896820-57-8, Chemical or Trade Name: Pyrimido[4,5-b]quinoline-4,5(3H,10H)-dione, 2-(2-fluorophenyl)-10-methyl-3-phenyl—(CA Index Name), Entry Date: Jul. 28, 2006.
CAS Registry No. 896810-20-1, Chemical or Trade Name: Pyrimido[4,5-b]quinoline-4,5(3H,10H)-dione, 2-(2-chlorophenyl)-3-cyclohexyl-10-methyl—(CA Index Name), Entry Date: Jul. 28, 2006.
CAS Registry No. 896804-46-9, Chemical or Trade Name: Pyrimido[4,5-b]quinoline-4,5(3H,10H)-dione, 3-cycloheptyl-2,10-dimethyl—(CA Index Name), Entry Date: Jul. 28, 2006.
CAS Registry No. 896599-57-8, Chemical or Trade Name: Pyrimido[4,5-b]quinoline-4,5(3H,10H)-dione, 3-cyclohexyl-2-(2-furanyl)-10-methyl—(CA Index Name), Entry Date: Jul. 28, 2006.
CAS Registry No. 896597-46-9, Chemical or Trade Name: Pyrimido[4,5-b]quinoline-4,5(3H,10H)-dione, 3-(3,5-dimethylphenyl)-10-methyl-2-pentyl—(CA Index Name), Entry Date: Jul. 28, 2006.
CAS Registry No. 896076-50-9, Chemical or Trade Name: Pyrimido[4,5-b]quinoline-4,5(3H,10H)-dione, 3-cycloheptyl-2-(2-furanyl)-10-methyl—(CA Index Name), Entry Date: Jul. 25, 2006.
CAS Registry No. 893608-48-5, Chemical or Trade Name: Pyrido[2,3-d]pyrimidine-2,4,7(1H,3H,8H)-trione, 5-hydroxy-8-methyl-6-[(4-nitrophenyl)thio]-1,3-diphenyl—(CA Index Name), Entry Date: Jul. 17, 2006.
CAS Registry No. 883962-63-8, Chemical or Trade Name: Pyrimido[4,5-b]quinoline-4,5(3H,10H)-dione, 10-methyl-2-(3-methylphenyl)-3-phenyl—(CA Index Name), Entry Date: May 12, 2006.
CAS Registry No. 883962-39-8, Chemical or Trade Name: Pyrimido[4,5-b]quinoline-4,5(3H,10H)-dione, 3-cycloheptyl-10-methyl-2-(2-methylphenyl)—(CA Index Name), Entry Date: May 12, 2006.
CAS Registry No. 883962-36-5, Chemical or Trade Name: Pyrimido[4,5-b]quinoline-4,5(3H,10H)-dione, 3-cycloheptyl-2-(2-fluorophenyl)-10-methyl—(CA Index Name), Entry Date: May 12, 2006.
CAS Registry No. 883962-32-1, Chemical or Trade Name: Pyrimido[4,5-b]quinoline-4,5(3H,10H)-dione, 2-(3-bromophenyl)-3-cycloheptyl-10-methyl—(CA Index Name), Entry Date: May 12, 2006.
CAS Registry No. 883962-30-9, Chemical or Trade Name: Pyrimido[4,5-b]quinoline-4,5(3H,10H)-dione, 3-cycloheptyl-10-methyl-2-propyl—(CA Index Name), Entry Date: May 12, 2006.
CAS Registry No. 883962-27-4, Chemical or Trade Name: Pyrimido[4,5-b]quinoline-4,5(3H,10H)-dione, 3-cycloheptyl-10-methyl-2-pentyl—(CA Index Name), Entry Date: May 12, 2006.
CAS Registry No. 883962-24-1, Chemical or Trade Name: Pyrimido[4,5-b]quinoline-4,5(3H,10H)-dione, 3-cycloheptyl-2-cyclohexyl-10-methyl—(CA Index Name), Entry Date: May 12, 2006.
CAS Registry No. 883962-20-7, Chemical or Trade Name: Pyrimido[4,5-b]quinoline-4,5(3H,10H)-dione, 3-cycloheptyl-2-[4-(1,1-dimethylethyl)phenyl]-10-methyl—(CA Index Name), Entry Date: May 12, 2006.
CAS Registry No. 883962-11-6, Chemical or Trade Name: Pyrimido[4,5-b]quinoline-4,5(3H,10H)-dione, 3-cycloheptyl-2-(4-methoxyphenyl)-10-methyl—(CA Index Name), Entry Date: May 12, 2006.
CAS Registry No. 883962-07-0, Chemical or Trade Name: Pyrimido[4,5-b]quinoline-4,5(3H,10H)-dione, 2-(4-chlorophenyl)-3-cycloheptyl-10-methyl—(CA Index Name), Entry Date: May 12, 2006.
CAS Registry No. 883962-04-7, Chemical or Trade Name: Pyrimido[4,5-b]quinoline-4,5(3H,10H)-dione, 3-cycloheptyl-10-methyl-2-phenyl—(CA Index Name), Entry Date: May 12, 2006.
CAS Registry No. 883961-12-4, Chemical or Trade Name: Pyrimido[4,5-b]quinoline-4,5(3H,10H)-dione, 3-cyclopentyl-10-methyl-2-propyl—(CA Index Name), Entry Date: May 12, 2006.
CAS Registry No. 883961-07-7, Chemical or Trade Name: Pyrimido[4,5-b]quinoline-4,5(3H,10H)-dione, 3-cyclopentyl-10-methyl-2-pentyl—(CA Index Name), Entry Date: May 12, 2006.
CAS Registry No. 883961-02-2, Chemical or Trade Name: Pyrimido[4,5-b]quinoline-4,5(3H,10H)-dione, 3-cyclopentyl-2,10-dimethyl—(CA Index Name), Entry Date: May 12, 2006.
CAS Registry No. 883960-98-3, Chemical or Trade Name: Pyrimido[4,5-b]quinoline-4,5(3H,10H)-dione, 3-cyclopentyl-2-(4-fluorophenyl)-10-methyl—(CA Index Name), Entry Date: May 12, 2006.
CAS Registry No. 883960-94-9, Chemical or Trade Name: Pyrimido[4,5-b]quinoline-4,5(3H,10H)-dione, 2-(4-chlorophenyl)-3-cyclopentyl-10-methyl—(CA Index Name), Entry Date: May 12, 2006.
CAS Registry No. 883960-90-5, Chemical or Trade Name: Pyrimido[4,5-b]quinoline-4,5(3H,10H)-dione, 3-cyclopentyl-10-methyl-2-(4-methylphenyl)—(CA Index Name), Entry Date: May 12, 2006.
CAS Registry No. 883960-85-8, Chemical or Trade Name: Pyrimido[4,5-b]quinoline-4,5(3H,10H)-dione, 3-cyclopentyl-10-methyl-2-phenyl—(CA Index Name), Entry Date: May 12, 2006.
CAS Registry No. 883960-81-4, Chemical or Trade Name: Pyrimido[4,5-b]quinoline-4,5(3H,10H)-dione, 3-(4-fluorophenyl)-10-methyl-2-(2-methylphenyl)—(CA Index Name), Entry Date: May 12, 2006.
CAS Registry No. 883960-76-7, Chemical or Trade Name: Pyrimido[4,5-b]quinoline-4,5(3H,10H)-dione, 2-(2-fluorophenyl)-3-(4-fluorophenyl)-10-methyl—(CA Index Name), Entry Date: May 12, 2006.
CAS Registry No. 883960-73-4, Chemical or Trade Name: Pyrimido[4,5-b]quinoline-4,5(3H,10H)-dione, 2-cyclohexyl-3-(4-fluorophenyl)-10-methyl—(CA Index Name), Entry Date: May 12, 2006.
CAS Registry No. 883960-69-8, Chemical or Trade Name: Pyrimido[4,5-b]quinoline-4,5(3H,10H)-dione, 2-[4-(1,1-dimethylethyl)phenyl]-3-(4-fluorophenyl)-10-methyl—(CA Index Name), Entry Date: May 12, 2006.
CAS Registry No. 883960-65-4, Chemical or Trade Name: Pyrimido[4,5-b]quinoline-4,5(3H,10H)-dione, 3-(4-fluorophenyl)-2-(4-methoxyphenyl)-10-methyl—(CA Index Name), Entry Date: May 12, 2006.
CAS Registry No. 883960-62-1, Chemical or Trade Name: Pyrimido[4,5-b]quinoline-4,5(3H,10H)-dione, 2,3-bis(4-fluorophenyl)-10-methyl—(CA Index Name), Entry Date: May 12, 2006.
CAS Registry No. 883960-58-5, Chemical or Trade Name: Pyrimido[4,5-b]quinoline-4,5(3H,10H)-dione, 2-(4-chlorophenyl)-3-(4-fluorophenyl)-10-methyl—(CA Index Name), Entry Date: May 12, 2006.
CAS Registry No. 883960-54-1, Chemical or Trade Name: Pyrimido[4,5-b]quinoline-4,5(3H,10H)-dione, 3-(4-fluorophenyl)-10-methyl-2-(4-methylphenyl)—(CA Index Name), Entry Date: May 12, 2006.
CAS Registry No. 883960-50-7, Chemical or Trade Name: Pyrimido[4,5-b]quinoline-4,5(3H,10H)-dione, 3-(4-fluorophenyl)-10-methyl-2-phenyl—(CA Index Name), Entry Date: May 12, 2006.
CAS Registry No. 883960-47-2, Chemical or Trade Name: Pyrimido[4,5-b]quinoline-4,5(3H,10H)-dione, 3-(3-chlorophenyl)-2-cyclohexyl-10-methyl—(CA Index Name), Entry Date: May 12, 2006.
CAS Registry No. 883960-43-8, Chemical or Trade Name: Index Name Not Yet Assigned, Entry Date: May 12, 2006.
CAS Registry No. 883960-39-2, Chemical or Trade Name: Pyrimido[4,5-b]quinoline-4,5(3H,10H)-dione, 3-(3,5-dimethylphenyl)-10-methyl-2-(2-methylphenyl)—(CA Index Name), Entry Date: 12 May 2006.
CAS Registry No. 83960-35-8, Chemical or Trade Name: Pyrimido[4,5-b]quinoline-4,5(3H,10H)-dione, 3-(3,5-dimethylphenyl)-2-(2-fluorophenyl)-10-methyl—(CA Index Name), Entry Date: May 12, 2006.

(56) References Cited

OTHER PUBLICATIONS

CAS Registry No. 883960-31-4, Chemical or Trade Name: Pyrimido[4,5-b]quinoline-4,5(3H,10H)-dione, 3-(3,5-dimethylphenyl)-10-methyl-2-(1-methylethyl)—(CA Index Name), Entry Date: May 12, 2006.
CAS Registry No. 883960-28-9, Chemical or Trade Name: Pyrimido[4,5-b]quinoline-4,5(3H,10H)-dione, 2-cyclohexyl-3-(3,5-dimethylphenyl)-10-methyl—(CA Index Name), Entry Date: May 12, 2006.
Database Registry (Online) ; Chemical Abstracts Service, Columbus, Ohio, US; Jul. 28, 2006; retrieved from STN, PubChem, Compound Summary for CID 1943301.
CAS Registry No. 883960-25-6, Chemical or Trade Name: Pyrimido[4,5-b]quinoline-4,5(3H,10H)-dione, 3-(3,5-dimethylphenyl)-10-methyl-2-(2-thienyl)—(CA Index Name), Entry Date: May 12, 2006.
CAS Registry No. 883960-21-2, Chemical or Trade Name: Pyrimido[4,5-b]quinoline-4,5(3H,10H)-dione, 3-(3,5-dimethylphenyl)-2-(4-methoxyphenyl)-10-methyl—(CA Index Name), Entry Date: May 12, 2006.
CAS Registry No. 883960-17-6, Chemical or Trade Name: Pyrimido[4,5-b]quinoline-4,5(3H,10H)-dione, 3-(3,5-dimethylphenyl)-2-(4-fluorophenyl)-10-methyl—(CA Index Name), Entry Date: May 12, 2006.
CAS Registry No. 883960-10-9, Chemical or Trade Name: Pyrimido[4,5-b]quinoline-4,5(3H,10H)-dione, 3-(3,5-dimethylphenyl)-10-methyl-2-(4-methylphenyl)—(CA Index Name), Entry Date: May 12, 2006.
CAS Registry No. 883960-13-2, Chemical or Trade Name: Pyrimido[4,5-b]quinoline-4,5(3H,10H)-dione, 2-(4-chlorophenyl)-3-(3,5-dimethylphenyl)-10-methyl—(CA Index Name), Entry Date: May 12, 2006.
CAS Registry No. 883960-07-4, Chemical or Trade Name: Pyrimido[4,5-b]quinoline-4,5(3H,10H)-dione, 3-(3,5-dimethylphenyl)-10-methyl-2-phenyl—(CA Index Name), Entry Date: May 12, 2006.
CAS Registry No. 883960-03-0, Chemical or Trade Name: Pyrimido[4,5-b]quinoline-4,5(3H,10H)-dione, 10-methyl-2-(2-methylphenyl)-3-(4-methylphenyl)—(CA Index Name), Entry Date: May 12, 2006.
CAS Registry No. 883959-99-7, Chemical or Trade Name: Pyrimido[4,5-b]quinoline-4,5(3H,10H)-dione, 10-methyl-2,3-bis(4-methylphenyl)—(CA Index Name), Entry Date: May 12, 2006.
CAS Registry No. 883959-95-3, Chemical or Trade Name: Pyrimido[4,5-b]quinoline-4,5(3H,10H)-dione, 10-methyl-3-(4-methylphenyl)-2-phenyl—(CA Index Name), Entry Date: May 12, 2006.
CAS Registry No. 883958-47-2, Chemical or Trade Name: Pyrimido[4,5-b]quinoline-4,5(3H,10H)-dione, 2-(2-chlorophenyl)-10-methyl-3-phenyl—(CA Index Name), Entry Date: May 12, 2006.
CAS Registry No. 883958-43-8, Chemical or Trade Name: Pyrimido[4,5-b]quinoline-4,5(3H,10H)-dione, 10-methyl-2-(2-methylphenyl)-3-phenyl—(CA Index Name), Entry Date: May 12, 2006.
CAS Registry No. 883958-40-5, Chemical or Trade Name: Pyrimido[4,5-b]quinoline-4,5(3H,10H)-dione, 10-methyl-2-(1-methylethyl)-3-phenyl—(CA Index Name), Entry Date: May 12, 2006.
CAS Registry No. 883958-38-1, Chemical or Trade Name: Pyrimido[4,5-b]quinoline-4,5(3H,10H)-dione, 2-ethyl-10-methyl-3-phenyl—(CA Index Name), Entry Date: May 12, 2006.
CAS Registry No. 883958-36-9, Chemical or Trade Name: Pyrimido[4,5-b]quinoline-4,5(3H,10H)-dione, 2-cyclohexyl-10-methyl-3-phenyl—(CA Index Name), Entry Date: May 12, 2006.
CAS Registry No. 883958-33-6, Chemical or Trade Name: Pyrimido[4,5-b]quinoline-4,5(3H,10H)-dione, 2-[4-(1,1-dimethylethyl)phenyl]-10-methyl-3-phenyl—(CA Index Name), Entry Date: May 12, 2006.
CAS Registry No. 883958-24-5, Chemical or Trade Name: Pyrimido[4,5-b]quinoline-4,5(3H,10H)-dione, 2-(4-methoxyphenyl)-10-methyl-3-phenyl—(CA Index Name), Entry Date: May 12, 2006.
CAS Registry No. 883958-19-8, Chemical or Trade Name: Pyrimido[4,5-b]quinoline-4,5(3H,10H)-dione, 10-methyl-3-phenyl-2-(3,4,5-trimethoxyphenyl)—(CA Index Name), Entry Date: May 12, 2006.
CAS Registry No. 883958-14-3, Chemical or Trade Name: Pyrimido[4,5-b]quinoline-4,5(3H,10H)-dione, 2-(4-fluorophenyl)-10-methyl-3-phenyl—(CA Index Name), Entry Date: May 12, 2006.
CAS Registry No. 883958-09-6, Chemical or Trade Name: Pyrimido[4,5-b]quinoline-4,5(3H,10H)-dione, 2-(4-chlorophenyl)-10-methyl-3-phenyl—(CA Index Name), Entry Date: May 12, 2006.
CAS Registry No. 883958-04-1, Chemical or Trade Name: Pyrimido[4,5-b]quinoline-4,5(3H,10H)-dione, 10-methyl-2-(4-methylphenyl)-3-phenyl—(CA Index Name), Entry Date: May 12, 2006.
CAS Registry No. 883956-72-7, Chemical or Trade Name: Pyrimido[4,5-b]quinoline-4,5(3H,10H)-dione, 3-cyclohexyl-2-(2-fluorophenyl)-10-methyl—(CA Index Name), Entry Date: May 12, 2006.
CAS Registry No. 883956-69-2, Chemical or Trade Name: Pyrimido[4,5-b]quinoline-4,5(3H,10H)-dione, 2-(3-bromophenyl)-3-cyclohexyl-10-methyl—(CA Index Name), Entry Date: May 12, 2006.
CAS Registry No. 883956-66-9, Chemical or Trade Name: Pyrimido[4,5-b]quinoline-4,5(3H,10H)-dione, 2,3-dicyclohexyl-10-methyl—(CA Index Name), Entry Date: May 12, 2006.
CAS Registry No. 883956-62-5, Chemical or Trade Name: Pyrimido[4,5-b]quinoline-4,5(3H,10H)-dione, 3-cyclohexyl-2-[4-(1,1-dimethylethyl)phenyl]-10-methyl—(CA Index Name), Entry Date: May 12, 2006.
CAS Registry No. 883956-55-6, Chemical or Trade Name: Pyrimido[4,5-b]quinoline-4,5(3H,10H)-dione, 2-(4-chlorophenyl)-3-cyclohexyl-10-methyl—(CA Index Name), Entry Date: May 12, 2006.
CAS Registry No. 883956-50-1, Chemical or Trade Name: Pyrimido[4,5-b]quinoline-4,5(3H,10H)-dione, 3-cyclohexyl-10-methyl-2-(4-methylphenyl)—(CA Index Name), Entry Date: May 12, 2006.
CAS Registry No. 883956-47-6, Chemical or Trade Name: Pyrimido[4,5-b]quinoline-4,5(3H,10H)-dione, 3-cyclohexyl-10-methyl-2-phenyl—(CA Index Name), Entry Date: May 12, 2006.
CAS Registry No. 881556-21-4, Chemical or Trade Name: Pyrimido[4,5-b]quinoline-4,5(3H,10H)-dione, 7-chloro-2-(2-chlorophenyl)-3-cycloheptyl-10-methyl—(CA Index Name), Entry Date: Apr. 24, 2006.
CAS Registry No. 881556-16-7, Chemical or Trade Name: Pyrimido[4,5-b]quinoline-4,5(3H,10H)-dione, 3-cycloheptyl-2-(2,4-dichlorophenyl)-10-methyl—(CA Index Name), Entry Date: Apr. 24, 2006.
CAS Registry No. 881556-06-5, Chemical or Trade Name: Pyrimido[4,5-b]quinoline-4,5(3H,10H)-dione, 3-cycloheptyl-2-(4-fluorophenyl)-10-methyl—(CA Index Name), Entry Date: Apr. 24, 2006.
CAS Registry No. 879773-75-8, Chemical or Trade Name: Pyrimido[4,5-b]quinoline-4,5(3H,10H)-dione, 3-cyclohexyl-10-methyl-2-(1-methylethyl)—(CA Index Name), Entry Date: Apr. 9, 2006.
CAS Registry No. 879460-83-0, Chemical or Trade Name: Pyrimido[4,5-b]quinoline-4,5(3H,10H)-dione, 3-cyclohexyl-10-methyl-2-(4-nitrophenyl)—(CA Index Name), Entry Date: Apr. 6, 2006.
CAS Registry No. 879453-73-3, Chemical or Trade Name: Pyrimido[4,5-b]quinoline-4,5(3H,10H)-dione, 3-cycloheptyl-10-methyl-2-(4-nitrophenyl)—(CA Index Name), Entry Date: Apr. 6, 2006.
CAS Registry No. 879450-11-0, Chemical or Trade Name: Pyrimido[4,5-b]quinoline-4,5(3H,10H)-dione, 3-cyclohexyl-10-methyl-2-(3-nitrophenyl)—(CA Index Name), Entry Date: Apr. 6, 2006.
CAS Registry No. 879448-46-1, Chemical or Trade Name: Pyrimido[4,5-b]quinoline-4,5(3H,10H)-dione, 3-cycloheptyl-10-methyl-2-(3-nitrophenyl)—(CA Index Name), Entry Date: Apr. 6, 2006.

(56) References Cited

OTHER PUBLICATIONS

CAS Registry No. 879441-82-4, Chemical or Trade Name: Pyrimido[4,5-b]quinoline-4,5(3H,10H)-dione, 10-methyl-2-(3-nitrophenyl)-3-phenyl—(CA Index Name), Entry Date: Apr. 6, 2006.
CAS Registry No. 879431-52-4, Chemical or Trade Name: Pyrimido[4,5-b]quinoline-4,5(3H,10H)-dione, 10-methyl-2-(4-nitrophenyl)-3-phenyl—(CA Index Name), Entry Date: Apr. 6, 2006.
CAS Registry No. 685894-43-3, Chemical or Trade Name: Pyrido[2,3-d]pyrimidine-2,4,5,7(1H,3H,6H,8H)-tetrone, 6-[[(4-chlorophenyl)amino]methylene]-8-methyl-1,3-diphenyl—(CA Index Name), Entry Date: May 26, 2004.
CAS Registry No. 685894-42-2, Chemical or Trade Name: Pyrido[2,3-d]pyrimidine-2,4,5,7(1H,3H,6H,8H)-tetrone, 8-methyl-6-[[(4-nitrophenyl)amino]methylene]-1,3-diphenyl—(CA Index Name), Entry Date: May 26, 2006.
CAS Registry No. 685894-01-3, Chemical or Trade Name: Pyrido[2,3-d]pyrimidine-2,4,7(1H,3H,8H)-trione, 6-ethyl-5 hydroxy-8-methyl-1,3-diphenyl—(CA Index Name), Entry Date: May 26, 2004.
CAS Registry No. 380632-17-7, Chemical or Trade Name: Pyrido[2,3-d]pyrimidine-2,4,7(1H,3H,8H)-trione, 5-hydroxy-8-methyl-1,3-diphenyl-6-(phenylthio)—(CA Index Name), Entry Date Jan. 7, 2002.
CAS Registry No. 380632-08-6, Chemical or Trade Name: Pyrido[2,3-d]pyrimidine-2,4,7(1H,3H,8H)-trione, 5-hydroxy-8-methyl-6-[(2-nitrophenyl)thio]-1,3-diphenyl—(CA Index Name), Entry Date: Jan. 7, 2002.
CAS Registry No. 380632-07-5, Chemical or Trade Name: Benzoic acid, 2-[(1,2,3,4,7,8-hexahydro-5-hydroxy-8-methyl-2,4,7-trioxo-1,3-diphenylpyrido[2,3-d]pyrimidin-6-yl)thio]—(CA Index Name), Entry Date: Jan. 7, 2002.
CAS Registry No. 380631-08-3, Chemical or Trade Name: Pyrido[2,3-d]pyrimidine-2,4,7(1H,3H,8H)-trione, 6-[(4-chlorophenyl)thio]-5-hydroxy-8-methyl-1,3-diphenyl—(CA Index Name), Entry Date: Jan. 7, 2002.
CAS Registry No. 254991-14-5, Chemical or Trade Name: Pyrido[2,3-d]pyrimidine-2,4,7(1H,3H,4aH)-trione, 8,8a-dihydro-5-hydroxy-8-methyl-1,3-diphenyl—(CA Index Name), Entry Date: Feb. 7, 2000.
Keeling Kim et al., Suppression of nonsense mutations as a therapeutic approach to treat genetic diseases, Wiley Interdisciplinary Reviews, Nov. 2011, vol. 2 (6), pp. 837-852.
Kohra S. et al., Synthesis of Pyrimidine Derivatives by the Reaction of Ketene Dithioacetals with Amides, Journal of Heterocyclic Chemistry, May-Jun. 1988, vol. 25 (3), pp. 959-968.
Kohra S. et al., Reaction of Ketenethioacetals with Carboxamides, Heterocycles, 1983, vol. 20(9), pp. 1745-1750.
Database Registry (Online) ; Chemical Abstracts Service, Columbus, Ohio, US; Jul. 28, 2006; retrieved from STN.
Loudon J.A., Repurposing Amlexanox as a "Run the red light cure-all" with read-through—a "no-nonsense" approach to personalised medicine, J. Bioanal Biomed, 2013, 5:4.
Martin, L., et al., Identification and characterization of small molecules that inhibit nonsense mediated RNA decay and suprress nonsense P53 mutations, Cancer Research, Mar. 24, 2014.
Durand, S., et al., Inhibition of nonsense-mediated mRNA decay (NMD) by a new chemical molecule reveals the dynamic of NMD factors in P-bodies. The Journal of Cell Biology, Sep. 24, 2007; vol. 178 (7); pp. 1145-1160.
Jung M. E., et al, Synthesis and evaluation of compounds that induce readthrough of premature termination codons. Bioorganic and Medicinal Chemistry Letters 21 (2011); pp. 5842-5848.
CAS Registry No. 1431697-95-8, Chemical or Trade Name: Pyrido[2,3-d]pyrimidine-2,4,7(1H,3H,8H)-trione, 8-acetyl-3-cyclopropyl-1-(2-fluoro-4-iodophenyl)-5-hydroxy-6-methyl—(CA Index Name), Entry Date: May 20, 2013.
CAS Registry No. 933651-09-3, Chemical or Trade Name: Pyrido[2,3-d]pyrimidine-2,4,5,7(1H,3H,6H,8H)-tetrone, 8-methyl-1,3-diphenyl-6-[(phenylamino)methylene]—(CA Index Name), Entry Date: Apr. 29, 2007.
CAS Registry No. 933651-02-6, Chemical or Trade Name: Pyrido[2,3-d]pyrimidine-2,4,5,7(1H,3H,6H,8H)-tetrone, 6-[[(4-fluorophenyl)amino]methylene]-8-methyl-1,3-diphenyl—(CA Index Name), Entry Date: Apr. 29, 2007.
CAS Registry No. 915873-05-1, Chemical or Trade Name: Acetic acid, 2-[(3,5,5a,6,8,9-hexahydro-8,8-dimethyl-4,5-dioxo-3-phenyl-4H-pyrano[3',4':5,6]pyrido[2,3-d]pyrimidin-2-yl)thio]-, ethyl ester—(CA Index Name), Entry Date: Dec. 19, 2006.
CAS Registry No. 905693-67-6, Chemical or Trade Name: Pyrido[2,3-d]pyrimidine-2,4,7(1H,3H,8H)-trione, 5-hydroxy-8-methyl-1,3-diphenyl-6-(phenylsulfonyl)—(CA Index Name), Entry Date—Sep. 1, 2006.
CAS Registry No. 904516-17-2, Chemical or Trade Name: Pyrimido[4,5-b]quinoline-4,5(3H,10H)-dione, 3-cyclopentyl-2-(2-fluorophenyl)-10-methyl—(CA Index Name), Entry Date: Aug. 25, 2006.
CAS Registry No. 904509-55-3, Chemical or Trade Name: Pyrimido[4,5-b]quinoline-4,5(3H,10H)-dione, 2-(2-chlorophenyl)-3-cyclopentyl-10-methyl—(CA Index Name), Entry Date: Aug. 25, 2006.
CAS Registry No. 904209-64-9, Chemical or Trade Name: Pyrimido[4,5-b]quinoline-4,5(3H,10H)-dione, 2-cyclohexyl-3-cyclopentyl-10-methyl—(CA Index Name), Entry Date: Aug. 24, 2006.
CAS Registry No. 902335-00-6, Chemical or Trade Name: Pyrimido[4,5-b]quinoline-4,5(3H,10H)-dione, 3-(3-chlorophenyl)-2-(4-fluorophenyl)-10-methyl—(CA Index Name), Entry Date: Aug. 17, 2006.
CAS Registry No. 902334-66-1, Chemical or Trade Name: Pyrimido[4,5-b]quinoline-4,5(3H,10H)-dione, 3-(4-fluorophenyl)-10-methyl-2-pentyl—(CA Index Name), Entry Date: Aug. 17, 2006.
CAS Registry No. 9-2325-19-3, Chemical or Trade Name: Pyrimido[4,5-b]quinoline-4,5(3H,10H)-dione, 3-(3-chlorophenyl)-10-methyl-2-(2-thienyl)—(CA Index Name), Entry Date: Aug. 17, 2006.
CAS Registry No. 902305-58-2, Chemical or Trade Name: Pyrimido[4,5-b]quinoline-4,5(3H,10H)-dione, 3-(3-chlorophenyl)-2-(4-chlorophenyl)-10-methyl—(CA Index Name), Entry Date: Aug. 17, 2006.
CAS Registry No. 902047-47-6, Chemical or Trade Name: Pyrimido[4,5-b]quinoline-4,5(3H,10H)-dione, 3-(3-chlorophenyl)-10-methyl-2-phenyl—(CA Index Name), Entry Date: Aug. 17, 2006.
CAS Registry No. 902013-70-1, Chemical or Trade Name: Pyrimido[4,5-b]quinoline-4,5(3H,10H)-dione, 3-(3-chlorophenyl)-10-methyl-2-(2-methylphenyl)—(CA Index Name), Entry Date: Aug. 16, 2006.
CAS Registry No. 900291-66-9, Chemical or Trade Name: Pyrimido[4,5-b]quinoline-4,5(3H,10H)-dione, 3-cyclohexyl-10-methyl-2-(2-thienyl)—(CA Index Name), Entry Date: Aug. 10, 2006.
CAS Registry No. 900273-38-3, Chemical or Trade Name: Pyrimido[4,5-b]quinoline-4,5(3H,10H)-dione, 3-cyclopentyl-2-[4-(1,1-dimethylethyl)phenyl]-10-methyl—(CA Index Name), Entry Date: Aug. 10, 2006.
CAS Registry No. 900258-30-2, Chemical or Trade Name: Pyrimido[4,5-b]quinoline-4,5(3H,10H)-dione, 10-methyl-3-phenyl-2-(2-thienyl)—(CA Index Name), Entrry Date: Aug. 7, 2006.
CAS Registry No. 899412-73-8, Chemical or Trade Name: Pyrimido[4,5-b]quinoline-4,5(3H,10H)-dione, 2-(2-chlorophenyl)-3-(4-fluorophenyl)-10-methyl—(CA Index Name), Entry Date: Aug. 7, 2006.
CAS Registry No. 899407-21-7, Chemical or Trade Name: Pyrimido[4,5-b]quinoline-4,5(3H,10H)-dione, 3-cyclopentyl-2-(4-methoxyphenyl)-10-methyl—(CA Index Name), Entry Date: Aug. 7, 2006.
CAS Registry No. 899407-12-6, Chemical or Trade Name: Pyrimido[4,5-b]quinoline-4,5(3H,10H)-dione, 3-(4-fluorophenyl)-10-methyl-2-(2-thienyl)—(CA Index Name), Entry Date: Aug. 7, 2006.
CAS Registry No. 899404-28-5, Chemical or Trade Name: Pyrimido[4,5-b]quinoline-4,5(3H,10H)-dione, 3-(3,5-dimethylphenyl)-10-methyl-2-propyl—(CA Index Name), Entry Date: Aug. 7, 2006.

(56) References Cited

OTHER PUBLICATIONS

CAS Registry No. 899403-69-1, Chemical or Trade Name: Pyrimido[4,5-b]quinoline-4,5(3H,10H)-dione, 3-(4-fluorophenyl)-10-methyl-2-(3,4,5-trimethoxyphenyl)—(CA Index Name), Entry Date: Aug. 7, 2006.
CAS Registry No. 899403-25-9, Chemical or Trade Name: Pyrimido[4,5-b]quinoline-4,5(3H,10H)-dione, 3-cyclopentyl-10-methyl-2-(3,4,5-trimethoxyphenyl)—(CA Index Name), Entry Date: Aug. 7, 2006.
CAS Registry No. 899399-83-8, Chemical or Trade Name: Pyrimido[4,5-b]quinoline-4,5(3H,10H)-dione, 3-cyclohexyl-2-(2,4-dichlorophenyl)-10-methyl—(CA Index Name), Entry Date: Aug. 7, 2006.
CAS Registry No. 899392-38-2, Chemical or Trade Name: Pyrimido[4,5-b]quinoline-4,5(3H,10H)-dione, 3-(4-fluorophenyl)-2-(2-furanyl)-10-methyl—(CA Index Name), Entry Date: Aug. 7, 2006.
CAS Registry No. 899392-31-5, Chemical or Trade Name: Pyrimido[4,5-b]quinoline-4,5(3H,10H)-dione, 3-cyclohexyl-2-(4-methoxyphenyl)-10-methyl—(CA Index Name), Entry Date: Aug. 7, 2006.
CAS Registry No. 899385-53-6, Chemical or Trade Name: Pyrimido[4,5-b]quinoline-4,5(3H,10H)-dione, 3-(4-fluorophenyl)-2,10-dimethyl—(CA Index Name), Entry Date: Aug. 7, 2006.
CAS Registry No. 899383-20-1, Chemical or Trade Name: Pyrimido[4,5-b]quinoline-4,5(3H,10H)-dione, 3-cycloheptyl-10-methyl-2-(3,4,5-trimethoxyphenyl)—(CA Index Name), Entry Date: Aug. 7, 2006.
CAS Registry No. 898924-26-0, Chemical or Trade Name: Pyrimido[4,5-b]quinoline-4,5(3H,10H)-dione, 3-cyclohexyl-10-methyl-2-(2-methylphenyl)—(CA Index Name), Entry Date: Aug. 6, 2006.
CAS Registry No. 898923-07-4, Chemical or Trade Name: Pyrimido[4,5-b]quinoline-4,5(3H,10H)-dione, 10-methyl-3-phenyl-2-propyl—(CA Index Name), Entry Date: Aug. 6, 2006.
CAS Registry No. 898921-75-0, Chemical or Trade Name: Pyrimido[4,5-b]quinoline-4,5(3H,10H)-dione, 3-(3,5-dimethylphenyl)-2-ethyl-10-methyl—(CA Index Name), Entry Date: Aug. 6, 2006.
CAS Registry No. 898290-22-4, Chemical or Trade Name: Pyrimido[4,5-b]quinoline-4,5(3H,10H)-dione, 3-cyclopentyl-10-methyl-2-(2-thienyl)—(CA Index Name), Entry Date: Aug. 6, 2006.
CAS Registry No. 898919-89-6, Chemical or Trade Name: Pyrimido[4,5-b]quinoline-4,5(3H,10H)-dione, 2-[4-(1,1-dimethylethyl)phenyl]-3-(3,5-dimethylphenyl)-10-methyl—(CA Index Name), Entry Date: Aug. 6, 2006.
CAS Registry No. 898919-81-8, Chemical or Trade Name: Pyrimido[4,5-b]quinoline-4,5(3H,10H)-dione, 10-methyl-3-(4-methylphenyl)-2-(2-thienyl)—(CA Index Name), Aug. 6, 2006.
CAS Registry No. 898918-37-1, Chemical or Trade Name: Pyrimido[4,5-b]quinoline-4,5(3H,10H)-dione, 2-(4-fluorophenyl)-10-methyl-3-(4-methylphenyl)—(CA Index Name), Entry Date: Aug. 6, 2006.
CAS Registry No. 898918-28-0, Chemical or Trade Name: Pyrimido[4,5-b]quinoline-4,5(3H,10H)-dione, 3-cyclopentyl-10-methyl-2-(1-methylethyl)—(CA Index Name), Entry Date: Aug. 6, 2006.
CAS Registry No. 898917-65-2, Chemical or Trade Name: Pyrimido[4,5-b]quinoline-4,5(3H,10H)-dione, 10-methyl-2-(1-methylethyl)-3-(4-methylphenyl)—(CA Index Name), Entry Date: Aug. 6, 2006.
CAS Registry No. 898916-50-2, Chemical or Trade Name: Pyrimido[4,5-b]quinoline-4,5(3H,10H)-dione, 3-cyclopentyl-2-ethyl-10-methyl—(CA Index Name), Entry Date: Aug. 6, 2006.
CAS Registry No. 898916-26-2, Chemical or Trade Name: Pyrimido[4,5-b]quinoline-4,5(3H,10H)-dione, 3-(3,5-dimethylphenyl)-2,10-dimethyl—(CA Index Name), Entry Date: Aug. 6, 2006.
CAS Registry No. 898915-20-3, Chemical Trade Name: Pyrimido[4,5-b]quinoline-4,5(3H,10H)-dione, 2-ethyl-10-methyl-3-(4-methylphenyl)—(CA Index Name), Entry Date: Aug. 6, 2006.
CAS Registry No. 898913-99-0, Chemical or Trade Name: Pyrimido[4,5-b]quinoline-4,5(3H,10H)-dione, 3-cyclopentyl-10-methyl-2-(2-methylphenyl)—(CA Index Name), Entry Date: Aug. 6, 2006.
CAS Registry No. 898913-20-7, Chemical or Trade Name: Pyrimido[4,5-b]quinoline-4,5(3H,10H)-dione, 10-methyl-2-pentyl-3-phenyl—(CA Index Name), Entry Date: Aug. 6, 2006.

* cited by examiner

NAPHTHYRIDINEDIONE DERIVATIVES

The invention relates to naphthyridinedione derivatives, to their preparation, to their use as medicaments and to medicaments comprising them.

Many human genetic diseases are caused by nonsense mutations (see Keeling et al, WIREs RNA, 2011, 2, 837-852; Linde et al, Trends in Genetics, 2008, 24(11), 552-563; and Rose et al, Pharmacology & Therapeutics, 2012 136(2), 227-266).

A nonsense mutation is a genetic mutation leading to the transformation of a sense codon into a premature termination codon (hereinafter PTC) upstream from the normal termination codon.

Eukaryotic termination codons are UAA, UAG or UGA.

The normal termination codon stops gene translation and enables full-length, wild type protein synthesis. A PTC prevents such wild type protein synthesis and leads to truncated, in many cases inactive, proteins. The resulting partial/total lack of protein leads to the pathology of the disease caused by such a nonsense mutation.

Nonsense mutations can be in-frame mutations, e.g. single nucleic acid exchanges transforming a single codon into a PTC, or frameshift mutations, e.g. a single nucleic acid insertion/deletion transforming the affected codon into a PTC.

A compound being able to suppress the effect of a nonsense mutation is herein called a "nonsense mutation suppressor".

One mechanism to suppress the effect of nonsense mutations is to increase the rate of readthrough events during translation. A compound having this mechanism of action is herein called a "readthrough activator". In a readthrough event, an aminoacyl tRNA being near-cognate is used to recode a termination codon into a sense codon. Under basal conditions, the recoding of a PTC into a sense codon occurs in less than 1% of translation events, while suppression of a normal stop codon occurs at a frequency of <0.1%. Amino acids inserted by recoding will not necessarily be identical to the corresponding amino acids of the wild-type protein; however many amino acid substitutions are functionally tolerated. Thus, a protein produced by readthrough activation may possess activity strongly similar to the wild-type protein. Consequently, by increasing the rate of PTC-recoding enough functional protein may be restored to provide a therapeutic benefit to patients carrying a nonsense mutation.

Another mechanism to suppress the effect of nonsense mutations is to inhibit nonsense-mediated mRNA decay (NMD). A compound having this mechanism of action is herein called a "NMD inhibitor". NMD regulates the total level of PTC-bearing transcripts: it detects and degrades such transcripts to prevent synthesis of truncated proteins which might be nonfunctional or deleterious owing to dominant-negative or gain-of-function effects. Inhibition of NMD increases the number of transcripts available which could also be a mechanism to restore enough functional protein for a therapeutic benefit.

Compounds described as nonsense mutation suppressors are certain aminoglycoside antibiotics, e.g. in WO2007113841, and certain 1,2,4-oxadiazole benzoic acids, e.g. in WO2004091502 and a compound commonly called amlexanox (WO2012016930). WO2009086303 describes agents for increasing lifespan. WO96/28444 describes dihydropyrimidoquinolinone compounds as tyrosine kinase inhibitors.

Other pyridopyrimidinedione derivatives are described in WO199208719, in Synthetic Communications, 1999, 29(22), 3919-3937, in Monatshefte fuer Chemie, 1996, 127(8/9), 917-925.

Nonsense mutation suppressors are considered to be useful in the treatment of a wide range of diseases caused by nonsense mutations. Prominent examples of diseases caused by nonsense mutations are diseases caused by nonsense mutations in lysosomal enzymes, e.g. mucopolysaccharidosis I (Hurler syndrome) caused by nonsense mutations in -L-iduronidase; hemophilia A or hemophilia B caused by nonsense mutations in coagulation factors 7, 8 or 9; cystic fibrosis caused by nonsense mutations in the chloride channel CFTR; diseases caused by nonsense mutations in structural proteins, e.g. Duchenne or Becker Muscle Dystrophy caused by nonsense mutations in dystrophin; or cancer caused by nonsense mutations in APC or p53.

There is a need to provide new nonsense mutation suppressors that are good drug candidates. In particular, preferred compounds should be potent nonsense mutation suppressors whilst showing little potency in other drug target assays, e.g. GPCR or ion channel assays. They should exhibit a low binding to plasma proteins. They should be well absorbed from the gastrointestinal tract, be sufficiently metabolically stable and possess favorable pharmacokinetic properties. They should be non-toxic and demonstrate few side-effects. Furthermore, the ideal drug candidate will be able to exist in a physical form that is stable, non-hygroscopic and easily formulated.

The compounds of the invention are nonsense mutation suppressors and are therefore potentially useful in the treatment of a wide range of diseases caused by nonsense mutations, particularly wherein the disease is selected from hemophilia A, hemophilia B, cystic fibrosis, mucopolysaccharidosis I, Duchenne Muscle Dystrophy, Becker Muscle Dystrophy, loss of APC caused cancer and loss of p53 caused cancer.

In a first aspect, the invention relates to a compound of formula (I') in free form or in pharmaceutically acceptable salt form

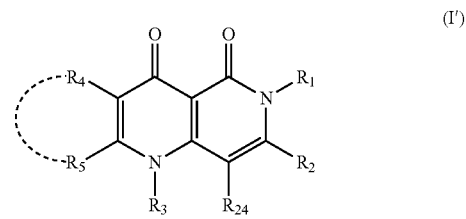

wherein
a) $R_1$ is a five- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_6$;
and
$R_2$ is $C_{2-6}$alkyl which may be substituted once or more than once by $R_7$;
or $R_2$ is —$X_1$—$R_8$; —$X_1$— is —O—, —S— or —N($R_9$)—; $R_9$ is hydrogen or $C_{1-4}$alkyl; and $R_8$ is $C_{1-6}$alkyl which may be substituted once or more than once by $R_{10}$;

or R$_2$ is a three- to seven-membered monocyclic aromatic, saturated or unsaturated non-aromatic ring system, wherein said ring system may contain from 1 to 4 hetero atoms selected from nitrogen, oxygen and sulfur, and wherein said ring system may be substituted once or more than once by R$_{11}$;

or b) R$_1$ is

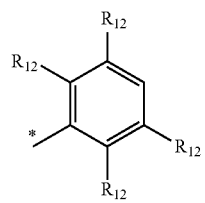

wherein the phenyl ring is attached via the bond marked with an asterisk;

each R$_{12}$ independently is hydrogen, halogen, hydroxyl, amino, cyano, nitro, C$_{1-4}$alkyl, C$_{1-4}$halogenalkyl, C$_{1-4}$hydroxyalkyl, C$_{1-4}$alkoxy-C$_{1-4}$alkyl, amino-C$_{1-4}$alkyl, C$_{1-4}$alkyl-amino-C$_{1-4}$alkyl, di(C$_{1-4}$alkyl)-amino-C$_{1-4}$alkyl, C$_{1-4}$alkoxy, C$_{1-4}$halogenalkoxy, C$_{1-4}$alkylamino or di(C$_{1-4}$alkyl)amino; or C$_{3-6}$cycloalkyl, wherein one carbon atom may be replaced by an oxygen atom, wherein the C$_{3-6}$cycloalkyl may be attached directly or via a C$_{1-2}$alkylene, and wherein the C$_{3-6}$cycloalkyl may be substituted once or more than once by halogen;

and

R$_2$ is C$_{2-7}$alkyl which may be substituted once or more than once by R$_{13}$;

or R$_2$ is —X$_2$—R$_{14}$; —X$_2$— is —O—, —S— or —N(R$_{15}$)—; R$_{15}$ is hydrogen or C$_{1-4}$alkyl; and R$_{14}$ is C$_{1-6}$alkyl which may be substituted once or more than once by R$_{16}$;

or R$_2$ is a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by R$_{17}$;

or c) R$_1$ is a ring selected from pyrrolyl, pyrazolyl, thiophenyl or pyridin-2-yl, which ring may be substituted by C$_{1-3}$alkyl;

and

R$_2$ is C$_{2-7}$alkyl which may be substituted once or more than once by R$_{13}$;

or R$_2$ is —X$_2$—R$_{14}$; —X$_2$— is —O—, —S— or —N(R$_{15}$)—; R$_{15}$ is hydrogen or C$_{1-4}$alkyl; and R$_{14}$ is C$_{1-6}$alkyl which may be substituted once or more than once by R$_{16}$;

or R$_2$ is a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by R$_{17}$;

R$_3$ is hydrogen or —CH$_2$R$_{18}$;

R$_{18}$ is hydrogen, C$_{1-4}$alkyl, C$_{2-6}$alkenyl, C$_{3-6}$cycloalkyl, C$_{1-3}$alkoxyC$_{1-3}$alkyl, hydroxyC$_{1-3}$alkyl or aminoC$_{1-3}$alkyl;

R$_4$ and R$_5$ are independently selected from hydrogen, C$_1$-C$_3$alkyl;

or

R$_4$ and R$_5$ together with the bond to which they are attached form a ring which is selected from
5- to 7-membered monocyclic non-aromatic carbocyclic ring which may be substituted once or more than once by R$_{19}$;
a thiophene ring, which may be substituted once by R$_{20}$;

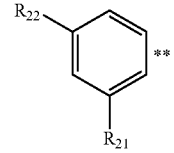

which is fused to the rest of the molecule by the bond marked with two asterisks;

R$_{19}$ and R$_{20}$ are independently selected from halogen, C$_1$-C$_3$alkyl;

R$_{21}$ is hydrogen, halogen, hydroxyl, amino, cyano, C$_{1-4}$alkyl, C$_{1-4}$halogenalkyl, C$_{1-4}$hydroxyalkyl, C$_{1-4}$alkoxy-C$_{1-4}$alkyl, amino-C$_{1-4}$alkyl, C$_{1-4}$alkyl-amino-C$_{1-4}$alkyl, di(C$_{1-4}$alkyl)-amino-C$_{1-4}$alkyl, C$_{1-4}$alkoxy, C$_{1-4}$halogenalkoxy, C$_{1-4}$alkylamino or di(C$_{1-4}$alkyl)amino; or a three- to seven-membered monocyclic aromatic, saturated or unsaturated non-aromatic ring system, wherein said ring system may contain from 1 to 4 hetero atoms selected from nitrogen, oxygen and sulfur, wherein said ring system may be attached directly or via a C$_{1-2}$alkylene, and wherein said ring system may be substituted once or more than once by R$_{23}$; or R$_3$ and R$_{21}$ taken together are —CH$_2$—CH$_2$—;

R$_{22}$ is hydrogen, halogen, hydroxyl, cyano, C$_{1-4}$alkyl, C$_{1-4}$halogenalkyl, C$_{1-4}$hydroxyalkyl, C$_{1-4}$alkoxy-C$_{1-4}$alkyl, amino-C$_{1-4}$alkyl, C$_{1-4}$alkyl-amino-C$_{1-4}$alkyl, di(C$_{1-4}$alkyl)-amino-C$_{1-4}$alkyl, C$_{2-4}$alkenyl, C$_{2-4}$alkinyl, C$_{1-4}$alkoxy or C$_{1-4}$halogenalkoxy; or C$_{3-4}$cycloalkyl, wherein one carbon atom may be replaced by an oxygen atom, wherein the C$_{3-4}$cycloalkyl may be attached directly or via a C$_{1-2}$alkylene, and wherein the C$_{3-4}$cycloalkyl may be substituted once or more than once by halogen;

R$_6$, R$_{11}$, R$_{17}$ and R$_{23}$ each independently is halogen, hydroxyl, amino, cyano, nitro, C$_{1-4}$alkyl, C$_{1-4}$halogenalkyl, C$_{1-4}$hydroxyalkyl, amino-C$_{1-4}$alkyl, C$_{1-4}$alkyl-amino-C$_{1-4}$alkoxy, C$_{1-4}$halogenalkoxy, C$_{1-4}$alkylamino or di(C$_{1-4}$alkyl)amino;

or C$_{3-6}$cycloalkyl, wherein one carbon atom may be replaced by an oxygen atom, wherein the C$_{3-6}$cycloalkyl may be attached directly or via a C$_{1-2}$alkylene, and wherein the C$_{3-6}$cycloalkyl may be substituted once or more than once by halogen;

or two R$_6$, R$_{11}$, R$_{17}$ and R$_{23}$ at the same ring atom together are oxo;

or two R$_6$, R$_{11}$, R$_{17}$ and R$_{23}$ at the same ring carbon atom together with said carbon atom form a C$_{3-6}$cycloalkyl;

R$_7$, R$_{10}$, R$_{13}$ and R$_{16}$ each independently is halogen, hydroxyl, amino, cyano, nitro, C$_{1-4}$alkoxy, C$_{1-4}$halogenalkoxy, C$_{1-4}$alkylamino or di(C$_{1-4}$alkyl)amino;

or C$_{3-6}$cycloalkyl, wherein one carbon atom may be replaced by an oxygen atom, wherein the C$_{3-6}$cycloalkyl may be attached directly or via a C$_{1-2}$alkylene, and wherein the C$_{3-6}$cycloalkyl may be substituted once or more than once by halogen;

or two R$_7$, R$_{10}$, R$_{13}$ or R$_{16}$ at the same carbon atom together are oxo;

or two $R_7$, $R_{10}$, $R_{13}$ or $R_{16}$ at the same carbon atom together with said carbon atom form a $C_{3-6}$cycloalkyl;

$R_{24}$ is hydrogen or halogen.

In an aspect, the invention relates to a compound of formula (I) in free form or in pharmaceutically acceptable salt form

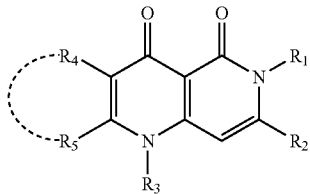

(I)

wherein
a) $R_1$ is a five- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_6$;
and
$R_2$ is $C_{2-6}$alkyl which may be substituted once or more than once by $R_7$;
or $R_2$ is —$X_1$—$R_8$; —$X_1$— is —O—, —S— or —N($R_9$)—; $R_9$ is hydrogen or $C_{1-4}$alkyl; and $R_8$ is $C_{1-6}$alkyl which may be substituted once or more than once by $R_{10}$;
or $R_2$ is a three- to seven-membered monocyclic aromatic, saturated or unsaturated non-aromatic ring system, wherein said ring system may contain from 1 to 4 hetero atoms selected from nitrogen, oxygen and sulfur, and wherein said ring system may be substituted once or more than once by $R_{11}$;
or
b) $R_1$ is

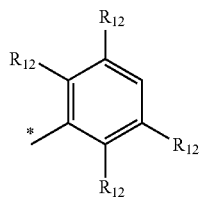

wherein the phenyl ring is attached via the bond marked with an asterisk;
each $R_{12}$ independently is hydrogen, halogen, hydroxyl, amino, cyano, nitro, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, $C_{1-4}$alkoxy, $C_{1-4}$halogenalkoxy, $C_{1-4}$alkylamino or di($C_{1-4}$alkyl)amino; or $C_{3-6}$cycloalkyl, wherein one carbon atom may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;
and
$R_2$ is $C_{2-7}$alkyl which may be substituted once or more than once by $R_{13}$;

or $R_2$ is —$X_2$—$R_{14}$; —$X_2$— is —O—, —S— or —N($R_{15}$)—; $R_{15}$ is hydrogen or $C_{1-4}$alkyl; and $R_{14}$ is $C_{1-6}$alkyl which may be substituted once or more than once by $R_{16}$;
or $R_2$ is a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$;
or
c) $R_1$ is a ring selected from pyrazolyl, thiophenyl or pyridin-2-yl, which ring may be substituted by $C_{1-3}$alkyl;
and
$R_2$ is $C_{2-7}$alkyl which may be substituted once or more than once by $R_{13}$;
or $R_2$ is —$X_2$—$R_{14}$; —$X_2$— is —O—, —S— or —N($R_{15}$)—; $R_{15}$ is hydrogen or $C_{1-4}$alkyl; and $R_{14}$ is $C_{1-6}$alkyl which may be substituted once or more than once by $R_{16}$;
or $R_2$ is a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$;

$R_3$ is hydrogen or —$CH_2R_{18}$;
$R_{18}$ is hydrogen, $C_{1-4}$alkyl, $C_{2-6}$alkenyl, $C_{3-6}$cycloalkyl, $C_{1-3}$alkoxy$C_{1-3}$alkyl, hydroxy$C_{1-3}$alkyl or amino$C_{1-3}$alkyl;
$R_4$ and $R_5$ are independently selected from hydrogen, $C_1$-$C_3$alkyl;
or
$R_4$ and $R_5$ together with the bond to which they are attached form a ring which is selected from
5- to 7-membered monocyclic non-aromatic carbocyclic ring which may be substituted once or more than once by $R_{19}$;
a thiophene ring, which may be substituted once by $R_{20}$;

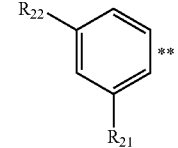

which is fused to the rest of the molecule by the bond marked with two asterisks;
$R_{19}$ and $R_{20}$ are independently selected from halogen, $C_1$-$C_3$alkyl;
$R_{21}$ is hydrogen, halogen, hydroxyl, amino, cyano, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{1-4}$alkoxy, $C_{1-4}$halogenalkoxy, $C_{1-4}$alkylamino or di($C_{1-4}$alkyl)amino; or a three- to seven-membered monocyclic aromatic, saturated or unsaturated non-aromatic ring system, wherein said ring system may contain from 1 to 4 hetero atoms selected from nitrogen, oxygen and sulfur, wherein said ring system may be attached directly or via a $C_{1-2}$alkylene, and wherein said ring system may be substituted once or more than once by $R_{23}$;

or
$R_3$ and $R_{21}$ taken together are —CH$_2$—CH$_2$—;
$R_{22}$ is hydrogen, halogen, hydroxyl, cyano, C$_{1-4}$alkyl, C$_{1-4}$halogenalkyl, C$_{1-4}$hydroxyalkyl, C$_{1-4}$alkoxy-C$_{1-4}$alkyl, di(C$_{1-4}$alkyl)-amino-C$_{1-4}$alkyl, C$_{2-4}$alkenyl, C$_{2-4}$alkinyl, C$_{1-4}$alkoxy or C$_{1-4}$halogenalkoxy; or C$_{3-4}$cycloalkyl, wherein one carbon atom may be replaced by an oxygen atom, wherein the C$_{3-4}$cycloalkyl may be attached directly or via a C$_{1-2}$alkylene, and wherein the C$_{3-4}$cycloalkyl may be substituted once or more than once by halogen;
$R_6$, $R_{11}$, $R_{17}$ and $R_{23}$ each independently is halogen, hydroxyl, amino, cyano, nitro, C$_{1-4}$alkyl, C$_{1-4}$halogenalkyl, C$_{1-4}$hydroxyalkyl, C$_{1-4}$alkoxy-C$_{1-4}$alkyl, amino-C$_{1-4}$alkyl, C$_{1-4}$alkyl-amino-C$_{1-4}$alkyl, C$_{1-4}$alkoxy, C$_{1-4}$halogenalkoxy, C$_{1-4}$alkylamino or di(C$_{1-4}$alkyl)amino;
or C$_{3-6}$cycloalkyl, wherein one carbon atom may be replaced by an oxygen atom, wherein the C$_{3-6}$cycloalkyl may be attached directly or via a C$_{1-2}$alkylene, and wherein the C$_{3-6}$cycloalkyl may be substituted once or more than once by halogen;
or two $R_6$, $R_{11}$, $R_{17}$ and $R_{23}$ at the same ring atom together are oxo;
or two $R_6$, $R_{11}$, $R_{17}$ and $R_{23}$ at the same ring carbon atom together with said carbon atom form a C$_{3-6}$cycloalkyl;
$R_7$, $R_{10}$, $R_{13}$ and $R_{16}$ each independently is halogen, hydroxyl, amino, cyano, nitro, C$_{1-4}$alkoxy, C$_{1-4}$halogenalkoxy, C$_{1-4}$alkylamino or di(C$_{1-4}$alkyl)amino;
or C$_{3-6}$cycloalkyl, wherein one carbon atom may be replaced by an oxygen atom, wherein the C$_{3-6}$cycloalkyl may be attached directly or via a C$_{1-2}$alkylene, and wherein the C$_{3-6}$cycloalkyl may be substituted once or more than once by halogen;
or two $R_7$, $R_{10}$, $R_{13}$ or $R_{16}$ at the same carbon atom together are oxo;
or two $R_7$, $R_{10}$, $R_{13}$ or $R_{16}$ at the same carbon atom together with said carbon atom form a C$_{3-6}$cycloalkyl.

In another aspect, the invention relates to a compound of formula (Ia') in free form or in a pharmaceutically acceptable salt form which is

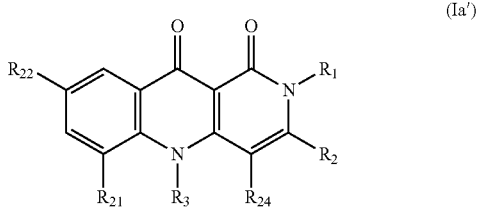

(Ia')

wherein $R_1$, $R_2$, $R_3$, $R_{21}$, $R_{22}$, $R_{24}$ are as defined herein in relation to a compound of formula (I').

In another aspect, the invention relates to a compound of formula (Ia) in free form or in a pharmaceutically acceptable salt form which is

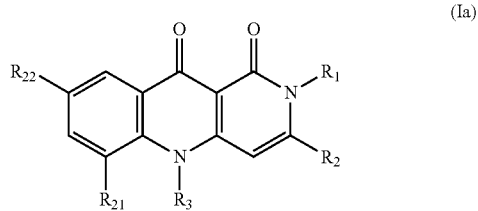

(Ia)

wherein $R_1$, $R_2$, $R_3$, $R_{21}$ and $R_{22}$ are as defined herein in relation to a compound of formula (I).

In a third aspect, the invention relates to a compound of formula (Ib) in free form or in a pharmaceutically acceptable salt form which is

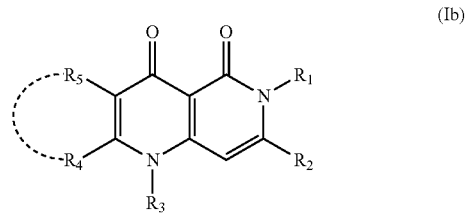

(Ib)

wherein $R_1$, $R_2$, $R_3$, $R_4$ and $R_5$ are as defined herein in relation to a compound of formula (I).

Unless specified otherwise, the term "compounds of the invention" refers to compounds of formula (I), (I'), (Ia), (Ia') and (Ib); salts of the compounds; hydrates or solvates of the compounds and/or salts; as well as all stereoisomers (including diastereoisomers), tautomers and isotopically labeled compounds (including deuterium substitutions); as well as inherently formed moieties (e.g. polymorphs, solvates and/or hydrates).

Unless indicated otherwise, the expressions used in this invention have the following meaning:

"Alkyl" represents a straight-chain or branched-chain alkyl group and, for example, may be methyl, ethyl, n- or iso-propyl or n-, iso-, sec- or tert-butyl; C$_{2-7}$alkyl preferably represents a straight-chain or branched-chain C$_{2-4}$alkyl with particular preference given to ethyl, n-propyl, iso-propyl and tert-butyl. C$_{1-4}$alkyl preferably represents a straight-chain or branched-chain C$_{1-3}$alkyl with particular preference given to methyl, ethyl, n-propyl and iso-propyl.

Each alkyl part of "alkoxy", "halogenalkyl", "hydroxyalkyl", "aminoalkyl", "alkoxyalkyl" and so on shall have the same meaning as described in the above-mentioned definition of "alkyl", especially regarding linearity and preferential size, unless the size is further specified.

"C$_{3-6}$cycloalkyl" represents a saturated alicyclic moiety having from three to six carbon atoms. This term refers to groups such as cyclopropyl, cyclobutyl, cyclopentyl and cyclohexyl.

A substituent being substituted "once or more than once", e.g. as defined in connection with $R_1$, is preferably substituted by one to three substituents. Thus, "once or more than once" includes but is not limited to one, two or three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl.

In the context of the invention, the definition of $R_1$ as a "five- to seven-membered monocyclic saturated or unsaturated non-aromatic ring system, wherein said ring system may contain from 1 to 4 hetero atoms" encompasses five- to seven-membered monocyclic non-aromatic hydrocarbon groups and heterocyclic ring systems of the same sizes.

In the context of the invention, the definition of $R_2$ or $R_4$ as a "three- to seven-membered monocyclic aromatic, saturated or unsaturated non-aromatic ring system, wherein said ring system may contain from 1 to 4 hetero atoms" encompasses three- to seven-membered monocyclic aromatic or non-aromatic hydrocarbon groups and aromatic or non-aromatic heterocyclic ring systems of the same sizes.

Examples of heterocyclic ring systems are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, oxadiazole, dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, pyrimidine, piperazine, triazine, pyrane, tetrahydropyrane, thiopyrane, tetrahydrothiopyrane, oxazine, thiazine, morpholine.

Compounds of formula (I'), (I), (Ia), (Ia) or (Ib) may exist in optically active form or in form of mixtures of optical isomers, e.g. in form of racemic mixtures or diastereomeric mixtures. In particular, asymmetrical carbon atom(s) may be present in the compounds of formula (I'), (I), (Ia), (Ia) or (Ib) and their salts. Unless otherwise provided herein, all optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds described herein may contain one or more asymmetric centers and may thus give rise to enantiomers, diastereomers, and other stereoisomeric forms that may be defined, in terms of absolute stereochemistry, as (R)- or (S)-. Unless otherwise provided herein, the invention is meant to include all such possible isomers, including racemic mixtures, optically pure forms and intermediate mixtures. Optically active (R)- and (S)-isomers may be prepared using chiral synthons or chiral reagents, or resolved using conventional techniques.

If the compound contains a double bond, the substituent may be E or Z configuration.

If the compound contains a disubstituted cycloalkyl, the cycloalkyl substituent may have a cis- or trans-configuration.

Any asymmetric atom (e.g. carbon or the like) of the compound(s) of the invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein, a compound of the invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of formula (I'), (I), (Ia'), (Ia) or (Ib) may occur in various tautomeric forms. All tautomeric forms of the compounds of formula (I) are embraced by the invention.

For example, compounds of formula (I), in which $R_1$, $R_2$, $R_4$ and $R_5$ are as defined under formula (I), and $R_3$ is hydrogen, may exist in tautomeric forms (I-1), (I-2) or (I-3):

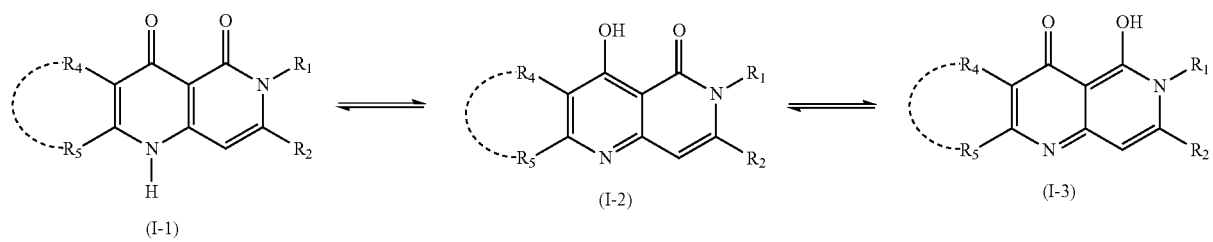

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. The compounds of the invention may be capable of forming acid and/or base salts by virtue of the presence of amino and/or carboxyl groups or groups similar thereto.

The pharmaceutically acceptable salts of the invention can be synthesized from a basic or acidic moiety, by conventional chemical methods. Generally, such salts can be prepared by reacting free acid forms of these compounds with a stoichiometric amount of the appropriate base or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the invention may also form internal salts, e.g., zwitterionic molecules.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}F$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically-labeled compounds of formula (I'), (I), (Ia), (Ia) or (Ib) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I'), (I), (Ia), (Ia) or (Ib). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention that contain groups capable of acting as donors and/or acceptors for hydrogen bonds may be capable of forming co-crystals with suitable co-crystal formers. These co-crystals may be prepared from compounds of formula (I'), (I), (Ia'), (Ia) or (Ib) by known co-crystal forming procedures. Such procedures include grinding, heating, co-subliming, co-melting, or contacting in solution compounds of formula (I'), (I), (Ia'), (Ia) or (Ib) with the co-crystal former under crystallization conditions and isolating co-crystals thereby formed. Suitable co-crystal formers include those described in WO 2004/078163. Hence the invention further provides co-crystals comprising a compound of formula (I'), (I), (Ia), (Ia) or (Ib).

The invention also envisages the use of pro-drugs of the compounds of the invention that convert in vivo to the compounds of the invention. A pro-drug is an active or inactive compound that is modified chemically through in vivo physiological action, such as hydrolysis, metabolism and the like, into a compound of the invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See The Practice of Medicinal Chemistry, Ch. 31-32 (Ed. Wermuth, Academic Press, San Diego, Calif., 2001).

Furthermore, the compounds of the invention, including their salts, can also be obtained in the form of their hydrates, or include other solvents used for their crystallization. The compounds of the invention may inherently or by design form solvates with pharmaceutically acceptable solvents (including water); therefore, it is intended that the invention embrace both solvated and unsolvated forms. The term "solvate" refers to a molecular complex of a compound of the invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the invention, including salts, hydrates and solvates thereof, may inherently or by design form polymorphs.

Various embodiments of the invention are described herein. It will be recognized that features specified in each embodiment may be combined with other specified features to provide further embodiments of the present invention.

The definition of the substituents applies to compounds of formula (I), (I'), (Ia), (Ia') and (Ib) as applicable.

The definition of the substituents applies to the end-products as well as to the corresponding intermediates.

Embodiment 1

A compound of formula (I') in free form or in pharmaceutically acceptable salt form as described above.

Embodiment 2

A compound of formula (I) in free form or in pharmaceutically acceptable salt form as described above.

Embodiment 3

A compound of formula (Ia') in free form or in pharmaceutically acceptable salt form according to embodiment 1 as described above.

Embodiment 4

A compound of formula (Ia) in free form or in pharmaceutically acceptable salt form according to embodiment 2 as described above Embodiment 5

A compound of formula (Ib) in free form or in pharmaceutically acceptable salt form according to embodiment 1 or 2 as described above.

Embodiment 6

A compound of formula (Ia) in free form or in pharmaceutically acceptable salt form according to embodiment 4, wherein
  a) $R_1$ is a five- to six-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_6$;
  and
  $R_2$ is $C_{2-6}$alkyl which may be substituted once or more than once by $R_7$;
  or $R_2$ is —$X_1$—$R_8$; —$X_1$— is —O—, —S— or —N($R_9$)—; $R_9$ is hydrogen or $C_{1-4}$alkyl; and $R_8$ is $C_{1-6}$alkyl which may be substituted once or more than once by $R_{10}$;
  or $R_2$ is a three- to five-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{11}$;
or
  b) $R_1$ is

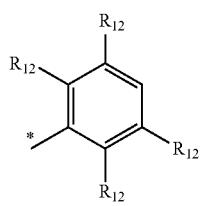

wherein the phenyl ring is attached via the bond marked with an asterisk;
  each $R_{12}$ independently is hydrogen, halogen, hydroxyl, amino, cyano, nitro, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{1-4}$alkoxy, $C_{1-4}$halogenalkoxy, $C_{1-4}$alkylamino or di($C_{1-4}$alkyl)amino; or $C_{3-6}$cycloalkyl, wherein one carbon atom may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;
  and
  $R_2$ is $C_{2-7}$alkyl which may be substituted once or more than once by $R_{13}$;
  or $R_2$ is —$X_2$—$R_{14}$; —$X_2$— is —O—, —S— or —N($R_{15}$)—; $R_{15}$ is hydrogen or $C_{1-4}$alkyl; and $R_{14}$ is $C_{1-6}$alkyl which may be substituted once or more than once by $R_{16}$;
  or $R_2$ is a three- to five-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$;
or
  c) $R_1$ is a ring selected from pyrazolyl, thiophenyl or pyridin-2-yl, which ring may be substituted by $C_{1-3}$alkyl;
  and
  $R_2$ is $C_{2-7}$alkyl which may be substituted once or more than once by $R_{13}$;
  or $R_2$ is —$X_2$—$R_{14}$; —$X_2$— is —O—, —S— or —N($R_{15}$)—; $R_{15}$ is hydrogen or $C_{1-4}$alkyl; and $R_{14}$ is $C_{1-6}$alkyl which may be substituted once or more than once by $R_{16}$;
  or $R_2$ is a three- to five-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$;
$R_3$ is hydrogen or —$CH_2R_{18}$;
$R_{18}$ is hydrogen, $C_{1-4}$alkyl, $C_{2-6}$alkenyl, $C_{3-6}$cycloalkyl, $C_{1-3}$alkoxy$C_{1-3}$alkyl, hydroxy$C_{1-3}$alkyl, or amino $C_{1-3}$alkyl;
and
$R_{21}$ is hydrogen, halogen, hydroxyl, amino, cyano, $C_{1-4}$alkyl, $C_{1-4}$halogenalkyl, $C_{1-4}$hydroxyalkyl, $C_{1-4}$alkylamino-$C_{1-4}$alkyl, di($C_{1-4}$alkoxy, $C_{1-4}$halogenalkoxy, $C_{1-4}$alkylamino or di($C_{1-4}$alkyl)amino;
  or a three- to seven-membered monocyclic aromatic, saturated or unsaturated non-aromatic ring system, wherein said ring system may contain from 1 to 4 hetero atoms selected from nitrogen, oxygen and sulfur, wherein said ring system may be attached directly or via a $C_{1-2}$alkylene, and wherein said ring system may be substituted once or more than once by $R_{23}$;
or
$R_3$ and $R_{21}$ taken together are —$CH_2$—$CH_2$—;
$R_{22}$ is hydrogen, halogen, hydroxyl, cyano, $C_{1-4}$alkyl, $C_{2-4}$alkenyl, $C_{2-4}$alkinyl or $C_{1-4}$alkoxy; or $C_{3-4}$cycloalkyl, wherein one carbon atom may be replaced by an oxygen atom, wherein the $C_{3-4}$cycloalkyl may be attached directly or via a $C_{1-2}$alkylene;

$R_6$, $R_{11}$, $R_{17}$ and $R_{23}$ each independently is halogen, hydroxyl, amino, cyano, nitro, $C_{1-4}$alkyl, $C_{1-4}$halogenalkyl, $C_{1-4}$hydroxyalkyl, $C_{1-4}$alkoxy, $C_{1-4}$halogenalkoxy, $C_{1-4}$alkylamino or di($C_{1-4}$alkyl)amino;

or $C_{3-6}$cycloalkyl, wherein one carbon atom may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;

or two $R_6$, $R_{11}$, $R_{17}$ or $R_{23}$ at the same ring atom together are oxo;

or two $R_6$, $R_{11}$, $R_{17}$ or $R_{23}$ at the same ring carbon atom together with said carbon atom form a $C_{3-6}$cycloalkyl;

$R_7$, $R_{10}$, $R_{13}$ and $R_{16}$ each independently is halogen, hydroxyl, amino, cyano, nitro, $C_{1-4}$alkoxy, $C_{1-4}$halogenalkoxy, $C_{1-4}$alkylamino or di($C_{1-4}$alkyl)amino;

or $C_{3-6}$cycloalkyl, wherein one carbon atom may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;

or two $R_7$, $R_{10}$, $R_{13}$ or $R_{16}$ at the same carbon atom together are oxo;

or two $R_7$, $R_{10}$, $R_{13}$ or $R_{16}$ at the same carbon atom together with said carbon atom form a $C_{3-6}$cycloalkyl.

Embodiment 7

A compound of formula (I), (I'), (Ia), (Ia') or (Ib) in free form or in pharmaceutically acceptable salt form according to any of embodiments 1 to 5, wherein $R_1$ is

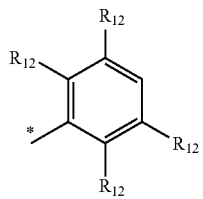

wherein the phenyl ring is attached via the bond marked with an asterisk;

each $R_{12}$ independently is hydrogen, halogen, hydroxyl, amino, cyano, nitro, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{1-4}$alkoxy, $C_{1-4}$halogenalkoxy, $C_{1-4}$alkylamino or di($C_{1-4}$alkyl)amino; or $C_{3-6}$cycloalkyl, wherein one carbon atom may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;

and $R_2$ is $C_{2-7}$alkyl which may be substituted once or more than once by $R_{13}$;

or $R_2$ is —$X_2$—$R_{14}$; —$X_2$— is —O—, —S— or —N($R_{15}$)—; $R_{15}$ is hydrogen or $C_{1-4}$alkyl; and $R_{14}$ is $C_{1-6}$alkyl which may be substituted once or more than once by $R_{16}$;

or $R_2$ is a three- to five-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$.

Embodiment 8

A compound of formula (I), (I'), (Ia), (Ia') or (Ib) in free form or in pharmaceutically acceptable salt form according to embodiment 7, wherein each $R_{12}$ independently is hydrogen, halogen, hydroxyl, amino, cyano, nitro, $C_{1-4}$alkyl, $C_{1-4}$halogenalkyl, $C_{1-4}$alkoxy; or $C_{3-6}$cycloalkyl.

Embodiment 9

A compound of formula (I), (I'), (Ia), (Ia') or (Ib) in free form or in pharmaceutically acceptable salt form according to embodiment 8, wherein each $R_{12}$ is hydrogen.

Embodiment 10

A compound of formula (I), (I'), (Ia), (Ia') or (Ib) in free form or in pharmaceutically acceptable salt form according to any of embodiments 1 to 6, wherein $R_1$ is a five- to six-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_6$;

and $R_2$ is $C_{2-6}$alkyl which may be substituted once or more than once by $R_7$;

or $R_2$ is —$X_1$— is —O—, —S— or —N($R_9$)—; $R_9$ is hydrogen or $C_{1-4}$alkyl; and $R_8$ is $C_{1-6}$alkyl which may be substituted once or more than once by $R_{10}$;

or $R_2$ is a three- to five-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{11}$.

Embodiment 11

A compound of formula (I), (I'), (Ia), (Ia') or (Ib) in free form or in pharmaceutically acceptable salt form according to embodiment 10, wherein each $R_6$ independently is halogen, hydroxyl, amino, cyano, nitro, $C_{1-4}$alkyl, $C_{1-4}$halogenalkyl, $C_{1-4}$alkoxy or $C_{3-6}$cycloalkyl.

Embodiment 12

A compound of formula (I), (I'), (Ia), (Ia') or (Ib) in free form or in pharmaceutically acceptable salt form according to any of embodiments 1 to 6, wherein $R_1$ is pyrazolyl.

Embodiment 13

A compound of formula (I), (I'), (Ia), (Ia') or (Ib) in free form or in pharmaceutically acceptable salt form according to embodiment 12 wherein $R_1$ is a pyrazol-3-yl.

Embodiment 14

A compound of formula (I), (I'), (Ia), (Ia') or (Ib) in free form or in pharmaceutically acceptable salt form according to embodiment 12 or 13 wherein $R_1$ is substituted with methyl.

Embodiment 15

A compound of formula (I), (I'), (Ia), (Ia') or (Ib) according to embodiment 12 in free form or in pharmaceutically acceptable salt form wherein $R_1$ is a pyrazol-5-yl.

Embodiment 16

A compound of formula (I), (I'), (Ia), (Ia') or (Ib) in free form or in pharmaceutically acceptable salt form according to embodiment 15, wherein $R_1$ is a pyrazol-5-yl which is unsubstituted.

Embodiment 17

A compound of formula (I), (I'), (Ia), (Ia') or (Ib) in free form or in pharmaceutically acceptable salt form according to any of embodiments 1 to 6, wherein $R_1$ is thiophenyl.

Embodiment 18

A compound of formula (I), (I'), (Ia), (Ia') or (Ib) in free form or in pharmaceutically acceptable salt form according to embodiment 17, wherein $R_1$ is thiophen-3-yl.

Embodiment 19

A compound of formula (I), (I'), (Ia), (Ia') or (Ib) in free form or in pharmaceutically acceptable salt form according to any of embodiments 1 to 6, wherein $R_1$ is pyridin-2-yl.

Embodiment 20

A compound of formula (I), (I'), (Ia), (Ia') or (Ib) in free form or in pharmaceutically acceptable salt form according to any of embodiments 1 to 19, wherein $R_2$ is $C_{2-6}$alkyl.

Embodiment 21

A compound of formula (I), (I'), (Ia), (Ia') or (Ib) in free form or in pharmaceutically acceptable salt form according to embodiment 20, wherein $R_2$ is n-propyl.

Embodiment 22

A compound of formula (I), (I'), (Ia), (Ia') or (Ib) in free form or in pharmaceutically acceptable salt form according to embodiment 20, wherein $R_2$ is isopropyl.

Embodiment 23

A compound of formula (I), (I'), (Ia), (Ia') or (Ib) in free form or in pharmaceutically acceptable salt form according to any of embodiments 1 to 19, wherein $R_2$ is —$X_1$—$R_8$; is —O— or —S—; and $R_8$ is $C_{1-6}$alkyl.

Embodiment 24

A compound of formula (I), (I'), (Ia), (Ia') or (Ib) in free form or in pharmaceutically acceptable salt form according to any of embodiments 1 to 19, wherein, $R_2$ is —$X_1$—$R_8$; is N($R_9$)—; $R_9$ is $C_{1-4}$alkyl; and $R_8$ is $C_{1-6}$alkyl.

Embodiment 25

A compound of formula (I), (I'), (Ia), (Ia') or (Ib) in free form or in pharmaceutically acceptable salt form according to any of embodiments 1 to 19, wherein $R_2$ is a three- to five-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{11}$; each $R_{11}$ independently is halogen, hydroxyl, amino, cyano, nitro, $C_{1-4}$alkyl, $C_{1-4}$alkoxy or $C_{3-6}$cycloalkyl.

Embodiment 26

A compound of formula (I), (I'), (Ia), (Ia') or (Ib) in free form or in pharmaceutically acceptable salt form according to embodiment 25, wherein $R_2$ is cyclopropyl.

Embodiment 27

A compound of formula (I), (I'), (Ia), (Ia') or (Ib) in free form or in pharmaceutically acceptable salt form according to embodiment 25, wherein $R_2$ is cyclobutyl.

Embodiment 28

A compound of formula (I), (I'), (Ia), (Ia') or (Ib) in free form or in pharmaceutically acceptable salt form according to embodiment 25, wherein $R_2$ is cyclopentyl.

Embodiment 29

A compound of formula (I), (I'), (Ia), (Ia') or (Ib) in free form or in pharmaceutically acceptable salt form according to any of embodiments 1 to 28, wherein $R_3$ is hydrogen or —$CH_2R_{18}$, $R_{18}$ is hydrogen, $C_{1-4}$alkyl, $C_{2-6}$alkenyl or $C_{3-6}$cycloalkyl.

Embodiment 30

A compound of formula (I), (I'), (Ia), (Ia') or (Ib) in free form or in pharmaceutically acceptable salt form according to embodiment 29, wherein $R_3$ is hydrogen.

Embodiment 31

A compound of formula (I), (I'), (Ia), (Ia') or (Ib) in free form or in pharmaceutically acceptable salt form according to embodiment 29, wherein $R_3$ is $CH_2R_{15}$ and $R_{18}$ is hydrogen.

Embodiment 32

A compound of formula (I), (I'), (Ia), or (Ia') in free form or in pharmaceutically acceptable salt form according to any of embodiments 1 to 28 wherein $R_3$ and $R_{21}$ taken together are —$CH_2$—$CH_2$—.

Embodiment 33

A compound of formula (I), (I'), (Ia) or (Ia') in free form or in pharmaceutically acceptable salt form according to any of embodiments 1 to 28 wherein $R_{21}$ is hydrogen.

Embodiment 34

A compound of formula (I), (I'), (Ia), (Ia') or (Ib) in free form or in pharmaceutically acceptable salt form according to any of embodiments 1 to 33, wherein $R_{22}$ is hydrogen, halogen, hydroxyl, cyano, $C_{1-4}$alkyl, $C_{2-4}$alkenyl, $C_{2-4}$alkinyl or $C_{1-4}$alkoxy; or $C_{3-4}$cycloalkyl, wherein one carbon atom may be replaced by an oxygen atom, wherein the $C_{3-4}$cycloalkyl may be attached directly or via a $C_{1-2}$alkylene.

Embodiment 35

A compound of formula (I), (I'), (Ia), (Ia') or (Ib) in free form or in pharmaceutically acceptable salt form according to embodiment 34, wherein $R_{22}$ is hydrogen.

Embodiment 36

A compound of formula (I), (I') or (Ib) in free form or in pharmaceutically acceptable salt form according to any of embodiments 1 to 28, wherein $R_4$ and $R_5$ together with the bond to which they are attached form a 5- to 7-membered monocyclic non-aromatic carbocyclic ring which may be substituted once or more than once by $R_{19}$; $R_{19}$ is selected from halogen or $C_1$-$C_3$alkyl.

Embodiment 37

A compound of formula (I), (I') or (Ib) in free form or in pharmaceutically acceptable salt form according to embodiment 36, wherein $R_4$ and $R_5$ together with the bond to which they are attached form a cyclopentyl ring.

Embodiment 38

A compound of formula (I), (I') or (Ib) in free form or in pharmaceutically acceptable salt form according to embodiment 36, wherein $R_4$ and $R_5$ together with the bond to which they are attached form a cyclohexyl ring.

Embodiment 39

A compound of formula (I), (I') or (Ib) in free form or in pharmaceutically acceptable salt form according to embodiment 38 wherein $R_4$ and $R_5$ together with the bond to which they are attached form a cyclohexyl ring substituted once with $C_1$-$C_3$alkyl.

Embodiment 40

A compound of formula (I), (I') or (Ib) in free form or in pharmaceutically acceptable salt form according to embodiment 36, wherein $R_4$ and $R_5$ together with the bond to which they are attached form a cycloheptyl ring.

Embodiment 41

A compound of formula (I), (I') or (Ib) in free form or in pharmaceutically acceptable salt form according to any of embodiments 1 to 28, wherein $R_4$ and $R_5$ together with the bond to which they are attached form a thiophene ring.

Embodiment 42

A compound of formula (I), (I') or (Ib) in free form or in pharmaceutically acceptable salt form according to embodiment 41, wherein $R_4$ and $R_5$ together with the bond to which they are attached form a thiophene ring attached to the rest of the molecule to give a thieno[2,3-b][1,6]naphthyridinedione compound.

Embodiment 43

A compound of formula (I), (I') or (Ib) in free form or in pharmaceutically acceptable salt form according to embodiment 41, wherein $R_4$ and $R_5$ together with the bond to which they are attached form a thiophene ring attached to the rest of the molecule to give a thieno[3,2-b][1,6]naphthyridinedione compound.

Embodiment 44

A compound of formula (I), (I') or (Ib) in free form or in pharmaceutically acceptable salt form according to embodiment 41, wherein $R_4$ and $R_5$ together with the bond to which they are attached form a thiophene ring attached to the rest of the molecule to give a thieno[3,4-b][1,6]naphthyridinedione compound.

Embodiment 45

A compound of formula (I), (I') or (Ib) in free form or in pharmaceutically acceptable salt form according to any of embodiments 41 to 44, wherein $R_4$ and $R_5$ together with the bond to which they are attached form a thiophene ring substituted once with $C_1$-$C_3$alkyl.

Embodiment 46

A compound of formula (I), (I') or (Ib) in free form or in pharmaceutically acceptable salt form according to any of embodiments 41 to 44, wherein $R_4$ and $R_5$ together with the bond to which they are attached form an unsubstituted thiophene ring.

Embodiment 47

A compound of formula (I), (I') or (Ib) in free form or in pharmaceutically acceptable salt form according to any of embodiments 1 to 28, wherein $R_4$ is hydrogen.

Embodiment 48

A compound of formula (I), (I') or (Ib) in free form or in pharmaceutically acceptable salt form according to any of embodiments 1 to 28, wherein $R_4$ is methyl.

Embodiment 49

A compound of formula (I), (I') or (Ib) in free form or in pharmaceutically acceptable salt form according to any of embodiments 47 or 48, wherein $R_5$ is hydrogen.

Embodiment 50

A compound of formula (I), (I') or (Ib) in free form or in pharmaceutically acceptable salt form according to any of embodiments 47 or 48, wherein $R_5$ is methyl.

Embodiment 51

A compound of formula (I') in free form or in pharmaceutically acceptable salt form according to embodiment 1, which is selected from
3-cyclobutyl-2-phenylbenzo[b][1,6]naphthyridine-1,10(2H,5H)-dione;
3-cyclobutyl-5-methyl-2-phenylbenzo[b][1,6]naphthyridine-1,10(2H,5H)-dione;
3-isopropyl-2-phenylbenzo[b][1,6]naphthyridine-1,10(2H,5H)-dione;
3-isopropyl-5-methyl-2-phenylbenzo[b][1,6]naphthyridine-1,10(2H,5H)-dione;

8-fluoro-3-isopropyl-2-phenylbenzo[b][1,6]naphthyridine-1,10(2H,5H)-dione;
8-fluoro-3-isopropyl-5-methyl-2-phenylbenzo[b][1,6]naphthyridine-1,10(2H,5H)-dione;
8-chloro-3-isopropyl-2-phenylbenzo[b][1,6]naphthyridine-1,10(2H,5H)-dione;
8-chloro-3-isopropyl-5-methyl-2-phenylbenzo[b][1,6]naphthyridine-1,10(2H,5H)-dione;
3-isopropyl-8-methyl-2-phenylbenzo[b][1,6]naphthyridine-1,10(2H,5H)-dione;
3-isopropyl-5,8-dimethyl-2-phenylbenzo[b][1,6]naphthyridine-1,10(2H,5H)-dione;
9-isopropyl-8-phenyl-1H-indolo[1,7-ab][1,6]naphthyridine-6,7(2H,8H)-dione;
7-isopropyl-6-phenylthieno[2,3-b][1,6]naphthyridine-4,5(6H,9H)-dione;
7-isopropyl-9-methyl-6-phenylthieno[2,3-b][1,6]naphthyridine-4,5(6H,9H)-dione;
7-isopropyl-2-methyl-6-phenylthieno[2,3-b][1,6]naphthyridine-4,5(6H,9H)-dione;
7-isopropyl-2,9-dimethyl-6-phenylthieno[2,3-b][1,6]naphthyridine-4,5(6H,9H)-dione;
6-isopropyl-7-phenylthieno[3,2-b][1,6]naphthyridine-8,9(4H,7H)-dione;
6-isopropyl-4-methyl-7-phenylthieno[3,2-b][1,6]naphthyridine-8,9(4H,7H)-dione;
6-isopropyl-2-methyl-7-phenylthieno[3,2-b][1,6]naphthyridine-8,9(4H,7H)-dione;
6-isopropyl-2,4-dimethyl-7-phenylthieno[3,2-b][1,6]naphthyridine-8,9(4H,7H)-dione;
6-isopropyl-3-methyl-7-phenylthieno[3,2-b][1,6]naphthyridine-8,9(4H,7H)-dione;
6-isopropyl-3,4-dimethyl-7-phenylthieno[3,2-b][1,6]naphthyridine-8,9(4H,7H)-dione;
3-isopropyl-2-phenyl-6,7,8,9-tetrahydrobenzo[b][1,6]naphthyridine-1,10(2H,5H)-dione;
3-isopropyl-2-phenyl-5,6,7,8-tetrahydro-1H-cyclopenta[b][1,6]naphthyridine-1,9(2H)-dione;
3-cyclobutyl-5-methyl-2-phenyl-5,6,7,8-tetrahydro-1H-cyclopenta[b][1,6]naphthyridine-1,9(2H)-dione;
7-cyclobutyl-1,2,3-trimethyl-6-phenyl-1,6-naphthyridine-4,5(1H,6H)-dione;
3-cyclobutyl-2-phenyl-5,6,7,8-tetrahydro-1H-cyclopenta[b][1,6]naphthyridine-1,9(2H)-dione;
7-cyclobutyl-2,3-dimethyl-6-phenyl-1,6-naphthyridine-4,5(1H,6H)-dione;
3-cyclobutyl-5-methyl-2-phenyl-6,7,8,9-tetrahydrobenzo[b][1,6]naphthyridine-1,10(2H,5H)-dione;
7-cyclobutyl-9-methyl-6-phenylthieno[2,3-b][1,6]naphthyridine-4,5(6H,9H)-dione;
3-cyclobutyl-2-phenyl-6,7,8,9-tetrahydrobenzo[b][1,6]naphthyridine-1,10(2H,5H)-dione;
7-cyclobutyl-2,9-dimethyl-6-phenylthieno[2,3-b][1,6]naphthyridine-4,5(6H,9H)-dione;
7-cyclobutyl-6-phenylthieno[2,3-b][1,6]naphthyridine-4,5(6H,9H)-dione;
7-cyclobutyl-2-methyl-6-phenylthieno[2,3-b][1,6]naphthyridine-4,5(6H,9H)-dione;
6-cyclobutyl-4-methyl-7-phenylthieno[3,2-b][1,6]naphthyridine-8,9(4H,7H)-dione;
6-cyclobutyl-7-phenylthieno[3,2-b][1,6]naphthyridine-8,9(4H,7H)-dione;
6-cyclobutyl-2,4-dimethyl-7-phenylthieno[3,2-b][1,6]naphthyridine-8,9(4H,7H)-dione;
6-cyclobutyl-2-methyl-7-phenylthieno[3,2-b][1,6]naphthyridine-8,9(4H,7H)-dione;
3-cyclobutyl-5,8-dimethyl-2-phenylbenzo[b][1,6]naphthyridine-1,10(2H,5H)-dione;
3-cyclobutyl-8-fluoro-5-methyl-2-phenylbenzo[b][1,6]naphthyridine-1,10(2H,5H)-dione;
8-chloro-3-cyclobutyl-2-phenylbenzo[b][1,6]naphthyridine-1,10(2H,5H)-dione;
3-cyclobutyl-8-methyl-2-phenylbenzo[b][1,6]naphthyridine-1,10(2H,5H)-dione;
8-chloro-3-cyclobutyl-5-methyl-2-phenylbenzo[b][1,6]naphthyridine-1,10(2H,5H)-dione;
3-isopropyl-6-methoxy-5-methyl-2-phenylbenzo[b][1,6]naphthyridine-1,10(2H,5H)-dione;
3-cyclobutyl-8-fluoro-2-phenylbenzo[b][1,6]naphthyridine-1,10(2H,5H)-dione;
9-cyclobutyl-8-phenyl-1H-indolo[1,7-ab][1,6]naphthyridine-6,7(2H,8H)-dione;
3-cyclobutyl-6-methoxy-5-methyl-2-phenylbenzo[b][1,6]naphthyridine-1,10(2H,5H)-dione;
3-isopropyl-6-methoxy-2-phenylbenzo[b][1,6]naphthyridine-1,10(2H,5H)-dione;
3-cyclobutyl-6-methoxy-2-phenylbenzo[b][1,6]naphthyridine-1,10(2H,5H)-dione;
3-isopropyl-8-methoxy-5-methyl-2-phenylbenzo[b][1,6]naphthyridine-1,10(2H,5H)-dione;
3-isopropyl-8-methoxy-2-phenylbenzo[b][1,6]naphthyridine-1,10(2H,5H)-dione;
8-hydroxy-3-isopropyl-5-methyl-2-phenylbenzo[b][1,6]naphthyridine-1,10(2H,5H)-dione;
6-hydroxy-3-isopropyl-5-methyl-2-phenylbenzo[b][1,6]naphthyridine-1,10(2H,5H)-dione;
3-cyclobutyl-2-cyclopentylbenzo[b][1,6]naphthyridine-1,10(2H,5H)-dione;
3-cyclobutyl-2-cyclopentyl-5-methylbenzo[b][1,6]naphthyridine-1,10(2H,5H)-dione;
2-cyclopentyl-3-isopropylbenzo[b][1,6]naphthyridine-1,10(2H,5H)-dione;
2-cyclopentyl-3-isopropyl-5-methylbenzo[b][1,6]naphthyridine-1,10(2H,5H)-dione;
3-cyclobutyl-2-(pyridin-2-yl)benzo[b][1,6]naphthyridine-1,10(2H,5H)-dione;
3-cyclobutyl-5-methyl-2-(pyridin-2-yl)benzo[b][1,6]naphthyridine-1,10(2H,5H)-dione;
3-cyclobutyl-2-(pyrrolidin-1-yl)benzo[b][1,6]naphthyridine-1,10(2H,5H)-dione;
3-cyclobutyl-5-methyl-2-(pyrrolidin-1-yl)benzo[b][1,6]naphthyridine-1,10(2H,5H)-dione;
4-chloro-3-isopropyl-2-phenylbenzo[b][1,6]naphthyridine-1,10(2H,5H)-dione;
4-chloro-3-isopropyl-5-methyl-2-phenylbenzo[b][1,6]naphthyridine-1,10(2H,5H)-dione; and
4-bromo-3-isopropyl-5-methyl-2-phenylbenzo[b][1,6]naphthyridine-1,10(2H,5H)-dione.

Compounds of the formula (I), (I'), (Ia), (Ia') or (Ib) can be prepared by conventional processes, e.g. as described in the Examples, which processes are further aspects of the invention. Furthermore, compounds of formula (I), (I'), (Ia), (Ia') or (Ib) or their precursors may be obtainable from compounds which are described in the Examples, e.g. by reduction, oxidation and/or other functionalization of resulting compounds and/or by cleavage of any protecting group(s) optionally present, and of recovering the so obtainable compound of the formula (I), (I'), (Ia), (Ia') or (Ib) or the intended precursor. The reactions can be effected according to conventional methods, for example as described in the Examples. The work-up of the reaction mixtures and the purification of the compounds thus obtainable may be carried out in accordance with known procedures. Acid addition salts may be produced from the free bases in known manner, and vice-versa. Starting materials, e.g. starting materials as described in the Examples, may be known or prepared according to conventional procedures starting from known compounds.

The invention also contemplates that compounds of formula (I), (I'), (Ia), (Ia') or (Ib) may be formed by in vivo biotransformation from pro-drugs.

In another aspect, the invention provides a pharmaceutical composition comprising a compound of the invention and a pharmaceutically acceptable carrier. The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula I or pharmaceutical acceptable salts thereof exhibit valuable pharmacological properties and are therefore useful as pharmaceuticals.

Furthermore, compounds of formula (I), (I'), (Ia), (Ia') or (Ib) may be useful for research on diseases caused by nonsense mutations, e.g. as tool compounds.

In particular, compounds of formula (I), (I'), (Ia), (Ia') or (Ib) I act as nonsense mutation suppressors on frequent PTCs, e.g. on Y122X in the mRNA of the cystic fibrosis conductance regulator protein (CFTR). This can be determined in vitro, for example, using cell lines expressing GFP-CFTR-Y122X-Renilla constructs as described herein.

The compounds of the invention may be therefore useful in the prevention, treatment or delay of progression of diseases caused by nonsense mutations The term "disease caused by nonsense mutation" is known in the field. It relates to a disease being present in patients carrying a nonsense mutation in a disease-relevant gene wherein the nonsense mutation causes a partial/total lack of protein which then causes the pathology of the disease.

In one embodiment, the disease is selected from hemophilia A, hemophilia B, cystic fibrosis, mucopolysaccharidosis I, Duchenne Muscle Dystrophy, Becker Muscle Dystrophy, loss of APC caused cancer and loss of p53 caused cancer.

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.01 to about 100 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 1 to about 400 mg, most preferably from about 10 to about 100 mg of the compound of the invention conveniently administered, for example, in divided doses up to four times a day.

For use according to the invention, a compound of the invention may be administered as single active agent or in combination with other active agents, in any usual manner, e.g. orally, for example in the form of tablets or capsules, or parenterally, for example in the form of injection solutions or suspensions. A combination comprising a compound of the invention and another active agent will be referred to as "combination of the invention".

A compound of the invention, may be combined with a readthrough activator, e.g. negamycin, RT13, RT14, ataluren or an aminoglycoside readthrough activator, e.g. paromomycin, amikacin, G418, NB30, NB54 or NB84.

A compound of the invention, may be combined with a nonsense-mediated mRNA decay inhibitor, e.g. NMDI-1.

Negamycin, RT13, RT14, ataluren, aminoglycoside readthrough activators and NMDI-1 are described e.g. in Keeling et al, WIREs RNA, 2011, 2, 837-852.

The compounds of the invention may be useful for the prevention of diseases caused by nonsense mutations.

The compounds of the invention may be useful for the treatment of diseases caused by nonsense mutations.

The compounds of the invention may be useful for the delay of progression of diseases caused by nonsense mutations.

In another embodiment, the invention provides a method of treating a disease caused by a nonsense mutation comprising administration of a therapeutically effective amount of a compound of formula (I), (I'), (Ia), (Ia') or (Ib) or a pharmaceutically acceptable salt thereof. In a further embodiment, the invention provides a method of treating a disease caused by a nonsense mutation comprising administration of a therapeutically effective amount of a compound of formula (I), (I'), (Ia), (Ia') or (Ib) or a pharmaceutically acceptable salt thereof, wherein the disease is selected from the afore-mentioned list, suitably hemophilia A, hemophilia B, cystic fibrosis and mucopolysaccharidosis I (Hurler syndrome).

The term "a therapeutically effective amount" of a compound of the invention refers to an amount of the compound of the invention that will elicit the biological or medical response of a subject, for example, ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to at least partially alleviating, inhibiting, preventing and/or ameliorating a disease caused by nonsense mutations. In another non-limiting embodiment, the term "a therapeutically effective amount" refers to the amount of the compound of the invention that, when administered to a cell, or a tissue, or a non-cellular biological material, or a medium, is effective to at least partially suppress the effect of nonsense mutations.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound of the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it.

EXPERIMENTAL PART

Abbreviations:
NMP 1-methylpyrrolidin-2-one
HOAt 3H-[1,2,3]triazolo[4,5-b]pyridin-3-ol
HATU 2-(3H-[1,2,3]triazolo[4,5-b]pyridin-3-yl)-1,1,3,3-tetramethylisouronium hexafluorophosphate(V)
DMF dimethylformamide
DCM dichloromethane
ACN acetonitrile
TFA trifluoroacetic acid
THF tetrahydrofuran
TBME t-Butylmethylether
r.t. room temperature
SFC superitical fluid chromatography
RP reverse phase
HPLC high pressure liquid chromatography
DIEA N,N-Diisopropylethylamine
rac-BINAP 2,2'-bis(diphenylphosphino)-1,1'-binaphthyl racemate
dba dibenzylideneacetone
DMA dimethylacetamide
LC-MS Method:
Waters Acquity UPLC-SQD system; mobile phase: A: water (0.05% formic acid) B: methanol (0.04% formic acid); gradient: from 2% B to 8% B in 0.1 min, from 8% B to 98% B in 0.5 min, 98% B for 0.1 min; flow rate 1 mL/min; column Waters Acquity UPLC BEH C18, 30×2.1 mm, 1.7 mM; oven temperature 60° C.
NMR Device:
Bruker Avance 400 MHz Ultrashield and Avance 600 MHz Examples Example 1.1: 3-Cyclobutyl-2-phenylbenzo[b][1,6]naphthyridine-1,10(2H,5H)-dione

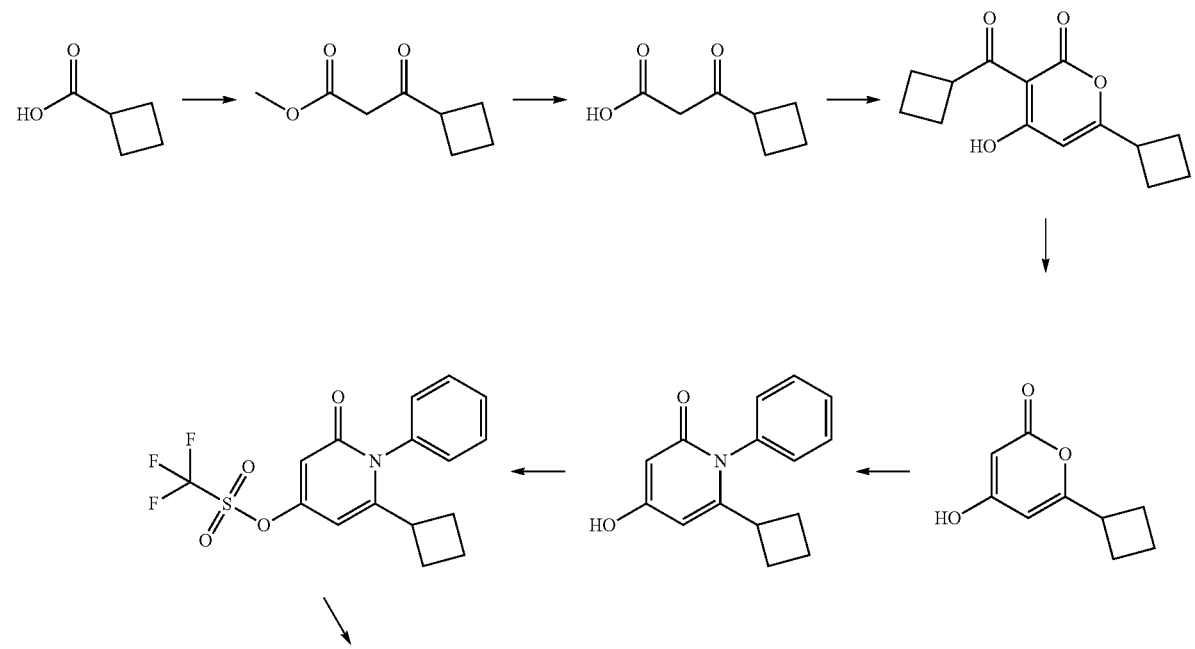

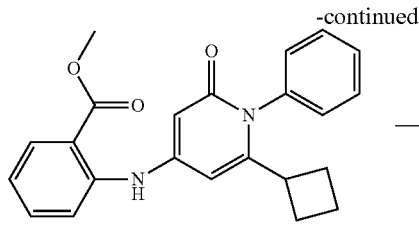 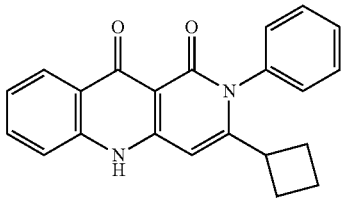

a) 3-(Cyclobutanecarbonyl)-6-cyclobutyl-4-hydroxy-2H-pyran-2-one

Under argon 64.1 g cabonyldiimidazol (396 mmol) was added to 31.5 mL cyclobutanecarboxylic acid (330 mmol) in 300 mL THF within 10 minutes at r.t. After 25 minutes 226 mL DCM, 77 g potassium 3-methoxy-3-oxopropanoate (494 mmol) and 37.7 g magnesium chloride (396 mmol) were added subsequently, heated up to 56° C. within 2.5 hours, and stirred for another 3.5 hours. The resulting suspension was cooled to r.t., 600 mL 2N aqueous hydrochloric acid was added to reach pH 2, another 800 mL water was added and the resulting biphasic solution was separated. The aqueous phase was extracted twice with 250 mL DCM, the combined organic phases were washed with half concentrated aqueous sodium chloride solution, dried over sodium sulfate, filtered and evaporated. The resulting methyl 3-cyclobutyl-3-oxopropanoate (59 g, used for the next step without purification) was dissolved in 10 mL methanol, 378 mL 2M aqueous sodium hydroxide solution was added and the mixture was stirred for one hour. 100 mL TBME was added, the aqueous phase twice extracted with 50 mL TBME, combined aqueous phases filtered and cooled to 5° C. To that solution 65.1 mL concentrated aqueous hydrochloric acid was added to reach pH <1. 167 g solid sodium chloride was added and the mixture was four times extracted with 100 mL ethyl acetate, organic phases washed with water, dried over sodium sulfate, and evaporated to yield 3-cyclobutyl-3-oxopropanoic acid (43 g, used for the next step without purification) as a slightly yellow oil. This oil was dissolved in 508 mL THF and 53.1 g carbonyldiimidazol (328 mmol) were added carefully and stirred for 6 hours. To the resulting solution 50 mL water was added, the THF evaporated under reduced pressure, 200 mL DCM added and washed with 400 mL 2M aqueous hydrochloric acid, 200 mL 0.5M aqueous hydrochloric acid, 200 mL water. Aqueous phases were extracted with 100 mL DCM and combined organic phases were dried over sodium sulfate, filtered and evaporated. The suiting orange oil was purified by liquid chromatography over silica gel with DCM/methanol as eluent. Target fractions were combined and evaporated to yield 22 g 3-(cyclobutanecarbonyl)-6-cyclobutyl-4-hydroxy-2H-pyran-2-one (89 mmol, 53%) as a slowly crystallizing oil.

ESI-MS [M+H]$^+$ 249.2

$^1$H-NMR (400 MHz, CDCl$_3$): δ (ppm)=16.91 (s, 1H), 5.94 (s, 1H), 4.36-4.26 (m, 1H), 3.35 (quint, 1H, J=8.6 Hz), 2.39-2.26 (m, 8H), 2.13-2.00 (m, 2H), 1.99-1.81 (m, 2H).

b) 6-Cyclobutyl-4-hydroxy-2H-pyran-2-one

To 21.9 g 3-(cyclobutanecarbonyl)-6-cyclobutyl-4-hydroxy-2H-pyran-2-one (88 mmol) 65.7 mL concentrated sulfuric acid (88 mmol) was added and the mixture was heated to 105° C. for 20 minutes and then cooled to 0° C. The mixture was carefully poured on 600 g ice, diluted with water to 800 mL volume and extracted three times with 200 mL ethyl acetate. Combined organic phases were washed with aqueous sodium chloride solution, dried over sodium sulfate, filtered, evaporated, and purified by liquid chromatography over silica gel with DCM/methanol as eluent. Target fractions were combined and evaporated to yield 11.6 g 6-cyclobutyl-4-hydroxy-2H-pyran-2-one (70 mmol, 79%) as an off-white solid.

ESI-MS [M+H]$^+$ 167.1

$^1$H-NMR (400 MHz, d$_6$-DMSO): δ (ppm)=11.61 (s, 1H), 5.94 (d, 1H, J=2.1 Hz), 5.22 (d, 1H, J=2.1), 3.36 (quint, 1H, J=8.6 Hz), 2.24-2.08 (m, 4H), 2.04-1.90 (m, 1H), 1.87-1.75 (m, 1H).

c) 6-Cyclobutyl-4-hydroxy-1-phenylpyridin-2(1H)-one

To a suspension of 11.5 g 6-cyclobutyl-4-hydroxy-2H-pyran-2-one (69 mmol) in 231 mL acetic acid and 462 mL water 6.33 mL aniline was added and heated to 85° C. for 22 hours. the mixture was evaporated, twice toluene added and evaporated, 50 mL toluene added and stirred at 50° C. The suspension was filtered, the solid washed with toluene and diethylether, and dried to yield 8.5 g 6-cyclobutyl-4-hydroxy-1-phenylpyridin-2(1H)-one (35 mmol, 51%) as a white solid.

ESI-MS [M+H]$^+$ 242.2

$^1$H-NMR (400 MHz, d$_6$-DMSO): δ (ppm)=10.59 (s, 1H), 7.50-7.39 (m, 3H), 7.19-7.12 (m, 2H), 5.86-5.81 (m, 1H), 5.55 (d, 1H, J=2.4 Hz), 3.09-2.99 (m, 1H), 1.96-1.84 (m, 2H), 1.67-1.50 (m, 4H).

d) 6-Cyclobutyl-2-oxo-1-phenyl-1,2-dihydropyridin-4-yl trifluoromethanesulfonate Under argon 8.4 g 6-cyclobutyl-4-hydroxy-1-phenylpyridin-2(1H)-one (35 mmol) was suspended in 168 mL DCM, cooled to −25° C., 3.94 mL pyridine was added followed by the addition of a solution of 7.03 mL trifluoromethanesulfonic anhydride in 35 mL DCM within 15 minutes. The suspension was stirred for 40 minutes, poured on 250 mL ice/water mixture and vigorously stirred. The aqueous phase was separated, twice extracted with 80 mL DCM, combined organic phases washed with water, dried over sodium sulfate, and evaporated to result in 13 g 6-cyclobutyl-2-oxo-1-phenyl-1,2-dihydropyridin-4-yl trifluoromethanesulfonate (35 mmol, 100%) as a yellow oil that crystallized upon standing.

ESI-MS [M+H]$^+$ 374.1

$^1$H-NMR (400 MHz, d$_6$-DMSO): δ (ppm)=7.58-7.44 (m, 3H), 7.34-7.26 (m, 2H), 6.57-6.52 (m, 1H), 6.44-6.38 (m, 1H), 3.16 (quint, 1H, J=8.8 Hz), 2.09-1.95 (m, 2H), 1.71-1.53 (m, 4H).

e) Methyl 2-((6-cyclobutyl-2-oxo-1-phenyl-1,2-dihydropyridin-4-yl)amino)benzoate Under argon to a suspension of 3 g 6-cyclobutyl-2-oxo-1-phenyl-1,2-dihydropyridin-4-yl trifluoromethane-sulfonate (8.1 mmol), 1.26 mL methyl 2-aminobenzoate (9.7 mmol), and 3.7 g caesium carbonate (11.3 mmol) in 32 mL toluene 60 mg rac-BINAP (0.1 mmol) and 44 mg Pd$_2$(dba)$_3$ (0.05 mmol) were added and heated to 85° C. for 16 hours. The suspension was cooled to r.t, diluted with 60 mL DCM, filtered over Hyflo, and the filtrate evaporated. The resulting orange oil was purified by liquid chromatography over silica gel with DCM/methanol as eluent. Target fractions were combined and evaporated to yield 2.68 g methyl 2-((6-cyclobutyl-2-oxo-1-phenyl-1,2-dihydropyridin-4-yl)amino)benzoate (7.2 mmol, 88%) as an orange oil that crystallized upon standing.

ESI-MS [M+H]$^+$ 375.3

$^1$H-NMR (400 MHz, d$_6$-DMSO): δ (ppm)=9.06 (s, 1H), 7.94 (dd, 1H, J=7.9, 1.6 Hz), 7.66-7.54 (m, 2H), 7.51-7.39 (m, 3H), 7.21-7.15 (m, 3H), 6.09 (d, 1H, J=2.5 Hz), 5.79 (d, 1H, J=2.3 Hz), 3.87 (s, 3H), 3.11-3.03 (m, 1H), 2.01-1.89 (m, 2H), 1.70-1.52 (m, 4H).

f) 3-Cyclobutyl-2-phenylbenzo[b][1,6]naphthyridine-1,10(2H,5H)-dione

To 2.6 g methyl 2-((6-cyclobutyl-2-oxo-1-phenyl-1,2-dihydropyridin-4-yl)amino)benzoate (6.9 mmol) 38 g polyphoshoric acid was added and heated to 120° C. for 40 minutes. To the mixture 43 g ice was added, diluted with 440 mL water and 152 g potassium bicarbonate was slowly added to reach pH 7-8. 100 mL TBME and 200 mL methanol, followed by 200 mL water were added and thoroughly stirred for 30 minutes. The suspension was filtered, the solid washed with water and TBME and dried to yield 1.7 g 3-cyclobutyl-2-phenylbenzo[b][1,6]naphthyridine-1,10(2H,5H)-dione (5 mmol, 72%) as an off-white solid.

ESI-MS [M+H]$^+$ 343.2; LCMS Rt [min], meth. A: 0.60.

$^1$H-NMR (400 MHz, d$_6$-DMSO): δ (ppm)=11.79 (s, 1H), 8.10 (d, 1H, J=7.9), 7.67 (t, 1H, J=7.6), 7.57-7.41 (m, 4H), 7.36-7.20 (m, 3H), 6.22 (s, 1H), 3.20-3.06 (m, 1H), 2.06-1.90 (m, 2H), 1.74-1.56 (m, 4H).

Example 1.2: 3-Cyclobutyl-5-methyl-2-phenylbenzo[b][1,6]naphthyridine-1,10(2H,5H)-dione

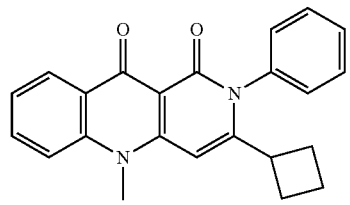 [SMILES: Cn1c2ccccc2c(=O)c2c(=O)n(-c3ccccc3)c(C3CCC3)cc21]

To a suspension of 1.65 g 3-cyclobutyl-2-phenylbenzo[b][1,6]naphthyridine-1,10(2H,5H)-dione (4.8 mmol) (example 1.1) in 50 mL DMF 4.7 g caesium carbonate (14.4 mmol) and 0.9 mL methyliodide (14.4 mmol) were added and stirred for 2.5 hours at r.t. To the resulting suspension 100 mL water was slowly added, cooled to 10° C., stirred for 30 minutes, filtered, the solid washed with 20 mL DMF/water (1:2, v/v), 100 mL water and dried under vacuum at 60° C. to yield 1.4 g 3-cyclobutyl-5-methyl-2-phenylbenzo[b][1,6]naphthyridine-1,10(2H,5H)-dione (4 mmol, 84%) as an off-white solid.

ESI-MS [M+H]$^+$ 357.2; LCMS Rt [min], meth. A: 0.61.

$^1$H-NMR (400 MHz, d$_6$-DMSO): δ (ppm)=8.21 (dd, 1H, J=7.8, 1.8 Hz), 7.84 (d, 1H, J=8.6 Hz), 7.81-7.73 (m, 1H), 7.58-7.46 (m, 3H), 7.38 (t, 1H, J=7.4 Hz), 7.28-7.23 (m, 2H), 6.43 (s, 1H), 3.92 (s, 3H), 3.22-3.12 (m, 1H), 2.22-2.10 (m, 2H), 1.73-1.56 (m, 4H).

Example 1.3: 3-isopropyl-2-phenylbenzo[b][1,6]naphthyridine-1,10(2H,5H)-dione

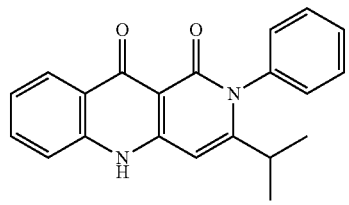 [SMILES: CC(C)c1cc2[nH]c3ccccc3c(=O)c2c(=O)n1-c1ccccc1]

a) 4-hydroxy-6-isopropyl-1-phenylpyridin-2(1H)-one

To a solution of 3 g (19.5 mmol) 4-hydroxy-6-isopropyl-2H-pyran-2-one (CAS 220809-37-0, commercially available) in 120 mL water and 60 mL acetic acid 1.8 mL (19.5 mmol) anilin was added and stirred at 85° C. for 16.5 hours. The resulting mixture was evaporated and purified by liquid chromatography over silica gel with DCM/methanol as eluent. Target fractions were combined and evaporated to yield 1.5 g (6.4 mmol, 33%) 4-hydroxy-6-isopropyl-1-phenylpyridin-2(1H)-one as a white solid b) 6-isopropyl-2-oxo-1-phenyl-1,2-dihydropyridin-4-yl trifluoromethanesulfonate To a suspension of 2.9 g (12.8 mmol) of 4-hydroxy-6-isopropyl-1-phenylpyridin-2(1H)-one in 34 mL DCM 1.87 mL (23 mmol) pyridine were added, the mixture was cooled to −25° C., a solution of 2.7 mL (16 mmol) trifluoromethanesulfonic anhydride in 11.4 mL DCM was dropwise over 10 minutes and stirred for another 45 minutes at −25° C. 40 mL and 80 mL water were added, the organic phase extracted with 80 mL water and brine, the aqueous phases twice extracted with 80 mL ethylacetate, combined organic phases dried over sodium sulfate and evaporated to yield 4.6 g (12.4 mmol, 97%) 6-isopropyl-2-oxo-1-phenyl-1,2-dihydropyridin-4-yl trifluoromethanesulfonate as a yellow solid.

c) methyl 2-((6-isopropyl-2-oxo-1-phenyl-1,2-dihydropyridin-4-yl)amino)benzoate

To a solution of 4.6 g (12.7 mmol) 6-isopropyl-2-oxo-1-phenyl-1,2-dihydropyridin-4-yl trifluoromethane-sulfonate in 71 mL dioxane 1.8 mL (14 mmol) methyl 2-aminobenzoate and 4.4. mL (25 mmol) DIEA were added. Then 0.63 g (1 mmol) rac-BINAP and 0.46 g (0.5 mmol) Pd$_2$(dba)$_3$ were added and the mixture was stirred at 90° C. for 21 hours. The mixture was cooled to r.t., evaporated, diluted with 300 mL ethylacetate and three times extracted with water, the organic phase dried over sodium sulfate and evaporated. The resulting black oil was purified by liquid chromatography over silica gel with heptane/ethylacetate as eluent. Target fractions were combined and evaporated to yield 2.2 g (6.1 mmol, 48%) methyl 2-((6-isopropyl-2-oxo-1-phenyl-1,2-dihydropyridin-4-yl)amino)benzoate as a red oil.

d) 3-isopropyl-2-phenylbenzo[b][1,6]naphthyridine-1,10(2H,5H)-dione 2.2 g (6.1 mmol) methyl 2-((6-isopropyl-2-oxo-1-phenyl-1,2-dihydropyridin-4-yl)amino)benzoate were dissolved in 24 mL polyphosphoric acid and heated to 125° C. for 5 hours. The reaction mixture was cooled to r.t., hydrolyzed by slow addition of 500 mL water and adjusted to pH 8 by careful addition of solid potassium bicarbonate. The resulting suspension was extracted with 80 mL DCM, the organic phase twice extracted with 80 mL water and brine, the combined aqueous phases twice with 80 mL DCM. Combined aqueous phases were filtered and the remaining solid dried under reduced pressure to yield 1.1 g (3.3 mmol, 55%) 3-isopropyl-2-phenylbenzo[b][1,6]naphthyridine-1,10(2H,5H)-dione as a n off-white solid.

ESI-MS [M+H]$^+$ 331.2; LCMS Rt [min], meth. A: 0.60.

$^1$H-NMR (400 MHz, d$_6$-DMSO): δ (ppm)=11.74 (s, 1H), 8.10 (dd, J=8.1, 1.5 Hz, 1H), 7.67 (td, J=7.7, 7.1, 1.6 Hz, 1H), 7.60-7.43 (m, 4H), 7.35-7.26 (m, 3H), 6.24 (s, 1H), 2.41 (sep, J=6.8 Hz, 1H), 1.10 (d, J=6.7 Hz, 6H).

Example 1.4: 3-isopropyl-5-methyl-2-phenylbenzo[b][1,6]naphthyridine-1,10(2H,5H)-dione

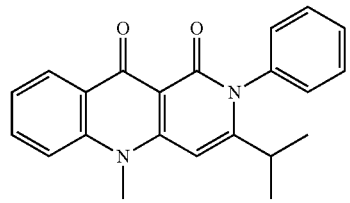 [SMILES: CC(C)c1cc2c(c(=O)c3ccccc3n2C)c(=O)n1-c1ccccc1]

To a solution of 630 mg (1.9 mmol) 3-isopropyl-2-phenylbenzo[b][1,6]naphthyridine-1,10(2H,5H)-dione in 34 mL DMF 1.86 g caesium carbonate (5.7 mmol) and 0.81 g methyl iodide (5.7 mmol) were added at stirred for 1 hour at r.t. Then 80 mL water and 80 mL DCM were added, the organic phase extracted twice water and brine, combined aqueous phases were extracted twice with DCM, combined organic phases were dried over sodium sulfate, and evaporated. The resulting residue was suspended in 5 mL DCM, filtered, the filtrate evaporated, suspended in 5 mL diethyl ether, filtered, and combined solids dried under reduced pressure to yield 441 mg (1.3 mmol, 67%) 3-isopropyl-5-methyl-2-phenylbenzo[b][1,6]naphthyridine-1,10(2H,5H)-dione as an off-white solid.

ESI-MS [M+H]$^+$ 345.3; LCMS Rt [min], meth. A: 0.61.

$^1$H-NMR (400 MHz, d$_6$-DMSO): δ (ppm)=8.20 (dd, J=7.9, 1.6 Hz, 1H), 7.86-7.71 (m, 2H), 7.61-7.46 (m, 3H), 7.42-7.28 (m, 3H), 6.53 (s, 1H), 3.90 (s, 3H), 2.48-2.41 (m, 1H), 1.18 (d, J=6.8 Hz, 6H).

The following examples can be made in a manner analogous to examples 1.1 to 1.4:

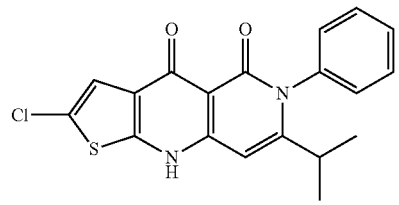

2-chloro-7-isopropyl-6-phenylthieno[2,3-b][1,6]naphthyridine-4,5(6H,9H)-dione

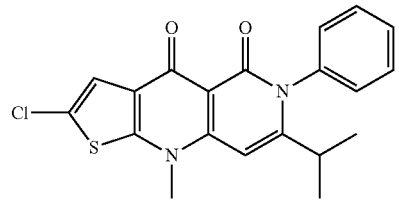

2-chloro-7-isopropyl-9-methyl-6-phenylthieno[2,3-b][1,6]naphthyridine-4,5(6H,9H)-dione

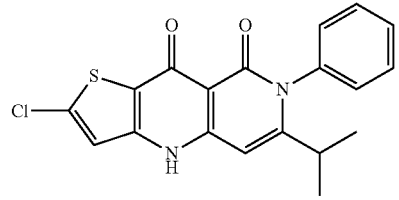

2-chloro-6-isopropyl-7-phenylthieno[3,2-b][1,6]naphthyridine-8,9(4H,7H)-dione

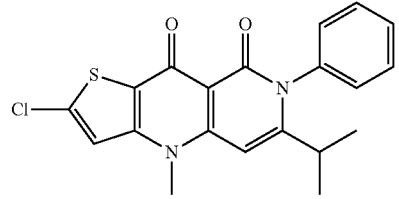

2-chloro-6-isopropyl-4-methyl-7-phenylthieno[3,2-b][1,6]naphthyridine-8,9(4H,7H)-dione

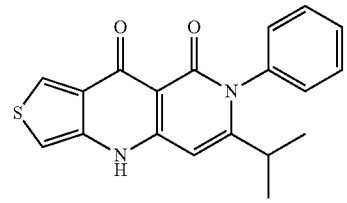

6-isopropyl-7-phenylthieno[3,4-b][1,6]naphthyridine-8,9(4H,7H)-dione

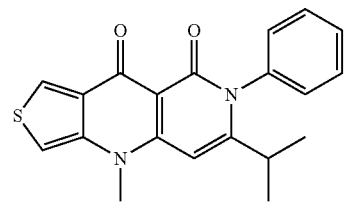

6-isopropyl-4-methyl-7-phenylthieno[3,4-b][1,6]naphthyridine-8,9(4H,7H)-dione

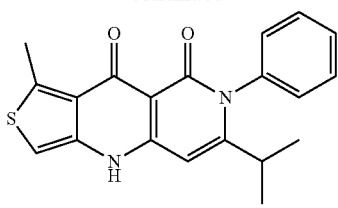

6-isopropyl-1-methyl-7-phenylthieno[3,4-b][1,6]naphthyridine-8,9(4H,7H)-dione

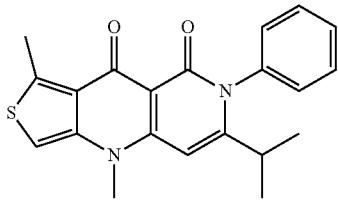

6-isopropyl-1,4-dimethyl-7-phenylthieno[3,4-b][1,6]naphthyridine-8,9(4H,7H)-dione

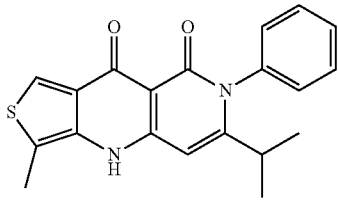

6-isopropyl-3-methyl-7-phenylthieno[3,4-b][1,6]naphthyridine-8,9(4H,7H)-dione

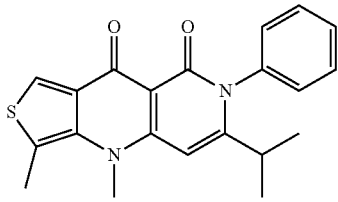

6-isopropyl-3,4-dimethyl-7-phenylthieno[3,4-b][1,6]naphthyridine-8,9(4H,7H)-dione

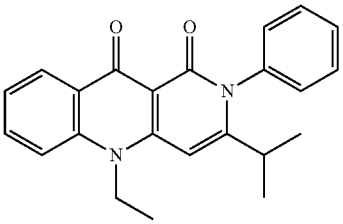

5-ethyl-3-isopropyl-2-phenylbenzo[b][1,6]naphthyridine-1,10(2H,5H)-dione

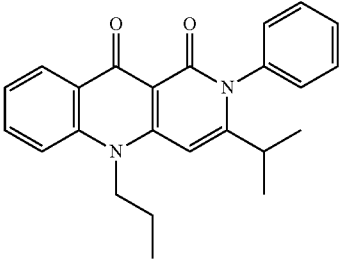

3-isopropyl-2-phenyl-5-propylbenzo[b][1,6]naphthyridine-1,10(2H,5H)-dione

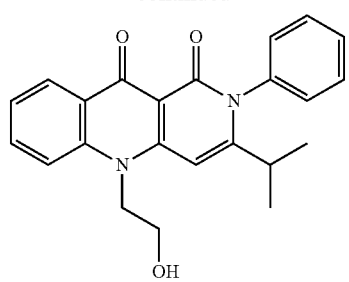

5-(2-hydroxyethyl)-3-isopropyl-2-phenylbenzo[b][1,6]naphthyridine-1,10(2H,5H)-dione

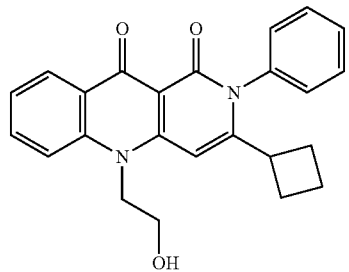

3-cyclobutyl-5-(2-hydroxyethyl)-2-phenylbenzo[b][1,6]naphthyridine-1,10(2H,5H)-dione

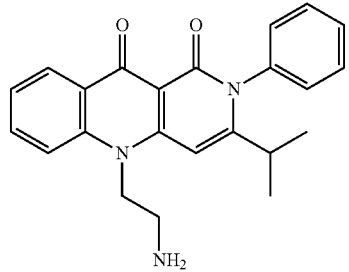

5-(2-aminoethyl)-3-isopropyl-2-phenylbenzo[b][1,6]naphthyridine-1,10(2H,5H)-dione

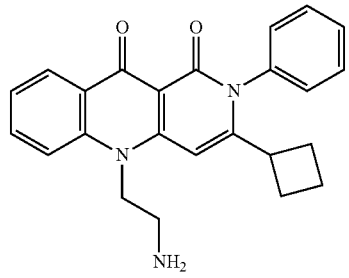

5-(2-aminoethyl)-3-cyclobutyl-2-phenylbenzo[b][1,6]naphthyridine-1,10(2H,5H)-dione

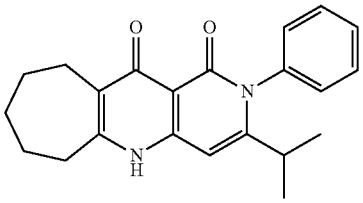

3-isopropyl-2-phenyl-5,6,7,8,9,10-hexahydro-1H-cyclohepta[b][1,6]naphthyridine-1,11(2H)-dione

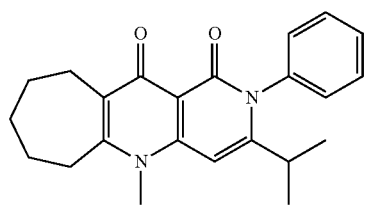

3-isopropyl-5-methyl-2-phenyl-
5,6,7,8,9,10-hexahydro-1H-
cyclohepta[b][1,6]naphthyridine-
1,11(2H)-dione

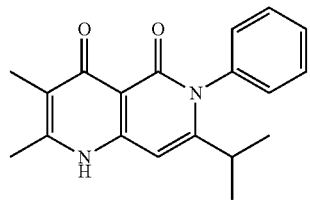

7-isopropyl-2,3-dimethyl-6-phenyl-1,6-
naphthyridine-4,5(1H,6H)-dione

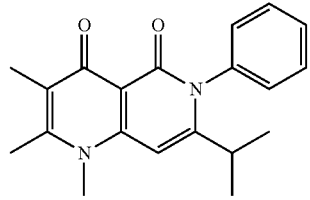

7-isopropyl-1,2,3-
trimethyl-6-phenyl-1,6-
naphthyridine-4,5(1H,6H)-dione

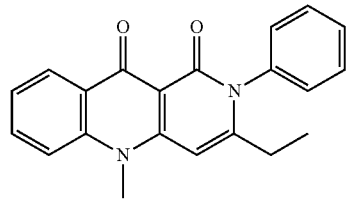

3-ethyl-5-methyl-2-
phenylbenzo[b][1,6]naphthyridine-
1,10(2H,5H)-dione

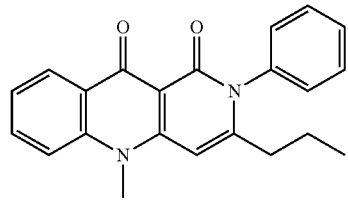

5-methyl-2-phenyl-3-
propylbenzo[b][1,6]naphthyridine-
1,10(2H,5H)-dione

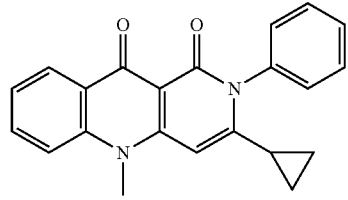

3-cyclopropyl-5-methyl-2-
phenylbenzo[b][1,6]naphthyridine-
1,10(2H,5H)-dione

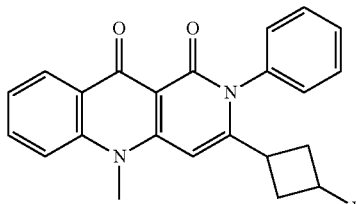

3-(3-fluorocyclobutyl)-5-methyl-2-
phenylbenzo[b][1,6]naphthyridine-
1,10(2H,5H)-dione

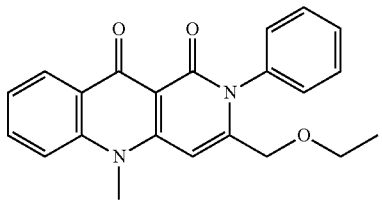

3-(ethoxymethyl)-5-methyl-2-
phenylbenzo[b][1,6]naphthyridine-
1,10(2H,5H)-dione

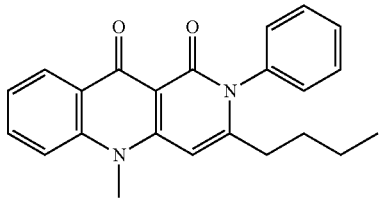

3-butyl-5-methyl-2-
phenylbenzo[b][1,6]naphthyridine-
1,10(2H,5H)-dione

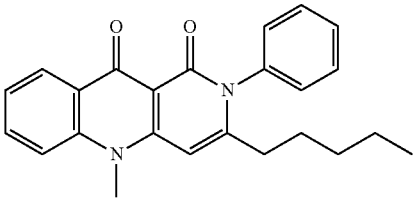

5-methyl-3-pentyl-2-
phenylbenzo[b][1,6]naphthyridine-
1,10(2H,5H)-dione

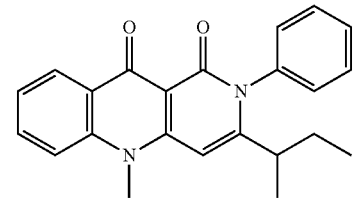

3-(sec-butyl)-5-methyl-2-
phenylbenzo[b][1,6]naphthyridine-
1,10(2H,5H)-dione

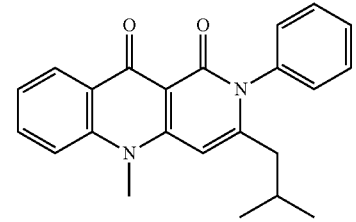

3-isobutyl-5-methyl-2-
phenylbenzo[b][1,6]naphthyridine-
1,10(2H,5H)-dione

-continued

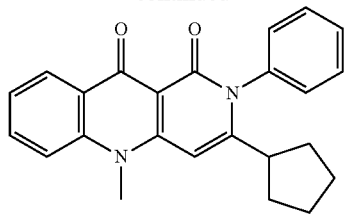

3-cyclopentyl-5-methyl-2-
phenylbenzo[b][1,6]naphthyridine-
1,10(2H,5H)-dione

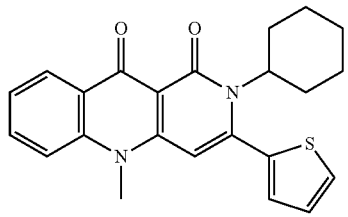

2-cyclohexyl-5-methyl-3-(thiophen-2-
yl)benzo[b][1,6]naphthyridine-
1,10(2H,5H)-dione*

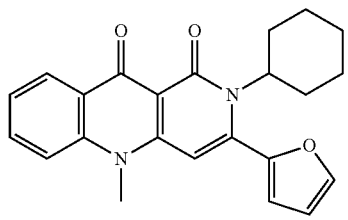

2-cyclohexyl-3-(furan-2-yl)-5-
methylbenzo[b][1,6]naphthyridine-
1,10(2H,5H)-dione*

-continued

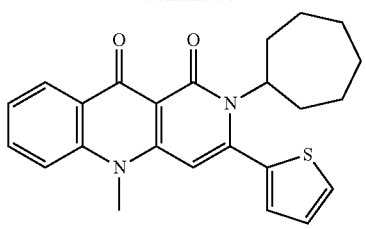

2-cycloheptyl-5-methyl-3-(thiophen-2-
yl)benzo[b][1,6]naphthyridine-
1,10(2H(5H)-dione*

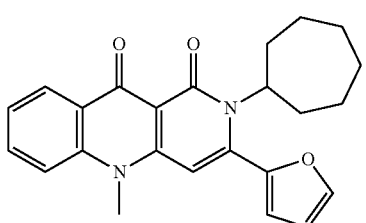

2-cycloheptyl-3-(furan-2-yl)-5-
methylbenzo[b][1,6]naphthyridine-
1,10(2H,5H)-dione*

*: compounds which can be made in a manner analogous to examples 1.1 and 2.1

The following examples were made in a manner analogous to examples 1.1 to 1.4.

| Ex | Structure | Name | LCMS Rt [min], meth. A | [M + H]⁺ |
| --- | --- | --- | --- | --- |
| 1.5 | 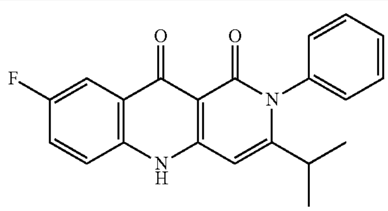 [SMILES: CC(C)c1cc2[nH]c3ccc(F)cc3c(=O)c2c(=O)n1-c1ccccc1] | 8-fluoro-3-isopropyl-2-phenylbenzo[b][1,6]naphthyridine-1,10(2H,5H)-dione | 0.67 | 349.1 |
| 1.6 | 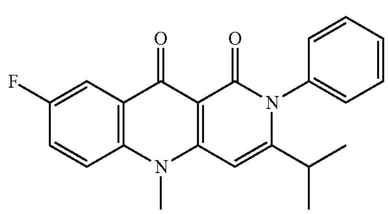 [SMILES: CC(C)c1cc2c(c(=O)c3cc(F)ccc3n2C)c(=O)n1-c1ccccc1] | 8-fluoro-3-isopropyl-5-methyl-2-phenylbenzo[b][1,6]naphthyridine-1,10(2H,5H)-dione | 0.59 | 363.2 |
| 1.7 | 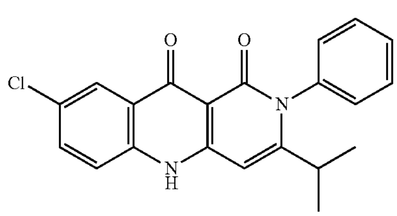 [SMILES: CC(C)c1cc2[nH]c3ccc(Cl)cc3c(=O)c2c(=O)n1-c1ccccc1] | 8-chloro-3-isopropyl-2-phenylbenzo[b][1,6]naphthyridine-1,10(2H,5H)-dione | 0.61 | 365.1 |

-continued

| Ex | Structure | Name | LCMS Rt [min], meth. A | [M + H]+ |
|---|---|---|---|---|
| 1.8 | 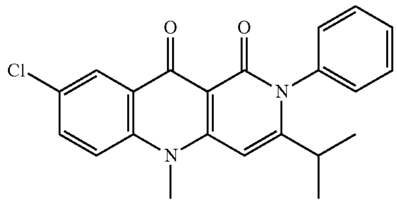 [SMILES: CC(C)c1cc2c(c(=O)c3cc(Cl)ccc3n2C)c(=O)n1-c1ccccc1] | 8-chloro-3-isopropyl-5-methyl-2-phenylbenzo[b][1,6]naphthyridine-1,10(2H,5H)-dione | 0.61 | 379.1 |
| 1.9 | 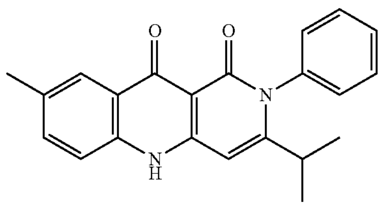 [SMILES: Cc1ccc2[nH]c3cc(C(C)C)n(-c4ccccc4)c(=O)c3c(=O)c2c1] | 3-isopropyl-8-methyl-2-phenylbenzo[b][1,6]naphthyridine-1,10(2H,5H)-dione | 0.60 | 345.2 |
| 1.10 | 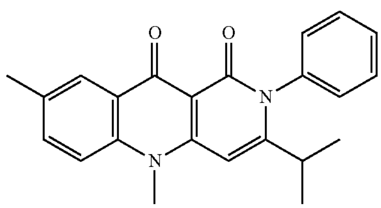 [SMILES: Cc1ccc2c(c1)c(=O)c1c(=O)n(-c3ccccc3)c(C(C)C)cc1n2C] | 3-isopropyl-5,8-dimethyl-2-phenylbenzo[b][1,6]naphthyridine-1,10(2H,5H)-dione | 0.60 | 359.2 |
| 1.11 | 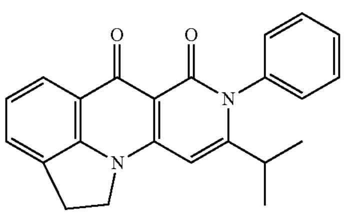 [SMILES: CC(C)c1cc2c(c(=O)c3cccc4c3n2CC4)c(=O)n1-c1ccccc1] | 9-isopropyl-8-phenyl-1H-indolo[1,7-ab][1,6]naphthyridine-6,7(2H,8H)-dione | 0.59 | 357.2 |
| 1.12 | 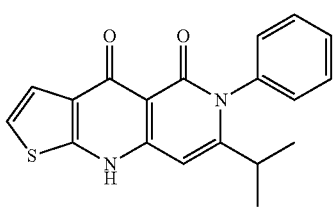 [SMILES: CC(C)c1cc2[nH]c3sccc3c(=O)c2c(=O)n1-c1ccccc1] | 7-isopropyl-6-phenylthieno[2,3-b][1,6]naphthyridine-4,5(6H,9H)-dione | 0.67 | 337.2 |
| 1.13 | 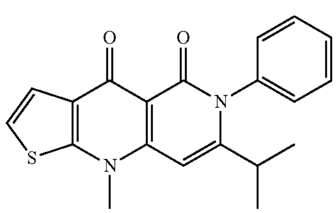 [SMILES: CC(C)c1cc2c(c(=O)c3ccsc3n2C)c(=O)n1-c1ccccc1] | 7-isopropyl-9-methyl-6-phenylthieno[2,3-b][1,6]naphthyridine-4,5(6H,9H)-dione | 0.56 | 351.1 |
| 1.14 | 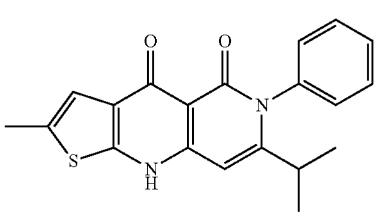 [SMILES: Cc1cc2c(=O)c3c(=O)n(-c4ccccc4)c(C(C)C)cc3[nH]c2s1] | 7-isopropyl-2-methyl-6-phenylthieno[2,3-b][1,6]naphthyridine-4,5(6H,9H)-dione | 0.68 | 351.2 |

-continued

| Ex | Structure | Name | LCMS Rt [min], meth. A | [M + H]+ |
|---|---|---|---|---|
| 1.15 | 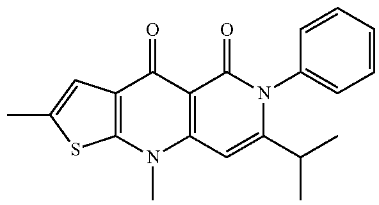 [SMILES: Cc1cc2c(=O)c3c(=O)n(-c4ccccc4)c(C(C)C)cc3n(C)c2s1] | 7-isopropyl-2,9-dimethyl-6-phenylthieno[2,3-b][1,6]naphthyridine-4,5(6H,9H)-dione | 0.56 | 365.1 |
| 1.16 | 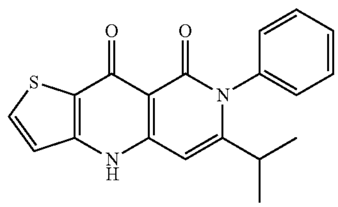 [SMILES: CC(C)c1cc2[nH]c3ccsc3c(=O)c2c(=O)n1-c1ccccc1] | 6-isopropyl-7-phenylthieno[3,2-b][1,6]naphthyridine-8,9(4H,7H)-dione | 0.59 | 337.1 |
| 1.17 | 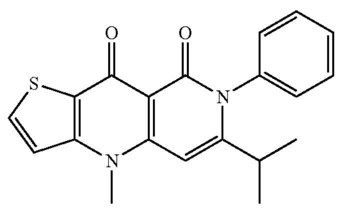 [SMILES: CC(C)c1cc2c(c(=O)c3sccc3n2C)c(=O)n1-c1ccccc1] | 6-isopropyl-4-methyl-7-phenylthieno[3,2-b][1,6]naphthyridine-8,9(4H,7H)-dione | 0.56 | 351.1 |
| 1.18 | 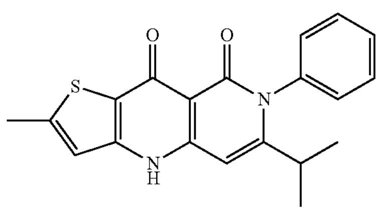 [SMILES: Cc1cc2[nH]c3cc(C(C)C)n(-c4ccccc4)c(=O)c3c(=O)c2s1] | 6-isopropyl-2-methyl-7-phenylthieno[3,2-b][1,6]naphthyridine-8,9(4H,7H)-dione | 0.62 | 351.1 |
| 1.19 | 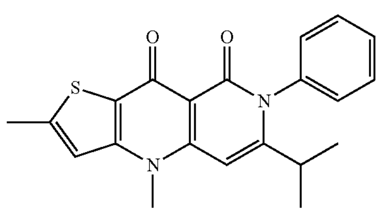 [SMILES: Cc1cc2c(s1)c(=O)c1c(=O)n(-c3ccccc3)c(C(C)C)cc1n2C] | 6-isopropyl-2,4-dimethyl-7-phenylthieno[3,2-b][1,6]naphthyridine-8,9(4H,7H)-dione | 0.57 | 365.1 |
| 1.20 | 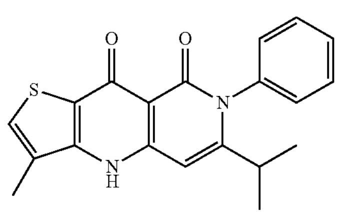 [SMILES: Cc1csc2c(=O)c3c(=O)n(-c4ccccc4)c(C(C)C)cc3[nH]c12] | 6-isopropyl-3-methyl-7-phenylthieno[3,2-b][1,6]naphthyridine-8,9(4H,7H)-dione | 0.62 | 351.1 |
| 1.21 | 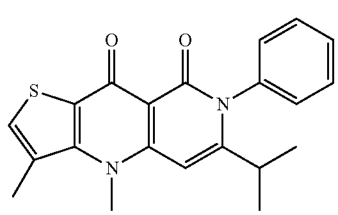 [SMILES: Cc1csc2c(=O)c3c(=O)n(-c4ccccc4)c(C(C)C)cc3n(C)c12] | 6-isopropyl-3,4-dimethyl-7-phenylthieno[3,2-b][1,6]naphthyridine-8,9(4H,7H)-dione | 0.57 | 365.2 |

| Ex | Structure | Name | LCMS Rt [min], meth. A | [M + H]+ |
|---|---|---|---|---|
| 1.22 | 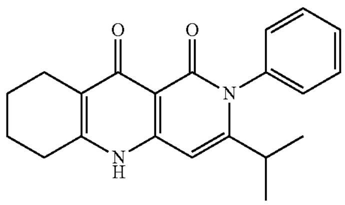 [SMILES: CC(C)c1cc2[nH]c3c(c(=O)c2c(=O)n1-c1ccccc1)CCCC3] | 3-isopropyl-2-phenyl-6,7,8,9-tetrahydrobenzo[b][1,6]naphthyridine-1,10(2H,5H)-dione | 0.56 | 335.2 |
| 1.23 | 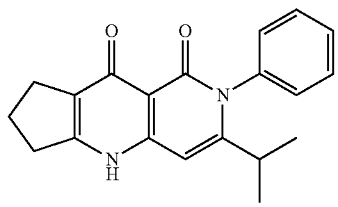 [SMILES: CC(C)c1cc2[nH]c3c(c(=O)c2c(=O)n1-c1ccccc1)CCC3] | 3-isopropyl-2-phenyl-5,6,7,8-tetrahydro-1H-cyclopenta[b][1,6]naphthyridine-1,9(2H)-dione | 0.59 | 321.2 |
| 1.24 | 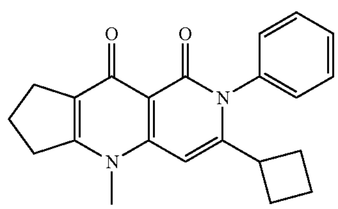 [SMILES: Cn1c2c(c(=O)c3c(=O)n(-c4ccccc4)c(C4CCC4)cc31)CCC2] | 3-cyclobutyl-5-methyl-2-phenyl-5,6,7,8-tetrahydro-1H-cyclopenta[b][1,6]naphthyridine-1,9(2H)-dione | 0.50 | 347.3 |
| 1.25 | 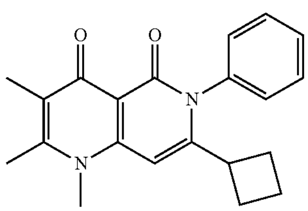 [SMILES: Cc1c(C)n(C)c2cc(C3CCC3)n(-c3ccccc3)c(=O)c2c1=O] | 7-cyclobutyl-1,2,3-trimethyl-6-phenyl-1,6-naphthyridine-4,5(1H,6H)-dione | 0.49 | 335.3 |
| 1.26 | 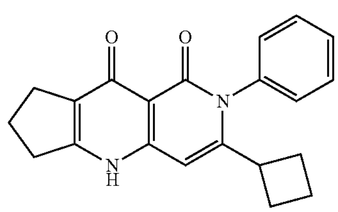 [SMILES: O=c1c2c([nH]c3cc(C4CCC4)n(-c4ccccc4)c(=O)c13)CCC2] | 3-cyclobutyl-2-phenyl-5,6,7,8-tetrahydro-1H-cyclopenta[b][1,6]naphthyridine-1,9(2H)-dione | 0.60 | 333.2 |
| 1.27 | 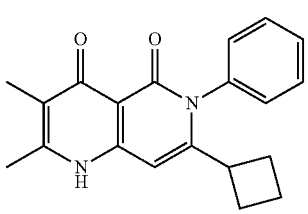 [SMILES: Cc1[nH]c2cc(C3CCC3)n(-c3ccccc3)c(=O)c2c(=O)c1C] | 7-cyclobutyl-2,3-dimethyl-6-phenyl-1,6-naphthyridine-4,5(1H,6H)-dione | 0.54 | 321.3 |
| 1.28 | 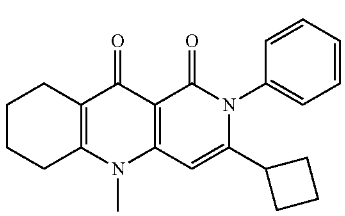 [SMILES: Cn1c2c(c(=O)c3c(=O)n(-c4ccccc4)c(C4CCC4)cc31)CCCC2] | 3-cyclobutyl-5-methyl-2-phenyl-6,7,8,9-tetrahydrobenzo[b][1,6]naphthyridine-1,10(2H,5H)-dione | 0.53 | 361.2 |

-continued

| Ex | Structure | Name | LCMS Rt [min], meth. A | [M + H]+ |
|---|---|---|---|---|
| 1.29 | 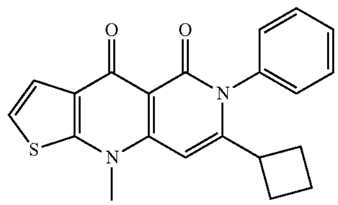 [SMILES: Cn1c2cc(C3CCC3)n(-c3ccccc3)c(=O)c2c(=O)c2ccsc21] | 7-cyclobutyl-9-methyl-6-phenylthieno[2,3-b][1,6]naphthyridine-4,5(6H,9H)-dione | 0.58 | 363.1 |
| 1.30 | 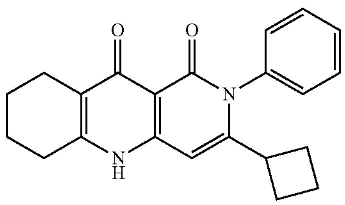 [SMILES: O=c1c2c([nH]c3cc(C4CCC4)n(-c4ccccc4)c(=O)c13)CCCC2] | 3-cyclobutyl-2-phenyl-6,7,8,9-tetrahydrobenzo[b][1,6]naphthyridine-1,10(2H,5H)-dione | 0.56 | 347.2 |
| 1.31 | 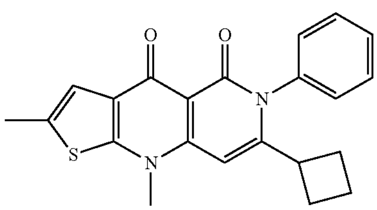 [SMILES: Cc1cc2c(=O)c3c(=O)n(-c4ccccc4)c(C4CCC4)cc3n(C)c2s1] | 7-cyclobutyl-2,9-dimethyl-6-phenylthieno[2,3-b][1,6]naphthyridine-4,5(6H,9H)-dione | 0.59 | 377.3 |
| 1.32 | 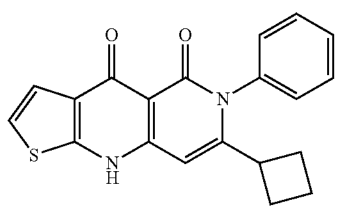 [SMILES: O=c1c2ccsc2[nH]c2cc(C3CCC3)n(-c3ccccc3)c(=O)c12] | 7-cyclobutyl-6-phenylthieno[2,3-b][1,6]naphthyridine-4,5(6H,9H)-dione | 0.68 | 349.1 |
| 1.33 | 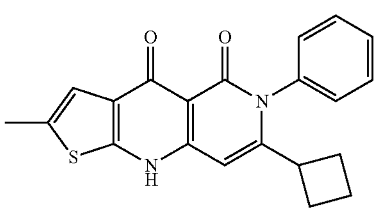 [SMILES: Cc1cc2c(=O)c3c(=O)n(-c4ccccc4)c(C4CCC4)cc3[nH]c2s1] | 7-cyclobutyl-2-methyl-6-phenylthieno[2,3-b][1,6]naphthyridine-4,5(6H,9H)-dione | 0.70 | 363.1 |
| 1.34 | 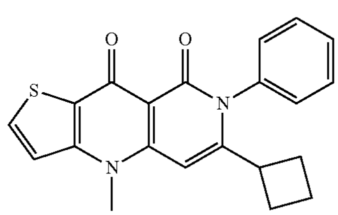 [SMILES: Cn1c2ccsc2c(=O)c2c(=O)n(-c3ccccc3)c(C3CCC3)cc21] | 6-cyclobutyl-4-methyl-7-phenylthieno[3,2-b][1,6]naphthyridine-8,9(4H,7H)-dione | 0.58 | 363.4 |
| 1.35 | 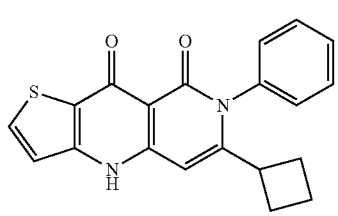 [SMILES: O=c1c2sccc2[nH]c2cc(C3CCC3)n(-c3ccccc3)c(=O)c12] | 6-cyclobutyl-7-phenylthieno[3,2-b][1,6]naphthyridine-8,9(4H,7H)-dione | 0.61 | 349.1 |

| Ex | Structure | Name | LCMS Rt [min], meth. A | [M + H]+ |
|---|---|---|---|---|
| 1.36 | 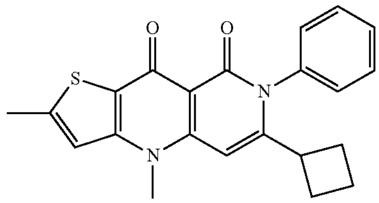 [SMILES: Cc1cc2c(s1)c(=O)c1c(=O)n(-c3ccccc3)c(C3CCC3)cc1n2C] | 6-cyclobutyl-2,4-dimethyl-7-phenylthieno[3,2-b][1,6]naphthyridine-8,9(4H,7H)-dione | 0.59 | 377.2 |
| 1.37 | 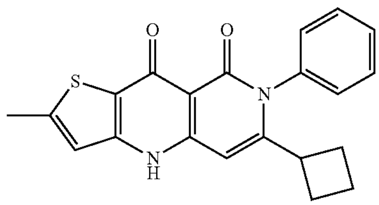 [SMILES: Cc1cc2[nH]c3cc(C4CCC4)n(-c4ccccc4)c(=O)c3c(=O)c2s1] | 6-cyclobutyl-2-methyl-7-phenylthieno[3,2-b][1,6]naphthyridine-8,9(4H,7H)-dione | 0.62 | 363.1 |
| 1.38 | 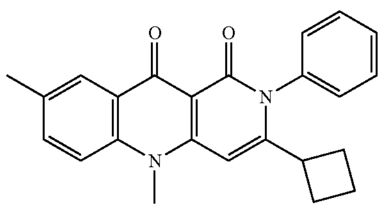 [SMILES: Cc1ccc2c(c1)c(=O)c1c(=O)n(-c3ccccc3)c(C3CCC3)cc1n2C] | 3-cyclobutyl-5,8-dimethyl-2-phenylbenzo[b][1,6]naphthyridine-1,10(2H,5H)-dione | 0.62 | 371.3 |
| 1.39 | 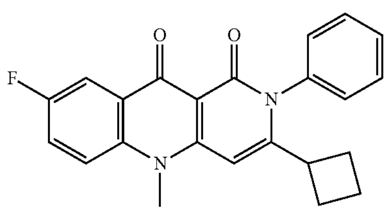 [SMILES: Cn1c2ccc(F)cc2c(=O)c2c(=O)n(-c3ccccc3)c(C3CCC3)cc21] | 3-cyclobutyl-8-fluoro-5-methyl-2-phenylbenzo[b][1,6]naphthyridine-1,10(2H,5H)-dione | 0.60 | 375.2 |
| 1.40 | 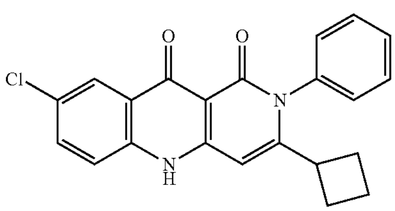 [SMILES: O=c1c2cc(Cl)ccc2[nH]c2cc(C3CCC3)n(-c3ccccc3)c(=O)c12] | 8-chloro-3-cyclobutyl-2-phenylbenzo[b][1,6]naphthyridine-1,10(2H,5H)-dione | 0.63 | 377.1 |
| 1.41 | 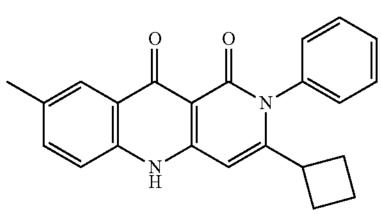 | 3-cyclobutyl-8-methyl-2-phenylbenzo[b][1,6]naphthyridine-1,10(2H,5H)-dione | 0.62 | 357.2 |
| 1.42 | 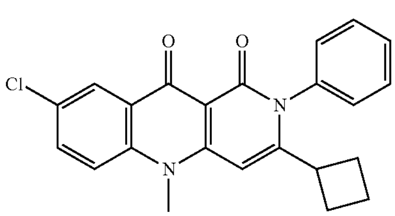 [SMILES: Cn1c2ccc(Cl)cc2c(=O)c2c(=O)n(-c3ccccc3)c(C3CCC3)cc21] | 8-chloro-3-cyclobutyl-5-methyl-2-phenylbenzo[b][1,6]naphthyridine-1,10(2H,5H)-dione | 0.63 | 391.2 |

-continued

| Ex | Structure | Name | LCMS Rt [min], meth. A | [M + H]+ |
|---|---|---|---|---|
| 1.43 | 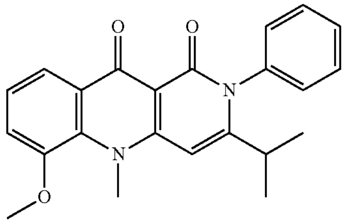 [SMILES: COc1cccc2c(=O)c3c(=O)n(-c4ccccc4)c(C(C)C)cc3n(C)c12] | 3-isopropyl-6-methoxy-5-methyl-2-phenylbenzo[b][1,6]naphthyridine-1,10(2H,5H)-dione | 0.61 | 375.2 |
| 1.44 | 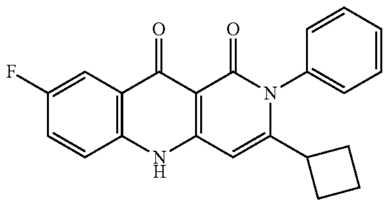 [SMILES: O=c1c2cc(F)ccc2[nH]c2cc(C3CCC3)n(-c3ccccc3)c(=O)c12] | 3-cyclobutyl-8-fluoro-2-phenylbenzo[b][1,6]naphthyridine-1,10(2H,5H)-dione | 0.62 | 361.1 |
| 1.45 | 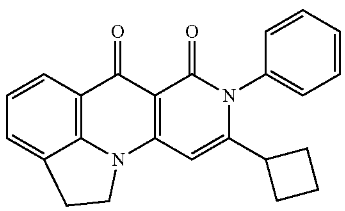 [SMILES: O=c1c2cccc3c2n(c2cc(C4CCC4)n(-c4ccccc4)c(=O)c12)CC3] | 9-cyclobutyl-8-phenyl-1H-indolo[1,7-ab][1,6]naphthyridine-6,7(2H,8H)-dione | 0.63 | 369.1 |
| 1.46 | 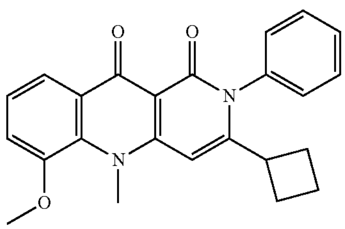 [SMILES: COc1cccc2c(=O)c3c(=O)n(-c4ccccc4)c(C4CCC4)cc3n(C)c12] | 3-cyclobutyl-6-methoxy-5-methyl-2-phenylbenzo[b][1,6]naphthyridine-1,10(2H,5H)-dione | 0.66 | 387.1 |
| 1.47 | 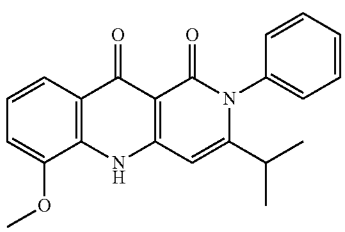 [SMILES: COc1cccc2c(=O)c3c(=O)n(-c4ccccc4)c(C(C)C)cc3[nH]c12] | 3-isopropyl-6-methoxy-2-phenylbenzo[b][1,6]naphthyridine-1,10(2H,5H)-dione | 0.61 | 361.2 |
| 1.48 | 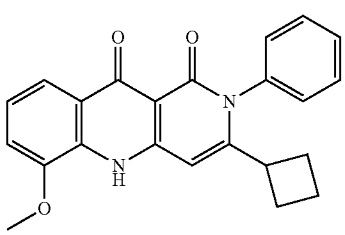 [SMILES: COc1cccc2c(=O)c3c(=O)n(-c4ccccc4)c(C4CCC4)cc3[nH]c12] | 3-cyclobutyl-6-methoxy-2-phenylbenzo[b][1,6]naphthyridine-1,10(2H,5H)-dione | 0.64 | 373.1 |
| 1.49 | 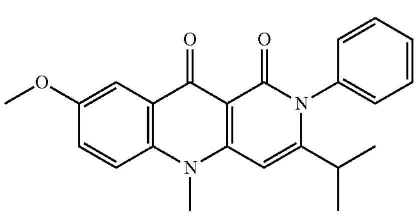 [SMILES: COc1ccc2c(c1)c(=O)c1c(=O)n(-c3ccccc3)c(C(C)C)cc1n2C] | 3-isopropyl-8-methoxy-5-methyl-2-phenylbenzo[b][1,6]naphthyridine-1,10(2H(5H)-dione | 0.63 | 375.2 |

-continued

| Ex | Structure | Name | LCMS Rt [min], meth. A | [M + H]+ |
|---|---|---|---|---|
| 1.50 | 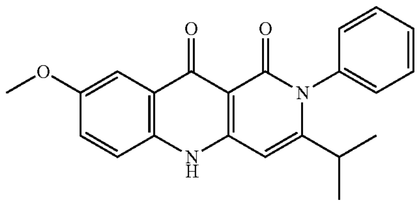 [SMILES: COc1ccc2[nH]c3cc(C(C)C)n(-c4ccccc4)c(=O)c3c(=O)c2c1] | 3-isopropyl-8-methoxy-2-phenylbenzo[b][1,6]naphthyridine-1,10(2H,5H)-dione | 0.63 | 361.1 |
| 1.51 | 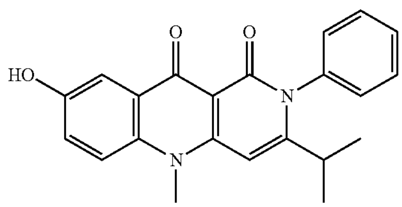 [SMILES: CC(C)c1cc2c(c(=O)c3cc(O)ccc3n2C)c(=O)n1-c1ccccc1] | 8-hydroxy-3-isopropyl-5-methyl-2-phenylbenzo[b][1,6]naphthyridine-1,10(2H,5H)-dione | 0.61 | 361.1 |
| 1.52 | 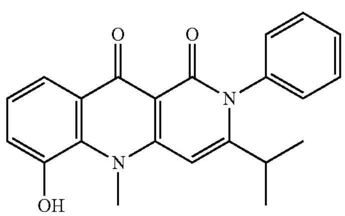 [SMILES: CC(C)c1cc2c(c(=O)c3cccc(O)c3n2C)c(=O)n1-c1ccccc1] | 6-hydroxy-3-isopropyl-5-methyl-2-phenylbenzo[b][1,6]naphthyridine-1,10(2H,5H)-dione | 0.63 | 361.1 |

Example 2.1: 3-cyclobutyl-2-cyclopentylbenzo[b][1,6]naphthyridine-1,10(2H,5H)-dione

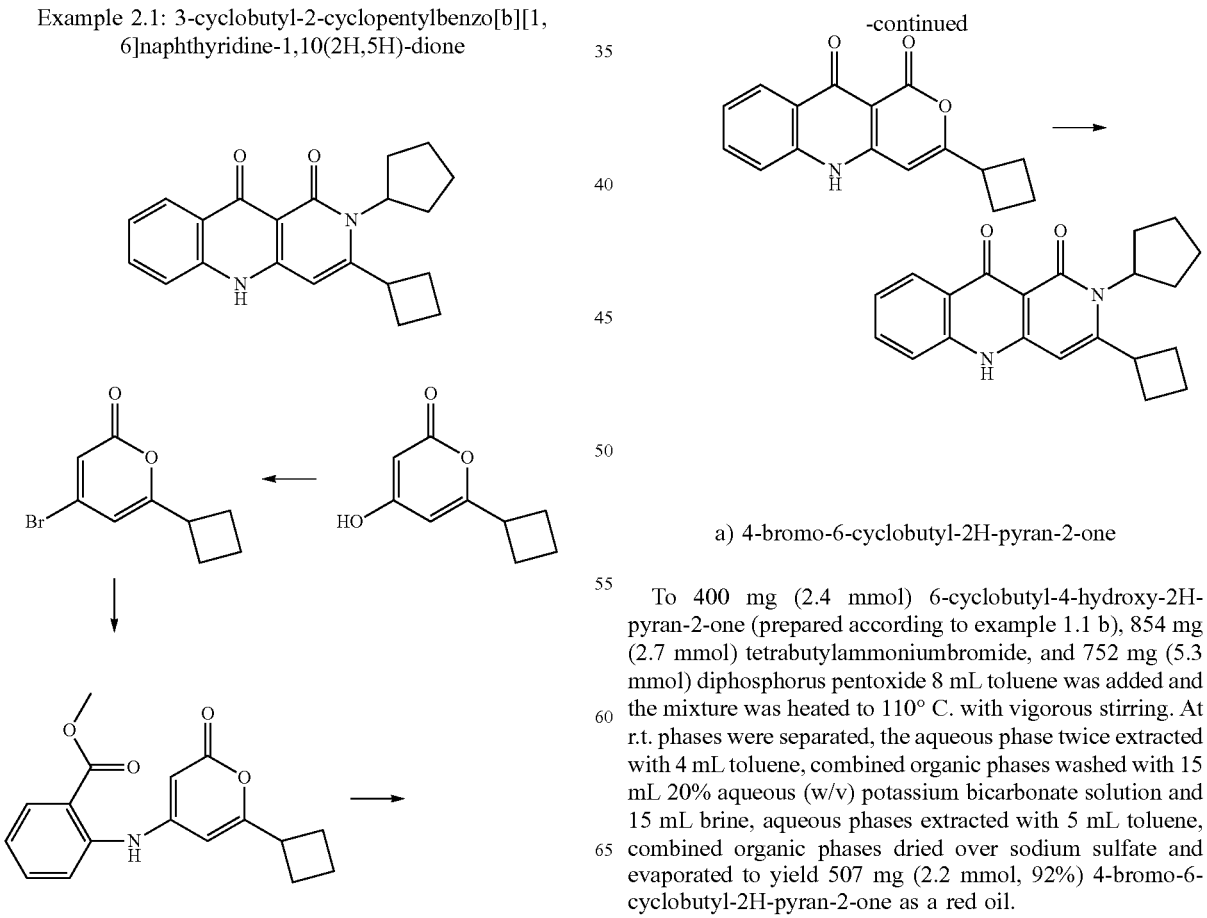

a) 4-bromo-6-cyclobutyl-2H-pyran-2-one

To 400 mg (2.4 mmol) 6-cyclobutyl-4-hydroxy-2H-pyran-2-one (prepared according to example 1.1 b), 854 mg (2.7 mmol) tetrabutylammoniumbromide, and 752 mg (5.3 mmol) diphosphorus pentoxide 8 mL toluene was added and the mixture was heated to 110° C. with vigorous stirring. At r.t. phases were separated, the aqueous phase twice extracted with 4 mL toluene, combined organic phases washed with 15 mL 20% aqueous (w/v) potassium bicarbonate solution and 15 mL brine, aqueous phases extracted with 5 mL toluene, combined organic phases dried over sodium sulfate and evaporated to yield 507 mg (2.2 mmol, 92%) 4-bromo-6-cyclobutyl-2H-pyran-2-one as a red oil.

b) Methyl 2-((6-cyclobutyl-2-oxo-2H-pyran-4-yl)amino)benzoate

Under argon 494 mg (2.2 mmol) 4-bromo-6-cyclobutyl-2H-pyran-2-one and 1054 mg (3.2 mmol) caesium carbonate were suspended in 8 mL toluene and subsequently 363 L (424 mg, 2.8 mmol) methyl 2-aminobenzoate, 16 mg (0.026 mmol) rac-BINAP, and 12 mg (0.013 mmol) $Pd_2(dba)_3$ were added. The mixture was heated to 110° C. for 23 hours. At r.t. the mixture was filtered through hyflo and the filtrate evaporated and purified by liquid chromatography over silica gel with cyclohexane/TBME as eluent. Target fractions were combined and evaporated to yield 458 mg (1.5 mmol, 71%) methyl 2-((6-cyclobutyl-2-oxo-2H-pyran-4-yl)amino)benzoate as a yellow solid.

c) 3-cyclobutyl-1H-pyrano[4,3-b]quinoline-1,10(5H)-dione

To 0.4 g (1.4 mmol) methyl 2-((6-cyclobutyl-2-oxo-2H-pyran-4-yl)amino)benzoate 5 g (1.4 mmol) polyphosphoric acid was added and heated to 130° C. for 45 minutes. The reaction mixture was hydrolyzed with 20 mL water not exceeding r.t., diluted with 40 mL water and neutralized to pH 7-8 by careful addition of solid potassium bicarbonate. The resulting solid was filtered, washed with water and dried to yield 360 mg (1.4 mmol, 98%) 3-cyclobutyl-1H-pyrano[4,3-b]quinoline-1,10(5H)-dione as off-white solid.

d) 3-cyclobutyl-2-cyclopentylbenzo[b][1,6]naphthyridine-1,10(2H,5H)-dione

To 329 mg (1.23 mmol) 3-cyclobutyl-1H-pyrano[4,3-b]quinoline-1,10(5H)-dione in 6.2 mL trifluoroethanol 850 μL (13.7 mmol) cyclopentylamine and 141 μL (5.5 mmol) acetic acid were added and heated to 90° C. for 7 hours. The mixture was evaporated, the residue twice mixed with 4 mL ethylether and filtered, washed twice with 7.5 mL isopropanol/diethylether 3:2 (v/v), with 7 mL diethylether and eight times thoroughly with water. The remaining solid was dried to yield 373 mg (1.1 mmol, 91%) 3-cyclobutyl-2-cyclopentylbenzo[b][1,6]naphthyridine-1,10(2H,5H)-dione as an off-white solid.

ESI-MS [M+H]$^+$ 335.1; LCMS Rt [min], meth. A: 0.66;
$^1$H-NMR (400 MHz, d$_6$-DMSO): δ (ppm)=11.58 (s, 1H), 8.09 (dd, J=8.0, 1.2 Hz, 1H), 7.64 (dt, 1H), 7.41 (dd, J=8.1 Hz, 1H), 7.27 (dt, J=7.5 Hz, 1H), 6.08 (s, 1H), 4.43 (p, 1H), 3.71 (p, 1H), 2.41-2.26 (m, 2H), 2.26-2.07 (m, 4H), 2.07-1.89 (m, 3H), 1.89-1.63 (m, 3H), 1.63-1.41 (m, 2H)

Example 2.2: 3-cyclobutyl-2-cyclopentyl-5-methyl-benzo[b][1,6]naphthyridine-1,10(2H,5H)-dione

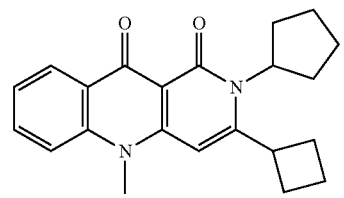 [SMILES: Cn1c2ccccc2c(=O)c2c(=O)n(C3CCCC3)c(C3CCC3)cc21]

Preparation according to example 1.2 starting with 129 mg (0.38 mmol) 3-cyclobutyl-2-cyclopentylbenzo[b][1,6]naphthyridine-1,10(2H,5H)-dione (example 2.1) to yield 121 mg (0.35, 90%) 3-cyclobutyl-2-cyclopentyl-5-methyl-benzo[b][1,6]naphthyridine-1,10(2H,5H)-dione as an off-white solid.

ESI-MS [M+H]$^+$ 349.2; LCMS Rt [min], meth. A: 0.70;
$^1$H-NMR (400 MHz, d$_6$-DMSO): δ (ppm)=8.20 (dd, J=7.9, 1.4 Hz, 1H), 7.78 (dd, J=8.3 Hz, 1H), 7.72 (dt, J=8.6, 1.6 Hz, 1H), 7.35 (dt, J=7.3 Hz, 1H), 6.23 (s, 1H), 4.49 (p, J=8.6 Hz, 1H), 3.76 (p, J=8.6 Hz, 1H), 2.45-2.33 (m, 2H), 2.33-2.25 (m, 2H), 2.20 (m, J=14.8, 7.4 Hz, 2H), 2.11-1.90 (m, 3H), 1.90-1.66 (m, 3H), 1.66-1.48 (m, 2H)

Example 2.3: 2-cyclopentyl-3-isopropylbenzo[b][1,6]naphthyridine-1,10(2H,5H)-dione

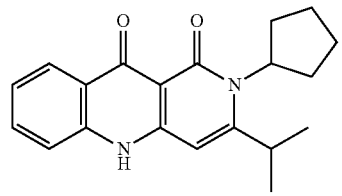 [SMILES: CC(C)c1cc2[nH]c3ccccc3c(=O)c2c(=O)n1C1CCCC1]

Preparation according to example 2.1 a) to d) using 243 mg (0.95 mmol) 3-isopropyl-1H-pyrano[4,3-b]quinoline-1,10(5H)-dione to yield 220 mg (0.68 mmol, 72%) 2-cyclopentyl-3-isopropylbenzo[b][1,6]naphthyridine-1,10(2H,5H)-dione as a white solid.

ESI-MS [M+H]$^+$ 323.2; LCMS Rt [min], meth. A: 0.64.
$^1$H-NMR (400 MHz, d$_6$-DMSO): δ (ppm)=11.55 (s, 1H), 8.09 (dd, J=7.9 Hz, 1H), 7.64 (dt, J=7.5 Hz, 1H), 7.41 (dd, J=8.1 Hz, 1H), 7.26 (dt, J=7.5 Hz, 1H), 6.13 (s, 1H), 4.74 (p, 1H), 3.24 (hept, J=6.5 Hz, 1H), 2.29-2.13 (m, 2H), 2.01 (m, 2H), 1.88-1.72 (m, 2H), 1.68-1.52 (m, 2H), 1.28 (m, J=6.5 Hz, 6H)

Example 2.4: 2-cyclopentyl-3-isopropyl-5-methyl-benzo[b][1,6]naphthyridine-1,10(2H,5H)-dione

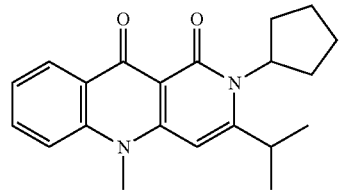 [SMILES: CC(C)c1cc2c(c(=O)c3ccccc3n2C)c(=O)n1C1CCCC1]

Preparation according to example 2.2 using 33 mg (0.1 mmol) 2-cyclopentyl-3-isopropylbenzo[b][1,6]naphthyridine-1,10(2H,5H)-dione to yield 26 mg (0.08 mmol, 76%) 2-cyclopentyl-3-isopropyl-5-methylbenzo[b][1,6]naphthyridine-1,10(2H,5H)-dione as off-white solid.

ESI-MS [M+H]$^+$ 337.1; LCMS Rt [min], meth. A: 0.64;
$^1$H-NMR (400 MHz, d$_6$-DMSO): δ (ppm)=8.20 (dd, 1H), 7.77 (dd, J=8.1 Hz, 1H), 7.73 (dt, 1H), 7.35 (dt, 1H), 6.33 (s, 1H), 4.80 (p, J=8.5 Hz, 1H), 3.82 (s, 3H), 3.30 (hept, 1H), 2.28-2.13 (m, 2H), 2.09-1.95 (m, 2H), 1.88-1.74 (m, 2H), 1.68-1.53 (m, 2H), 1.34 (m, J=6.7 Hz, 6H)

Example 2.5: 3-cyclobutyl-2-(pyridin-2-yl)benzo[b][1,6]naphthyridine-1,10(2H,5H)-dione

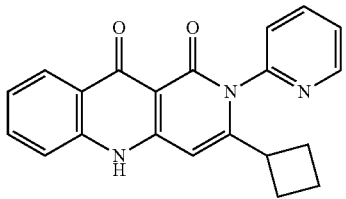 [SMILES: O=c1c2ccccc2[nH]c2cc(C3CCC3)n(-c3ccccn3)c(=O)c12]

Preparation according to example 2.1 reacting 219 mg (0.82 mmol) 3-cyclobutyl-1H-pyrano[4,3-b]quinoline-1,10(5H)-dione and 769 mg (8.2 mmol) 2-aminopyridine without solvent at 170° C. for 17 hours to yield 209 mg (0.61 mmol, 75%) 3-cyclobutyl-2-(pyridin-2-yl)benzo[b][1,6]naphthyridine-1,10(2H,5H)-dione as brownish solid.

ESI-MS [M+H]$^+$ 344.3; LCMS Rt [min], meth. A: 0.57; $^1$H-NMR (400 MHz, d$_6$-DMSO): δ (ppm)=11.82 (s, 1H), 8.68-8.58 (m, 1H), 8.11 (dd, 1H), 8.01 (dt, J=7.7, 1.9 Hz, 1H), 7.69 (dt, 1H), 7.53 (dd, J=6.7, 5.0 Hz, 1H), 7.50-7.42 (m, 2H), 7.32 (t, J=7.5 Hz, 1H), 6.22 (s, 1H), 3.22 (p, J=9.0 Hz, 1H), 2.14-1.41 (m, 6H)

Example 2.6: 3-cyclobutyl-5-methyl-2-(pyridin-2-yl)benzo[b][1,6]naphthyridine-1,10(2H,5H)-dione

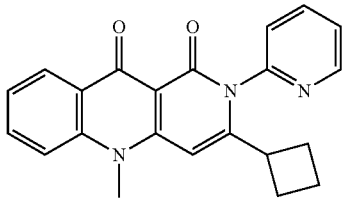 [SMILES: Cn1c2ccccc2c(=O)c2c(=O)n(-c3ccccn3)c(C3CCC3)cc21]

Preparation according to example 2.2 reacting 100 mg (0.29 mmol) 3-cyclobutyl-2-(pyridin-2-yl)benzo[b][1,6]naphthyridine-1,10(2H,5H)-dione to yield 68 mg (0.19 mmol, 66%) 3-cyclobutyl-5-methyl-2-(pyridin-2-yl)benzo[b][1,6]naphthyridine-1,10(2H,5H)-dione as ESI-MS [M+H]$^+$: 358.1; LCMS Rt [min], meth. A: 0.57; $^1$H-NMR (400 MHz, d$_6$-DMSO): δ (ppm)=8.64 (dd, 1H), 8.22 (dd, J=7.9, 1.4 Hz, 1H), 8.03 (dt, J=7.7, 1.8 Hz, 1H), 7.85 (d, J=8.6 Hz, 1H), 7.78 (dt, 1H), 7.55 (dd, J=7.1, 5.2 Hz, 1H), 7.47 (d, J=7.9 Hz, 1H), 7.40 (t, J=7.4 Hz, 1H), 6.43 (s, 1H), 3.93 (s, 3H), 3.25 (dt, J=17.3, 8.4 Hz, 1H), 2.15 (s, 2H), 1.78-1.47 (m, 4H).

Example 2.7: 3-cyclobutyl-2-(pyrrolidin-1-yl)benzo[b][1,6]naphthyridine-1,10(2H,5H)-dione

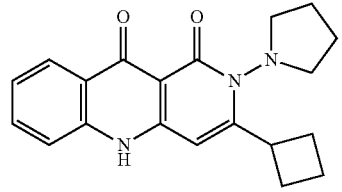

Preparation according to example 2.1 using 247 mg (0.92 mmol) 3-cyclobutyl-1H-pyrano[4,3-b]quinoline-1,10(5H)-dione and 588 mg (3.7 mmol) 1-aminopyrrolidine in 5 mL DMA at 170° C. for 12 hours to yield 255 mg (0.76 mmol, 82%) 3-cyclobutyl-2-(pyrrolidin-1-yl)benzo[b][1,6]naphthyridine-1,10(2H,5H)-dione as off-white solid.

ESI-MS [M+H]$^+$ 336.2; LCMS Rt [min], meth. A: 0.67 $^1$H-NMR (400 MHz, d$_6$-DMSO): δ (ppm)=11.67 (s, 1H), 8.10 (dd, 1H), 7.66 (dt, 1H), 7.43 (dd, J=8.1 Hz, 1H), 7.29 (dt, 1H), 6.05 (s, 1H), 3.70 (p, J=8.8 Hz, 1H), 3.48 (q, J=7.1, 6.7 Hz, 2H), 3.07 (q, 2H), 3.02-2.92 (m, 2H), 2.37-1.73 (m, 10H)

Example 2.8: 3-cyclobutyl-5-methyl-2-(pyrrolidin-1-yl)benzo[b][1,6]naphthyridine-1,10(2H,5H)-dione

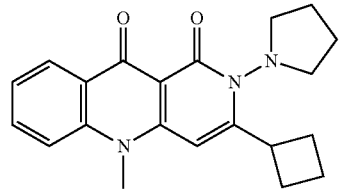 [SMILES: Cn1c2ccccc2c(=O)c2c(=O)n(N3CCCC3)c(C3CCC3)cc21]

Preparation according to example 2.2 reacting 124 mg (0.37 mmol) 3-cyclobutyl-2-(pyrrolidin-1-yl)benzo[b][1,6]naphthyridine-1,10(2H,5H)-dione to yield 72.3 mg (0.19 mmol, 52%) 3-cyclobutyl-5-methyl-2-(pyrrolidin-1-yl)benzo[b][1,6]naphthyridine-1,10(2H,5H)-dione as ESI-MS [M+H]$^+$ 350.1; LCMS Rt [min], meth. A: 0.67. $^1$H-NMR (400 MHz, d$_6$-DMSO): δ (ppm)=8.20 (dd, J=7.9, 1.4 Hz, 1H), 7.80 (dd, J=8.5 Hz, 1H), 7.74 (dt, 1H), 7.37 (dt, J=7.3 Hz, 1H), 6.22 (s, 1H), 3.85 (s, 3H), 3.77 (p, J=9.0 Hz, 1H), 3.49 (q, J=7.2 Hz, 2H), 2.98 (q, J=7.3 Hz, 2H), 2.37-1.74 (m, 10H).

The following examples were made in a manner analogous to examples 2.1 to 2.8.

| Ex | Structure | Name | LCMS Rt [min], meth. A | [M + H]$^+$ |
|---|---|---|---|---|
| 2.9 | 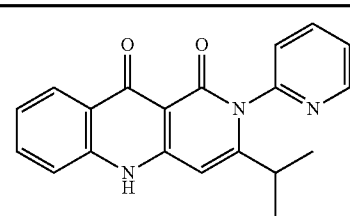 | 3-isopropyl-2-(pyridin-2-yl)benzo[b][1,6]naphthyridine-1,10(2H,5H)-dione | 0.56 | 332.1 |

-continued

| Ex | Structure | Name | LCMS Rt [min], meth. A | [M + H]+ |
|---|---|---|---|---|
| 2.10 | 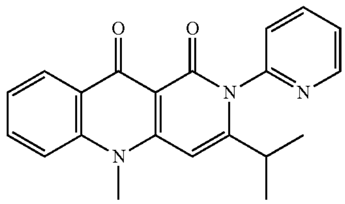 | 3-isopropyl-5-methyl-2-(pyridin-2-yl)benzo[b][1,6]naphthyridine-1,10(2H,5H)-dione | 0.56 | 346.1 |
| 2.11 | 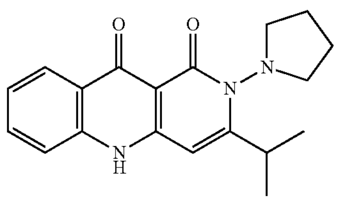 [SMILES: CC(C)c1cc2[nH]c3ccccc3c(=O)c2c(=O)n1N1CCCC1] | 3-isopropyl-2-(pyrrolidin-1-yl)benzo[b][1,6]naphthyridine-1,10(2H,5H)-dione | 0.66 | 324.1 |
| 2.12 | 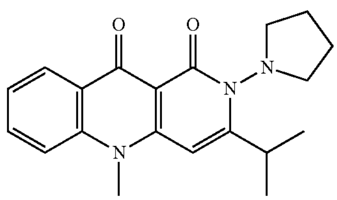 | 3-isopropyl-5-methyl-2-(pyrrolidin-1-yl)benzo[b][1,6]naphthyridine-1,10(2H,5H)-dione | 0.66 | 338.1 |
| 2.13 | 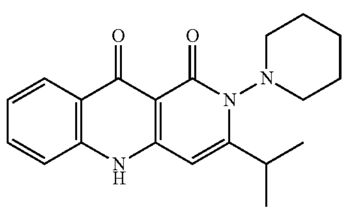 [SMILES: CC(C)c1cc2[nH]c3ccccc3c(=O)c2c(=O)n1N1CCCCC1] | 3-isopropyl-2-(piperidin-1-yl)benzo[b][1,6]naphthyridine-1,10(2H,5H)-dione | 0.73 | 338.2 |
| 2.14 | 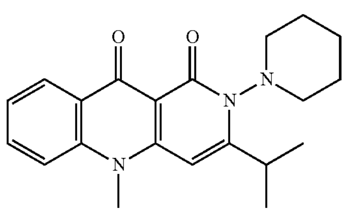 [SMILES: CC(C)c1cc2c(c(=O)c3ccccc3n2C)c(=O)n1N1CCCCC1] | 3-isopropyl-5-methyl-2-(piperidin-1-yl)benzo[b][1,6]naphthyridine-1,10(2H,5H)-dione | 0.67 | 352.2 |
| 2.15 | 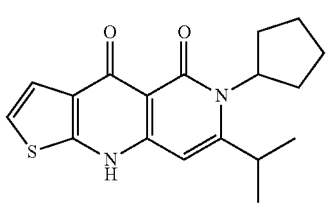 [SMILES: CC(C)c1cc2[nH]c3sccc3c(=O)c2c(=O)n1C1CCCC1] | 6-cyclopentyl-7-isopropylthieno[2,3-b][1,6]naphthyridine-4,5(6H,9H)-dione | 0.76 | 329.1 |
| 2.16 | 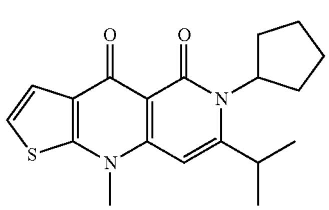 [SMILES: CC(C)c1cc2c(c(=O)c3ccsc3n2C)c(=O)n1C1CCCC1] | 6-cyclopentyl-7-isopropyl-9-methylthieno[2,3-b][1,6]naphthyridine-4,5(6H,9H)-dione | 0.59 | 343.1 |

| Ex | Structure | Name | LCMS Rt [min], meth. A | [M + H]+ |
|---|---|---|---|---|
| 2.17 | 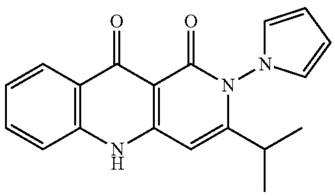 [SMILES: CC(C)c1cc2[nH]c3ccccc3c(=O)c2c(=O)n1-n1cccc1] | 3-isopropyl-2-(1H-pyrrol-1-yl)benzo[b][1,6]naphthyridine-1,10(2H,5H)-dione | 0.60 | 320.1 |
| 2.18 | 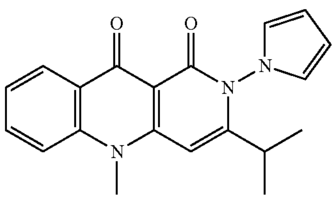 [SMILES: CC(C)c1cc2c(c(=O)c3ccccc3n2C)c(=O)n1-n1cccc1] | 3-isopropyl-5-methyl-2-(1H-pyrrol-1-yl)benzo[b][1,6]naphthyridine-1,10(2H,5H)-dione | 0.59 | 334.1 |

Example 3.1: 4-chloro-3-isopropyl-2-phenylbenzo[b][1,6]naphthyridine-1,10(2H,5H)-dione

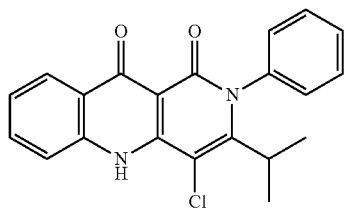 [SMILES: CC(C)c1c(Cl)c2[nH]c3ccccc3c(=O)c2c(=O)n1-c1ccccc1]

To a suspension of 50 mg (0.15 mmol) 3-isopropyl-2-phenylbenzo[b][1,6]naphthyridine-1,10(2H,5H)-dione (example 1.3) and 1 mg (7.6 μmol) aluminum trichloride in 1 mL pyridine and 0.43 mL acetic acid 20 mg (0.15 mmol) 1-chloropyrrolidine-2,5-dione was added in portions over 5 minutes and the mixture was stirred at 50° C. over 3 hours.

The reaction mixture was cooled to r.t., diluted with 3 mL water and stirred for one hour. The solid was filtered off, washed with water and dried to yield 40 mg (0.1 mmol, 69%) 4-chloro-3-isopropyl-2-phenylbenzo[b][1,6]naphthyridine-1,10(2H,5H)-dione as a yellow powder.

ESI-MS [M+H]+ 365.0; LCMS Rt [min], meth. A: 0.64; $^1$H-NMR (400 MHz, d$_6$-DMSO): δ (ppm)=10.90 (s, 1H), 8.14-8.05 (m, 2H), 7.75-7.68 (m, 1H), 7.60-7.50 (m, 3H), 7.40-7.31 (m, 3H), 2.81 (bs, 1H), 1.30 (d, J=7.1 Hz, 6H).

Example 3.2: 4-chloro-3-isopropyl-5-methyl-2-phenylbenzo[b][1,6]naphthyridine-1,10(2H,5H)-dione

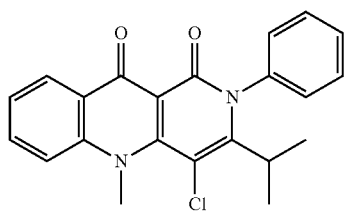 [SMILES: CC(C)c1c(Cl)c2c(c(=O)c3ccccc3n2C)c(=O)n1-c1ccccc1]

The compound was prepared starting from 100 mg (0.29 mmol) 3-isopropyl-5-methyl-2-phenylbenzo[b][1,6]naphthyridine-1,10(2H,5H)-dione (example 1.4) under the reaction conditions described for example 3.1 to yield 20 mg (53 mol, 18%) 4-chloro-3-isopropyl-5-methyl-2-phenylbenzo[b][1,6]naphthyridine-1,10(2H,5H)-dione as off-white solid.

ESI-MS [M+H]+ 379.2; LCMS Rt [min], meth. A: 0.66; $^1$H-NMR (400 MHz, d$_6$-DMSO): δ (ppm)=8.15-8.09 (m, 1H), 7.83-7.73 (m, 2H), 7.61-7.54 (m, 2H), 7.54-7.48 (m, 1H), 7.45-7.38 (m, 1H), 7.38-7.33 (m, 2H), 3.92 (s, 3H), 3.18 (d, J=3.8 Hz, 1H), 2.81 (bs, 1H), 1.30 (d, J=7.2 Hz, 6H).

Example 3.3: 4-bromo-3-isopropyl-5-methyl-2-phenylbenzo[b][1,6]naphthyridine-1,10(2H,5H)-dione

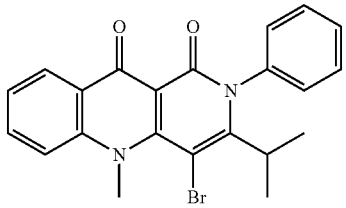 [SMILES: CC(C)c1c(Br)c2c(c(=O)c3ccccc3n2C)c(=O)n1-c1ccccc1]

The compound was prepared starting from 1.0 g (2.9 mmol) 3-isopropyl-5-methyl-2-phenylbenzo[b][1,6]naphthyridine-1,10(2H,5H)-dione (example 1.4) under the reaction conditions described for example 3.1 using 1.03 g (5.8 mmol) 1-bromopyrrolidine-2,5-dione, 20 mg (0.15 mmol) aluminum trichloride and mL acetic acid in 20 mL pyridine to yield 1.05 g (2.35 mmol, 81%) 4-bromo-3-isopropyl-5-methyl-2-phenylbenzo[b][1,6]naphthyridine-1,10(2H,5H)-dione as an off-white solid.

ESI-MS [M+H]+ 423.1; LCMS Rt [min], meth. A: 0.67; $^1$H-NMR (400 MHz, d$_6$-DMSO): δ (ppm)=8.15-8.08 (m, 1H), 7.82-7.75 (m, 2H), 7.61-7.48 (m, 3H), 7.44-7.38 (m, 1H), 7.38-7.33 (m, 2H), 3.93 (s, 3H), 2.93 (bs, 1H), 1.30 (bd, J=7.5 Hz, 6H).

Biological Testing

In-Vitro Testing: CFTR-Y122X Assay

Activity of compounds of the present invention was examined in recombinant, dual reporter isogenic Hek293 cell lines ("CFTR-Y122X assay"). The engineered reporter constructs contained the 18 bp sequence strech corresponding to a common Y122X PTC mutation in CFTR class I mutant patients (see Sermet-Gaudelus, BMC Medicine, 2007, 5(5)). Instead of a tyrosine (Y) in position 122 of the CFTR protein a TGA stop codon interrupts the open reading frame (Y122X) of the corresponding mRNA. This TGA stop codon triplet (followed by the pyrimidine base cytosine) is permissive to aminoglycoside mediated translational readthrough which served as positive control for high throughput screening. A corresponding TAA stop codon variant and a wildtype non mutated construct was used for confirmation and counter screening. The CFTR sequence was sandwiched between an eGFP reporter, and a triple myc tag sequence fused to a full length Renilla reporter. All sequences, including an intron containing one positioned pre-eGFP (b-globin intron) were cloned in frame. The corresponding expression constructs were stably expressed in the isogenic HEK-R4 cell host (Invitrogen Incorp.) and selected by blasticidin resistance. The isogenic integration of the construct minimizes gene dose effects and improves assay reproducibility. Stably integrated single cell derived clones were selected and characterized for aminoglycoside mediated readthrough. A clone with optimal growth characteristics and strong response ($EC_{50}$ of 1.5 mM) to paromomycin was pursued for HTS assay development. Readthrough of Y122X accumulates an intracellular localized fusion protein approximately 65.5 kDa in size as controlled by western blot analysis and immunofluorescence using an anti-renilla antibody. The eGFP reporter pre-PTC mutation serves as visual control for genetic stability of the screening clones and minimizes protein degradation of small fusion protein amounts. In the assay, compound concentration was 10 µM. In miniaturized 1536 well format 2000 cells were dispensed in 4 µl/well and incubated for 24 h at 37° C., 5% $CO_2$. 40 nl compounds were placed on the cells with control wells containing 1 ul Paramomycin and 14.4 mM final concentration. Compounds were incubated for 24 h. Renilla Glo substrate (2.5 ul) was added and plates were centrifuged and processed for luminescence measurement using various readers. Activity calculation was done using the equation: A1(%)=100*(S−NC)/(AC−NC) where AC, NC and S correspond to active controls (injection of Stimulation buffer=100% stimulation), neutral controls (buffer injection which Iloprost EC10) and screening samples (S). NC corresponds to 0% activity whereas AC is 100% activity (14 mM paromomycin). False positive artefacts were removed in confirmation and validation screening using the same assay format followed by counterscreening using the respective wildtype construct (w/o PTC mutation) cell model. Compounds were tested up to 100 µM compound concentration.

TABLE 2

In-vitro activity in CFTR-Y122X assay: Table 2 represents $AC_{50}$ values for nonsense mutation suppression in the CFTR-Y122X assay.

| Ex | $A_{max}$ [%] | $AC_{50}$ [µM] |
|---|---|---|
| 1.1 | 219 | 0.6 |
| 1.2 | 260 | 1.0 |
| 1.3 | 281 | 1.1 |
| 1.4 | 324 | 3.2 |
| 1.5 | 358 | 1.8 |
| 1.6 | 507 | 7.7 |
| 1.7 | 215 | 2.4 |
| 1.8 | 307 | 14.8 |
| 1.9 | 249 | 1.2 |
| 1.10 | 409 | 7.3 |
| 1.11 | 276 | 4.0 |
| 1.12 | 248 | 19.0 |
| 1.13 | 445 | 8.6 |
| 1.14 | 35 | —* |
| 1.15 | 224 | 5.5 |
| 1.16 | 344 | 1.6 |
| 1.17 | 430 | 9.2 |
| 1.18 | 240 | 3.9 |
| 1.19 | 253 | 12.8 |
| 1.20 | 183 | 2.5 |
| 1.21 | 379 | 5.4 |
| 1.22 | 413 | 7.2 |
| 1.23 | 414 | 5.2 |
| 1.24 | 157 | 18.4 |
| 1.25 | 87 | 16.8 |
| 1.26 | 229 | 3.3 |
| 1.27 | 206 | 3.0 |
| 1.28 | 257 | 12.8 |
| 1.29 | 286 | 0.7 |
| 1.30 | 324 | 0.7 |
| 1.31 | 228 | 0.6 |
| 1.32 | 247 | 4.2 |
| 1.33 | 243 | 19.4 |
| 1.34 | 263 | 1.0 |
| 1.35 | 126 | 0.4 |
| 1.36 | 177 | 4.1 |
| 1.37 | 164 | 1.4 |
| 1.38 | 215 | 2.3 |
| 1.39 | 239 | 1.2 |
| 1.40 | 300 | 1.0 |
| 1.41 | 223 | 0.5 |
| 1.42 | 134 | 3.9 |
| 1.43 | 186 | 22 |
| 1.44 | 178 | 0.4 |
| 1.45 | 252 | 0.6 |
| 1.46 | 247 | 3.4 |
| 1.47 | 312 | 5.2 |
| 1.48 | 227 | 1.8 |
| 1.49 | 17 | —* |
| 1.50 | 110 | 16.9 |
| 1.51 | 144 | 16.5 |
| 1.52 | 49 | 21 |
| 2.1 | 229 | 0.5 |
| 2.2 | 262 | 2.1 |
| 2.3 | 235 | 0.4 |
| 2.4 | 274 | 1.8 |
| 2.5 | 217 | 2.7 |
| 2.6 | 232 | 3.3 |
| 2.7 | 197 | 0.7 |
| 2.8 | 188 | 6.1 |
| 2.9 | 198 | 4.2 |
| 2.10 | 177 | 10.0 |
| 2.11 | 2026 | 0.9 |
| 2.12 | 178 | 1.7 |
| 2.13 | 265 | 1.8 |
| 2.14 | 271 | 1.7 |
| 2.15 | 124 | —* |
| 2.16 | 279 | 1.2 |
| 2.17 | 237 | 9.0 |
| 2.18 | 75 | 17.6 |
| 3.1 | 211 | 3.2 |
| 3.2 | 220 | 17.2 |
| 3.3 | 122 | 18.8 |

*not determined

Table 2 shows that compounds of formula (I') show activity in a functional assay indicating they promote translational readthrough.

The following compounds of formula (I') were tested in the above described CFTR-Y122X assay at the above dose ranges and suppression reaching only less than 5% of paromomycin reference activity was seen:

7-isopropyl-3-methyl-6-phenylthieno[2,3-b][1,6]naphthyridine-4,5(6H,9H)-dione;

7-isopropyl-3,9-dimethyl-6-phenylthieno[2,3-b][1,6]naphthyridine-4,5(6H,9H)-dione.

In an embodiment of the invention, the compound of the invention is not 7-isopropyl-3-methyl-6-phenylthieno[2,3-b][1,6]naphthyridine-4,5(6H,9H)-dione 7-isopropyl-3,9-dimethyl-6-phenylthieno[2,3-b][1,6]naphthyridine-4,5(6H,9H)-dione.

The invention claimed is:

1. A compound of formula (Ia') in free form or in pharmaceutically acceptable salt form, wherein:

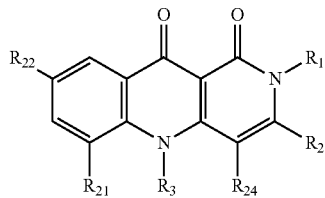

(Ia')

$R_1$ is selected from a five- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_6$; pyrrolyl; pyrazolyl; thiophenyl; and pyridin-2-yl; and

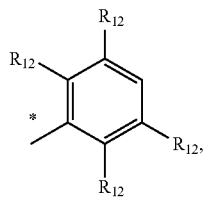

wherein the phenyl ring is attached via the bond marked with an asterisk (*), and wherein the pyrrolyl, pyrazolyl, thiophenyl, and pyridin-2-yl may be substituted by $C_{1-3}$alkyl;

wherein when $R_1$ is a five- to seven-membered monocyclic saturated or unsaturated non-aromatic ring system, then $R_2$ is selected from $C_{2-6}$alkyl which may be substituted once or more than once by $R_7$; —$X_1$—$R_8$; and a three- to seven-membered monocyclic aromatic, saturated or unsaturated non-aromatic ring system, wherein said ring system may contain from 1 to 4 hetero atoms selected from nitrogen, oxygen and sulfur, and wherein said ring system may be substituted once or more than once by $R_{11}$;

or wherein when $R_1$ is pyrrolyl, pyrazolyl, thiophenyl, pyridin-2-yl, or phenyl, then $R_2$ is selected from $C_{2-7}$alkyl which may be substituted once or more than once by $R_{13}$; —$X_2$—$R_{14}$; and a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$;

$X_1$— is —O—, —S— or —N($R_9$)—;

$X_2$— is —O—, —S— or —N($R_{15}$)—;

$R_3$ is hydrogen or —$CH_2R_{18}$;

$R_8$ is $C_{1-6}$alkyl which may be substituted once or more than once by $R_{10}$;

$R_9$ is hydrogen or $C_{1-4}$alkyl;

each $R_{12}$ independently is hydrogen, halogen, hydroxyl, amino, cyano, nitro, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{1-4}$alkoxy, $C_{1-4}$halogenalkoxy, $C_{1-4}$alkylamino or di($C_{1-4}$alkyl)amino; or $C_{3-6}$cycloalkyl, wherein one carbon atom may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;

$R_{14}$ is $C_{1-6}$alkyl which may be substituted once or more than once by $R_{16}$;

$R_{15}$ is hydrogen or $C_{1-4}$alkyl;

$R_{18}$ is hydrogen, $C_{1-4}$alkyl, $C_{2-6}$alkenyl, $C_{3-6}$cycloalkyl, $C_{1-3}$alkoxy$C_{1-3}$alkyl, hydroxy$C_{1-3}$alkyl or amino$C_{1-3}$alkyl;

$R_{21}$ is hydrogen, halogen, hydroxyl, amino, cyano, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{1-4}$alkoxy, $C_{1-4}$halogenalkoxy, $C_{1-4}$alkylamino, di($C_{1-4}$alkyl)amino; or a three- to seven-membered monocyclic aromatic, saturated or unsaturated non-aromatic ring system, wherein said ring system may contain from 1 to 4 hetero atoms selected from nitrogen, oxygen and sulfur, wherein said ring system may be attached directly or via a $C_{1-2}$alkylene, and wherein said ring system may be substituted once or more than once by $R_{23}$;

$R_{22}$ is hydrogen, halogen, hydroxyl, cyano, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{2-4}$alkenyl, $C_{2-4}$alkinyl, $C_{1-4}$alkoxy, $C_{1-4}$halogenalkoxy, or $C_{3-4}$cycloalkyl, wherein one carbon atom of the $C_{3-4}$cycloalkyl may be replaced by an oxygen atom, wherein the $C_{3-4}$cycloalkyl may be attached directly or via a $C_{1-2}$alkylene, and wherein the $C_{3-4}$cycloalkyl may be substituted once or more than once by halogen;

$R_6$, $R_{11}$, $R_{17}$, and $R_{23}$ each independently is halogen, hydroxyl, amino, cyano, nitro, $C_{1-4}$alkyl, $C_{1-4}$halogenalkyl, $C_{1-4}$hydroxyalkyl, $C_{1-4}$alkoxy-$C_{1-4}$alkyl, amino-$C_{1-4}$alkyl, $C_{1-4}$alkyl-amino-$C_{1-4}$alkyl, di($C_{1-4}$alkyl)-amino-$C_{1-4}$alkyl, $C_{1-4}$alkoxy, $C_{1-4}$halogenalkoxy, $C_{1-4}$alkylamino, di($C_{1-4}$alkyl)amino, or $C_{3-6}$cycloalkyl, wherein one carbon atom of the $C_{3-6}$cycloalkyl may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;

or two $R_6$, $R_{11}$, $R_{17}$, and $R_{23}$ at the same ring atom together are oxo;

or two $R_6$, $R_{11}$, $R_{17}$, and $R_{23}$ at the same ring carbon atom together with said carbon atom form a $C_{3-6}$cycloalkyl;

$R_7$, $R_{10}$, $R_{13}$, and $R_{16}$ each independently is halogen, hydroxyl, amino, cyano, nitro, $C_{1-4}$alkoxy, $C_{1-4}$halogenalkoxy, $C_{1-4}$alkylamino, di($C_{1-4}$alkyl)amino, or $C_{3-6}$cycloalkyl, wherein one carbon atom of the $C_{3-6}$cycloalkyl may be replaced by an oxygen atom, wherein the $C_{3-6}$cycloalkyl may be attached directly or via a $C_{1-2}$alkylene, and wherein the $C_{3-6}$cycloalkyl may be substituted once or more than once by halogen;
or two $R_7$, $R_{10}$, $R_{13}$, or $R_{16}$ at the same carbon atom together are oxo;
or two $R_7$, $R_{10}$, $R_{13}$, or $R_{16}$ at the same carbon atom together with said carbon atom form a $C_{3-6}$cycloalkyl; and
$R_{24}$ is hydrogen or halogen.

2. A compound of formula (Ia') in free form or in a pharmaceutically acceptable salt form according to claim 1, wherein:
$R_1$ is phenyl;
$R_{12}$ for each occurrence is hydrogen; and
$R_2$ is selected from $C_{2-7}$alkyl which may be substituted once or more than once by $R_{13}$; and a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$.

3. A compound of formula (Ia') in free form or in a pharmaceutically acceptable salt form according to claim 1, wherein:
$R_1$ is a ring selected from pyrazolyl, thiophenyl and pyridin-2-yl, which ring may be substituted by $C_{1-3}$alkyl; and
$R_2$ is selected from $C_{2-7}$alkyl which may be substituted once or more than once by $R_{13}$; and a three- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_{17}$.

4. A compound of formula (Ia') in free form or in a pharmaceutically acceptable salt form according to claim 1, wherein:
$R_1$ is a five- to seven-membered monocyclic saturated or unsaturated non-aromatic ring system, wherein said ring system may contain from 1 to 4 hetero atoms selected from nitrogen, oxygen and sulfur, and wherein said ring system may be substituted once or more than once by $R_6$; and
$R_2$ is selected from $C_{2-6}$alkyl which may be substituted once or more than once by $R_7$ and a three- to seven-membered monocyclic aromatic, saturated or unsaturated non-aromatic ring system, wherein said ring system may contain from 1 to 4 hetero atoms selected from nitrogen, oxygen and sulfur, and wherein said ring system may be substituted once or more than once by $R_{11}$.

5. A compound in free form or in pharmaceutically acceptable salt form, which is selected from:
3-cyclobutyl-2-phenylbenzo[b][1,6]naphthyridine-1,10(2H,5H)-dione;
3-cyclobutyl-5-methyl-2-phenylbenzo[b][1,6]naphthyridine-1,10(2H,5H)-dione;
3-isopropyl-2-phenylbenzo[b][1,6]naphthyridine-1,10(2H,5H)-dione;
3-isopropyl-5-methyl-2-phenylbenzo[b][1,6]naphthyridine-1,10(2H,5H)-dione;
8-fluoro-3-isopropyl-2-phenylbenzo[b][1,6]naphthyridine-1,10(2H,5H)-dione;
8-fluoro-3-isopropyl-5-methyl-2-phenylbenzo[b][1,6]naphthyridine-1,10(2H,5H)-dione;
8-chloro-3-isopropyl-2-phenylbenzo[b][1,6]naphthyridine-1,10(2H,5H)-dione;
8-chloro-3-isopropyl-5-methyl-2-phenylbenzo[b][1,6]naphthyridine-1,10(2H,5H)-dione;
3-isopropyl-8-methyl-2-phenylbenzo[b][1,6]naphthyridine-1,10(2H,5H)-dione;
3-isopropyl-5,8-dimethyl-2-phenylbenzo[b][1,6]naphthyridine-1,10(2H,5H)-dione;
9-isopropyl-8-phenyl-1H-indolo[1,7-ab][1,6]naphthyridine-6,7(2H,8H)-dione;
7-isopropyl-6-phenylthieno[2,3-b][1,6]naphthyridine-4,5(6H,9H)-dione;
7-isopropyl-9-methyl-6-phenylthieno[2,3-b][1,6]naphthyridine-4,5(6H,9H)-dione;
7-isopropyl-2-methyl-6-phenylthieno[2,3-b][1,6]naphthyridine-4,5(6H,9H)-dione;
7-isopropyl-2,9-dimethyl-6-phenylthieno[2,3-b][1,6]naphthyridine-4,5(6H,9H)-dione;
6-isopropyl-7-phenylthieno[3,2-b][1,6]naphthyridine-8,9(4H,7H)-dione;
6-isopropyl-4-methyl-7-phenylthieno[3,2-b][1,6]naphthyridine-8,9(4H,7H)-dione;
6-isopropyl-2-methyl-7-phenylthieno[3,2-b][1,6]naphthyridine-8,9(4H,7H)-dione;
6-isopropyl-2,4-dimethyl-7-phenylthieno[3,2-b][1,6]naphthyridine-8,9(4H,7H)-dione;
6-isopropyl-3-methyl-7-phenylthieno[3,2-b][1,6]naphthyridine-8,9(4H,7H)-dione;
6-isopropyl-3,4-dimethyl-7-phenylthieno[3,2-b][1,6]naphthyridine-8,9(4H,7H)-dione;
3-isopropyl-2-phenyl-6,7,8,9-tetrahydrobenzo [1,6]naphthyridine-1,10(2H,5H)-dione;
3-isopropyl-2-phenyl-5,6,7,8-tetrahydro-1H-cyclopenta[b][1,6]naphthyridine-1,9(2H)-dione;
3-cyclobutyl-5-methyl-2-phenyl-5,6,7,8-tetrahydro-1H-cyclopenta[b][1,6]naphthyridine-1,9(2H)-dione;
3-cyclobutyl-2-phenyl-5,6,7,8-tetrahydro-1H-cyclopenta[b][1,6]naphthyridine-1,9(2H)-dione;
3-cyclobutyl-5-methyl-2-phenyl-6,7,8,9-tetrahydrobenzo[b][1,6]naphthyridine-1,10(2H,5H)-dione;
7-cyclobutyl-9-methyl-6-phenylthieno[2,3-b][1,6]naphthyridine-4,5(6H,9H)-dione;
7-cyclobutyl-2,9-dimethyl-6-phenylthieno[2,3-b][1,6]naphthyridine-4,5 (6H,9H)-dione;
7-cyclobutyl-6-phenylthieno[2,3-b][1,6]naphthyridine-4,5(6H,9H)-dione;
7-cyclobutyl-2-methyl-6-phenylthieno[2,3-b][1,6]naphthyridine-4,5(6H,9H)-dione;
6-cyclobutyl-4-methyl-7-phenylthieno[3,2-b][1,6]naphthyridine-8,9(4H,7H)-dione;
6-cyclobutyl-7-phenylthieno[3,2-b][1,6]naphthyridine-8,9(4H,7H)-dione;
6-cyclobutyl-2,4-dimethyl-7-phenylthieno[32-b][1,6]naphthyridine-8,9(4H,7H)-dione;
6-cyclobutyl-2-methyl-7-phenylthieno[3,2-b][1,6]naphthyridine-8,9(4H,7H)-dione;
3-cyclobutyl-5,8-dimethyl-2-phenylbenzo[b][1,6]naphthyridine-1,10(2H,5H)-dione;
3-cyclobutyl-8-fluoro-5-methyl-2-phenylbenzo[b][1,6]naphthyridine-1,10(2H,5H)-dione;
8-chloro-3-cyclobutyl-2-phenylbenzo[b][1,6]naphthyridine-1,10(2H,5H)-dione;
3-cyclobutyl-8-methyl-2-phenylbenzo[b][1,6]naphthyridine-1,10(2H,5H)-dione;

8-chloro-3-cyclobutyl-5-methyl-2-phenylbenzo[b][1,6]naphthyridine-1,10(2H,5H)-dione;
3-isopropyl-6-methoxy-5-methyl-2-phenylbenzo[b][1,6]naphthyridine-1,10(2H,5H)-dione;
3-cyclobutyl-8-fluoro-2-phenylbenzo[b][1,6]naphthyridine-1,10(2H,5H)-dione;
9-cyclobutyl-8-phenyl-1H-indolo[1,7-ab][1,6]naphthyridine-6,7(2H, 8H)-dione;
3-cyclobutyl-6-methoxy-5-methyl-2-phenylbenzo[b][1,6]naphthyridine-1,10(2H,5H)-dione;
3-isopropyl-6-methoxy-2-phenylbenzo[b][1,6]naphthyridine-1,10(2H,5H)-dione;
3-cyclobutyl-6-methoxy-2-phenylbenzo[b][1,6]naphthyridine-1,10(2H,5H)-dione;
3-isopropyl-8-methoxy-5-methyl-2-phenylbenzo[b][1,6]naphthyridine-1,10(2H,5H)-dione;
3-isopropyl-8-methoxy-2-phenylbenzo[b][1,6]naphthyridine-1,10(2H,5H)-dione;
8-hydroxy-3-isopropyl-5-methyl-2-phenylbenzo[b][1,6]naphthyridine-1,10(2H,5H)-dione;
6-hydroxy-3-isopropyl-5-methyl-2-phenylbenzo[b][1,6]naphthyridine-1,10(2H,5H)-dione;
3-cyclobutyl-2-cyclopentylbenzo[b][1,6]naphthyridine-1,10(2H,5H)-dione;
3-cyclobutyl-2-cyclopentyl-5-methylbenzo[b][1,6]naphthyridine-1,10(2H,5H)-dione;
2-cyclopentyl-3-isopropylbenzo[b][1,6]naphthyridine-1,10(2H,5H)-dione;
2-cyclopentyl-3-isopropyl-5-methylbenzo[b][1,6]naphthyridine-1,10(2H,5H)-dione;
3-cyclobutyl-2-(pyridin-2-yl)benzo[b][1,6]naphthyridine-1,10(2H, 5H)-dione;
3-cyclobutyl-5-methyl-2-(pyridin-2-yl)benzo[b][1,6]naphthyridine-1,10(2H, 5H)-dione;
3-cyclobutyl-2-(pyrrolidin-1-yl)benzo[b][1,6]naphthyridine-1,10(2H, 5H)-dione;
3-cyclobutyl-5-methyl-2-(pyrrolidin-1-yl)benzo[b][1,6]naphthyridine-1,10(2H,5H)-dione;
4-chloro-3-isopropyl-2-phenylbenzo[b][1,6]naphthyridine-1,10(2H, 5H)-dione;
4-chloro-3-isopropyl-5-methyl-2-phenylbenzo[b][1,6]naphthyridine-1,10(2H,5H)-dione; and
4-bromo-3-isopropyl-5-methyl-2-phenylbenzo[b][1,6]naphthyridine-1,10(2H,5H)-dione.

6. A pharmaceutical composition comprising a therapeutically effective amount of a compound according to claim 1 and one or more pharmaceutically acceptable carriers.

7. A compound in free form or in pharmaceutically acceptable salt form selected from the group consisting of:
3-cyclobutyl-5-methyl-2-phenylbenzo[b][1,6]naphthyridine-1,10 (2H,5H)-di one;
3-isopropyl-2-phenylbenzo[b][1,6]naphthyridine-1,10 (2H,5H)-dione;
3-isopropyl-5-methyl-2-phenylbenzo[b][1,6]naphthyridine-1,10(2H,5H)-dione;
3-cyclobutyl-2-cyclopentyl-5-methylbenzo[b][1,6]naphthyridine-1,10(2H,5H)-dione;
2-cyclopentyl-3-isopropylbenzo[b][1,6]naphthyridine-1,10(2H, 5H)-dione; and
2-cyclopentyl-3-isopropyl-5-methylbenzo[b][1,6]naphthyridine-1,10(2H,5H)-dione.

8. A compound in free form or in pharmaceutically acceptable salt form according to claim 7 which is 3-cyclobutyl-5-methyl-2-phenylbenzo[b][1,6]naphthyridine-1, 10(2H,5H)-di one.

9. A compound in free form or in pharmaceutically acceptable salt form according to claim 7 which is 3-isopropyl-2-phenylbenzo[b][1,6]naphthyridine-1,10(2H,5H)-dione.

10. A compound in free form or in pharmaceutically acceptable salt form according to claim 7 which is 3-isopropyl-5-methyl-2-phenylbenzo[b][1,6]naphthyridine-1,10 (2H,5H)-dione.

11. A compound in free form or in pharmaceutically acceptable salt form according to claim 7 which is 3-cyclobutyl-2-cyclopentyl-5-methylbenzo[b][1,6]naphthyridine-1,10(2H,5H)-dione.

12. A compound in free form or in pharmaceutically acceptable salt form according to claim 7 which is 2-cyclopentyl-3-isopropylbenzo[b][1,6]naphthyridine-1,10(2H, 5H)-dione.

13. A compound in free form or in pharmaceutically acceptable salt form according to claim 7 which is 2-cyclopentyl-3-isopropyl-5-methylbenzo[b][1,6]naphthyridine-1, 10(2H,5H)-dione.

14. A pharmaceutical composition comprising a therapeutically effective amount of a compound according to claim 7 and one or more pharmaceutically acceptable carriers.

* * * * *